United States Patent
Kudela et al.

(10) Patent No.: US 12,350,399 B2
(45) Date of Patent: *Jul. 8, 2025

(54) POLYPHOSPHATE-FUNCTIONALIZED INORGANIC NANOPARTICLES AS HEMOSTATIC COMPOSITIONS AND METHODS OF USE

(71) Applicants: The Regents of the University of California, Oakland, CA (US); The Board of Trustees of the University of Illinois, Urbana, IL (US)

(72) Inventors: Damien Kudela, Santa Barbara, CA (US); Galen D. Stucky, Santa Barbara, CA (US); Anna May-Masnou, Barcelona (ES); Gary Bernard Braun, San Diego, CA (US); James H. Morrissey, Champaign, IL (US); Stephanie A. Smith, Urbana, IL (US)

(73) Assignees: The Regents of the University of California, Oakland, CA (US); The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,233

(22) Filed: May 31, 2023

(65) Prior Publication Data
US 2024/0157022 A1 May 16, 2024

Related U.S. Application Data

(63) Continuation of application No. 17/099,400, filed on Nov. 16, 2020, now Pat. No. 11,707,550, which is a
(Continued)

(51) Int. Cl.
*A61L 24/04* (2006.01)
*A61K 47/59* (2017.01)
(Continued)

(52) U.S. Cl.
CPC .......... *A61L 24/046* (2013.01); *A61K 47/595* (2017.08); *A61K 47/6923* (2017.08);
(Continued)

(58) Field of Classification Search
CPC ............ A61K 47/6923; A61K 47/6935; A61K 47/595; A61L 24/046; A61L 24/02;
(Continued)

(56) References Cited

U.S. PATENT DOCUMENTS 7,682,808 B2 3/2010 Morrissey
7,927,629 B2 4/2011 Simone et al.
(Continued)

FOREIGN PATENT DOCUMENTS

EP 3062830 9/2016
WO WO2001072313 A1 10/2001
(Continued)

OTHER PUBLICATIONS

Suzawa et al., "Synthesis and HPLC analysis of enzymatically cleavable linker consisting of poly(ethylene glycol) and dipeptide for the development of immunoconjugate" in Journal of Controlled Release 69 (2000) pp. 27-41. (Year: 2000).*
(Continued)

*Primary Examiner* — Blessing M Fubara
(74) *Attorney, Agent, or Firm* — Rudy J. Ng; Carol L. Francis; Bozicevic, Field & Francis LLP

(57) ABSTRACT

A hemostatic composition is provided. The hemostatic composition includes a hemostatically effective amount of a hemostatic agent that includes a nanoparticle and a polyphosphate polymer attached to the nanoparticle. Also provided are medical devices and methods of use to promote blood clotting.

10 Claims, 74 Drawing Sheets

Specification includes a Sequence Listing.

Related U.S. Application Data continuation of application No. 16/390,451, filed on Apr. 22, 2019, now Pat. No. 10,842,908, which is a continuation of application No. 14/883,224, filed on Oct. 14, 2015, now Pat. No. 10,293,077, which is a continuation of application No. 14/201,434, filed on Mar. 7, 2014, now Pat. No. 9,186,417.

(60) Provisional application No. 61/775,354, filed on Mar. 8, 2013.

(51) Int. Cl.
  *A61K 47/69* (2017.01)
  *A61L 24/02* (2006.01)

(52) U.S. Cl.
  CPC .......... *A61K 47/6935* (2017.08); *A61L 24/02* (2013.01); *A61L 2300/404* (2013.01); *A61L 2300/418* (2013.01); *A61L 2400/04* (2013.01); *A61L 2400/12* (2013.01); *Y10T 428/2982* (2015.01)

(58) Field of Classification Search
  CPC .......... A61L 2300/404; A61L 2300/418; A61L 2400/04; A61L 2400/12; Y10T 428/2982
  See application file for complete search history.

(56) References Cited

U.S. PATENT DOCUMENTS

| | | | | |
|---|---|---|---|---|
| 8,257,740 | B1 | 9/2012 | Sung et al. | |
| 8,821,861 | B2 | 9/2014 | Smith et al. | |
| 9,061,014 | B2 | 6/2015 | Seward et al. | |
| 9,186,417 | B2* | 11/2015 | Kudela | A61K 47/6923 |
| 9,241,958 | B2 | 1/2016 | Smith et al. | |
| 10,293,077 | B2* | 5/2019 | Kudela | A61K 47/6935 |
| 10,842,908 | B2* | 11/2020 | Kudela | A61L 24/046 |
| 11,707,550 | B2* | 7/2023 | Kudela | A61K 47/6923 |
| | | | | 424/78.37 |
| 2002/0031679 | A1 | 3/2002 | Yano et al. | |
| 2006/0198837 | A1 | 9/2006 | Morrissey et al. | |
| 2010/0209946 | A1 | 8/2010 | Jing et al. | |
| 2010/0297246 | A1 | 11/2010 | Weitzmann et al. | |
| 2010/0300326 | A1* | 12/2010 | Carlini | C09D 11/322 |
| | | | | 106/31.77 |
| 2011/0059162 | A1* | 3/2011 | Reed | A61L 29/085 |
| | | | | 424/488 |
| 2012/0135062 | A1 | 5/2012 | Nisbet | |
| 2012/0244602 | A1 | 9/2012 | Okumura et al. | |
| 2012/0282320 | A1* | 11/2012 | Scherr | C08J 3/24 |
| | | | | 514/474 |
| 2015/0283287 | A1 | 10/2015 | Agarwal et al. | |
| 2016/0263275 | A1 | 9/2016 | Thauern et al. | |
| 2020/0297854 | A1 | 9/2020 | Ingber et al. | |

FOREIGN PATENT DOCUMENTS

| | | |
|---|---|---|
| WO | WO 2012101218 | 8/2012 |
| WO | WO2012101218 A1 | 8/2012 |
| WO | WO 2013173235 A1 | 11/2013 |

OTHER PUBLICATIONS

Ong et al., "Development of chitosan-based wound dressing with improved hemostatic and antimicrobial properties," in Biomaterials, vol. 29, Issue 32, Nov. 2008, pp. 4323-4332, cited by applicant in 1449 filed Feb. 19, 2025. (Year: 2008).*
Suzawa et al., (2000) "Synthesis and HPLC Analysis of Enzymatically Cleavable Linker Consisting of Poly(Ethylene Glycol) and Dipeptide for the Development of Immunoconjugate", J. Controlled Release 69(1):27-41.
Choi et al., (2011) "Polyphosphate is a Cofactor for the Activation of Factor XI by Thrombin", Blood, 118:6963-6970.
Choi et al., (2010) "Phosphoramidate End Labeling of Inorganic Polyphosphates: Facile Manipulation of Polyphosphate for Investigating and Modulating its Biological Activities", Biochemistry 49(45): 9935-9941.
Morrissey et al., (2012) "Polyphosphate: An Ancient Molecule that Links Platelets, Coagulation and Inflammation", Blood 119:5972-5979.
Müller et al., (2009) "Platelet Polyphosphates are Proinflammatory and Procoagulant Mediators in vivo", Cell 139:1143-1156.
Mutch et al., (2010) "Polyphosphate Binds with High Affinity to Exosite II of Thrombin", J Thromb Haemost 8:548-555.
Semeraro et al., (2011) "Extracellular Histones Promote Thrombin Generation through Platelet-Dependent Mechanisms: Involvement of Platelet TLR2 and TLR4", Blood 118:1952-1961.
Smith et al., (2008) "Polyphosphate as a General Procoagulant Agent", J Thromb Haemost 6:1750-1756.
Smith and Morrissey (2008) "Polyphosphate Enhances Fibrin Clot Structure", Blood 112:2810-2816.
Smith et al., (2012) "Inhibition of Polyphosphate as a Novel Strategy for Preventing Thrombosis and Inflammation", Blood, 120:5103-5110.
Smith et al., (2010) "Polyphosphate Exerts Differential Effects on Blood Clotting, Depending on Polymer Size", Blood 116: 4353-4359.
Smith et al., (2006) "Polyphosphate Modulates Blood Coagulation and Fibrinolysis", Proc Natl Acad Sci USA 103:903-908.
Tavano et al., (2010) "Procoagulant Properties of Bare and Highly PEGylated Vinyl-Modified Silica Nanoparticles", Nanomedicine (Lond) 5(6):881-896.
Yun and Morrissey (2009) "Polyphosphate and Omptins: Novel Bacterial Procoagulant Agents", J. Cell Molec. Med. 13:4146-4153.
Kastrup et al., (2007) "Characterization of the Threshold Response of Initiation of Blood Clotting to Stimulus Patch Size", Biophysical Journal 93(8), 2969-2977.
Lorenz et al., (1994) "Preparation and Use of Polyphosphate-Modified Zirconia for Purification of Nucleic Acids and Proteins", Anal. Biochem. 216:118-126.
Stöber and Fink (1968) "Controlled Growth of Monodisperse Silica Spheres in the Micron Size Range", Journal of Colloid and Interface Science 26:62-69.
Riewald et al., (2003) "Science review: Role of coagulation protease casades in sepsis," in Critical Care , 7: 123-129.
Santomauro et al., (2012) "Biomineralization of Zinc-Phosphate-Based Nano Needles by Living Microalgae", Journal of Biomaterials and Nanobiotechnology, 3: 362-370.
Smith et al.; (2010) "Polyphophate exerts differential effects on blood clotting, depending on polymer size," Blood, 116(20): 4353-4359.
Aatonen et al., (2012) Platelet-Derived Microvesicles: Multitalented Participants in Intercellular Communication, Semin Thromb Hemost, 102-113, 38(01).
Alam et al. (2005) Hemorrhage control in the battlefield: Role of new hemostatic agents. Military Medicine 170(1):63-69.
Alam, et al. (2004) Application of a zeolite hemostatic agent achieves 100% survival in a lethal model of complex groin injury in swine. Journal of Trauma-Injury Infection and Critical Care 56(5):974-983.
Baker et al. (2007) Controlling bioprocesses with inorganic surfaces: Layered clay hemostatic agents. Chem. Mater. 19(18):4390-4392.
Baker et al. (2008) Blood clot initiation by mesocellular foams: dependence on nanopore size and enzyme immobilization. Langmuir 24(24):14254-14260.
Bowman et al. (2011) Toxicity of aluminum silicates used in hemostatic dressings toward human umbilical veins endothelial cells, hela cells, and raw267.4 mouse macrophages. *Journal of Trauma—Injury Infection and Critical Care* 71(3):727-732.
Bull et al. (2009) Postoperative bypass bleeding: A bypass- associated dilutional (BAD) coagulopathy? *Blood Cells Molecules and Diseases* 43(3):256-259.

(56) References Cited

OTHER PUBLICATIONS

Cauda et al. (2010) Colchicine-loaded lipid bilayer-coated 50 nm mesoporous nanoparticles efficiently induce microtubule depolymerization upon cell uptake. *Nano Lett.* 10(7):2484-2492.

Cauda et al.(2010) Impact of different PEGylation patterns on the long-term bio- stability of colloidal mesoporous silica nanoparticles. *J. Mater. Chem.* 20(39):8693- 8699.

Cosgriff et al. (1997) Predicting life-threatening coagulopathy in the massively transfused trauma patient: Hypothermia and acidoses revisited. *Journal of Trauma—Injury Infection and Critical Care* 42(5):857-861.

Darlington et al. (2011) Coagulation changes to systemic acidosis and bicarbonate correction in swine. Journal of Trauma-Injury Infection and Critical Care 71(5):1271-1277.

Donovan et al. (2014) Size-Controlled Synthesis of Granular Polyphosphate Nanoparticles at Physiologic Salt Concentrations for Blood Clotting. *BioMacromolecules* 15(11):1-9.

Driscoll (1995) The toxicology of crystalline silica studied in vitro. (Proceedings of the International Conference on the Crystalline Silica Health Effects: Current State of the Art), pp. 1118-1125.

Finnie et al. (2009) Biodegradability of sol-gel silica microparticles for drug delivery. *J. Sol-Gel Sci. Technol.* 49(1):12-18.

Gaharwar et al. (2014) Shear-Thinning Nanocomposite Hydrogels for the Treatment of Hemorrhage. ACS Nano, 8(10): 9833-9842.

Geeraedts et al. (2009) Exsanguination in trauma: A review of diagnostics and treatment options. *Injury—International Journal of the Care of the Injured* 40(1): 11-20.

Gerlach et al. (2010) Preliminary Study of the Effects of Smectite Granules (WoundStat) on Vascular Repair and Wound Healing in a Swine Survival Model. *Journal of Trauma-Injury Infection and Critical Care* 69(5):1203-1209.

Ghadiri et al. (2014) Antibiotic eluting clay mineral (Laponite((R))) for wound healing application: an in vitro study. *Journal of Materials Science-Materials in Medicine* 25(11):2513-2526.

Gordy et al. (2011) Military applications of novel hemostatic devices. *Expert Review of Medical Devices* 8(1):41-47.

Gwinn & Vallyathan (2006) Nanoparticles: Health effects—Pros and cons. *Environ. Health Perspect.* 114(12):1818-1825.

Hafeli et al., (2009) "Cell uptake and in vitro toxicity of magnetic nanoparticles suitable for drug delivery," Molecular Pharmaceutics, Articles, 2009, 12 pages.

Kheirabadi (2011) Evaluation of topical hemostatic agents for combat wound treatment. *U.S. Army Medical Department journal*:25-37.

Kheirabadi et al. (2009) Comparison of new hemostatic granules/powders with currently deployed hemostatic products in a lethal model of extremity arterial hemorrhage in swine. *Journal of Trauma-Injury Infection and Critical Care* 66(2):316-328.

Kheirabadi et al. (2009) Determination of Efficacy of New Hemostatic Dressings in a Model of Extremity Arterial Hemorrhage in Swine. *Journal of Trauma-Injury Infection and Critical Care* 67(3):450-460.

Kheirabadi et al. (2010) Clot-inducing minerals versus plasma protein dressing for topical treatment of external bleeding in the presence of coagulopathy. *Journal of Trauma-Injury Infection and Critical Care* 69(5): 1062-1072.

Kheirabadi et al. (2010) Safety evaluation of new hemostatic agents, smectite granules, and kaolin-coated gauze in a vascular injury wound model in swine. *Journal of Trauma-Injury Infection and Critical Care* 68(2):269-277.

Kheirabadi et al. (2013) In vivo assessment of the Combat Ready Clamp to control junctional hemorrhage in swine. *Journal of Trauma and Acute Care Surgery* 74(5):1260-1265.

Kudela et al. (2015) Clotting activity of polyphosphate functionalized silica nanoparticles *Angew Chem Int Ed Engl* 54(13): 4018-4022.

Lashof-Sullivan et al. (2013) Intravenous hemostats: Challenges in translation to patients. *Nanoscale* 5(22):10719-10728.

Lee & Whitesides (2010) Analysis of inorganic polyphosphates by capillary gel electrophoresis. *Anal. Chem.* 82(16):6838-6846.

Li et al. (2013) Cytotoxicity and potency of mesocellular foam-26 in comparison to layered clays used as hemostatic agents. *Toxicol Res-Uk* 2(2):136-144.

Lin et al. (2012) Critical considerations in the biomedical use of mesoporous silica nanoparticles. *Journal of Physical Chemistry Letters* 3(3):364-374.

Lorenz et al. (1997) Anti-HIV-1 activity of inorganic polyphosphates. *Journal of Acquired Immune Deficiency Syndromes and Human Retrovirology* 14(2):110-118.

Lu et al. (2010) Biocompatibility, biodistribution, and drug-delivery efficiency of mesoporous silica nanoparticles for cancer therapy in animals. *Small* 6(16):1794-1805.

Martini & Holcomb (2007) Acidosis and coagulopathy—The differential effects on fibrinogen synthesis and breakdown in pigs. Annals of Surgery 246(5):831-835.

Martini (2009) Coagulopathy by hypothermia and acidosis: Mechanisms of thrombin generation and fibrinogen availability. *Journal of Trauma-Injury Infection and Critical Care* 67(1):202-209.

Martini et al. (2006) Does bicarbonate correct coagulation function impaired by acidosis in swine? *Journal of Trauma-Injury Infection and Critical Care* 61(1):99-106.

Martini et al.(2005) Independent contributions of hypothermia and acidosis to coagulopathy in swine. *Journal of Trauma-Injury Infection and Critical Care* 58(5):1002-1009.

Mellaerts et al. (2008) Increasing the oral bioavailability of the poorly water soluble drug itraconazole with ordered mesoporous silica. *European Journal of Pharmaceutics and Biopharmaceutics* 69(1):223-230.

Nigretto JM, Corretge E, & Jozefowicz M (1989) Contributions of negatively charged chemical groups to the surface-dependent activation of human-plasma by soluble dextran derivatives. *Biomaterials* 10(7):449-454.

Ong et al. (2008) Development of a chitosan-based wound dressing with improved hemostatic and antimicrobial properties. *Biomaterials* 29(32):4323-4332.

Ostomei et al. (2007) Metal oxide surface charge mediated Hemostasis. *Langmuir* 23(22):11233-11238.

Ostomei et al. (2006) Host-guest composites for induced hemostasis and therapeutic healing in traumatic injuries. *Journal of Thrombosis and Thrombolysis* 22(1):55-67.

Park et al. (2009) Biodegradable luminescent porous silicon nanoparticles for in vivo applications. *Nature Materials* 8(4):331-336.

Park, et al. (2009) Systematic surface engineering of magnetic nanoworms for in vivo tumor targeting. *Small* 5(6):694-700.

Phillips et al. (2014) Clinical translation of an ultrasmall inorganic optical-PET imaging nanoparticle probe. *Sci Transl Med.* 6(260) 1-23.

Pozza & Millner (2011) Celox (chitosan) for haemostasis in massive traumatic bleeding: experience in Afghanistan. *European Journal of Emergency Medicine* 18(1):31-33.

Pusateri et al. (2004) Application of a granular mineral-based hemostatic agent (QuikClot) to reduce blood loss after grade V liver injury in swine. *Journal of Trauma-Injury Infection and Critical Care* 57(3):555-562.

Ramaker et al. (2009) Effects of acidosis, alkalosis, hyperthermia and hypothermia on haemostasis: results of point of care testing with the thromboelastography analyser. *Blood Coagulation & Fibrinolysis* 20(6):436-439.

Rao & Sharma (1997) Use of chitosan as a biomaterial: Studies on its safety and hemostatic potential. *Journal of Biomedical Materials Research* 34(1):21-28.

Reddy et al., (2012) "Magnetic nanoparticles: design and characterization, toxicity and biocompatibility, pharmaceutical and biomedical applications," Chemical Reviews, 5818-5878, 112,11.

Rosenholm et al., (2011) "Multifunctional Mesoporous Silica Nanoparticles for Combined Therapeutic, Diagnostic and Targeted Action in Cancer Treatment," Current Drug Targets, 1166-1186, 12, 8.

Santomauro et al. (2012) Biomineralization of Zinc-Phosphate-Based Nano Needles by Living Microalgae. *Journal of Biomedical Materials and Nanobiotechnology*, 3-362-370.

(56) References Cited

OTHER PUBLICATIONS

Sena et al. (2013) A pilot study of the use of kaolin-impregnated gauze (Combat Gauze) for packing high-grade hepatic injuries in a hypothermic coagulopathic swine model. *Journal of Surgical Research* 183(2):704-709.
Singh et al. (2011) Bioresponsive mesoporous silica nanoparticles for triggered drug release. *J. Am. Chem. Soc.* 133(49):19582-19585.
Slowing et al. (2008) Mesoporous silica nanoparticles as controlled release drug delivery and gene transfection carriers. *Advanced Drug Delivery Reviews* 60(11):1278-1288.
Tarn et al. (2013) Mesoporous silica nanoparticle nanocarriers: Biofunctionality and biocompatibility. *Acc. Chem. Res.* 46(3):792-801.
Thompson & Butterworth (1992) The nature of laponite and its aqueous dispersions. *J. Colloid Interface Sci.* 151(1):236-243.
Trewyn et al. (2007) Mesoporous silica nanoparticle based controlled release, drug delivery, and biosensor systems. *Chem. Commun.* (31):3236-3245.
Vogler & Siedlecki (2009) Contact activation of blood-plasma coagulation. *Biomaterials* 30(10):1857-1869.
Waibel et al (2011) Safety of chitosan bandages in shellfish allergic patients. *Military Medicine* 176(10):1153-1156.
Wei et al. (1999) Electrokinetic properties of colloidal zirconia powders in aqueous suspension. *J. Am. Ceram. Soc.* 82(12):3385-3392.
Wolberg (2007) Thrombin generation and fibrin clot structure. *Blood Reviews* 21(3):131-142.
Xia et al. (2009) Polyethyleneimine Coating Enhances the Cellular Uptake of Mesoporous Silica Nanoparticles and Allows Safe Delivery of siRNA and DNA Constructs. *Acs Nano* 3(10):3273-3286.
Xue M, Cao D, Stoddart JF, & Zink JI (2012) Size-selective pH-operated megagates on mesoporous silica materials. *Nanoscale* 4(23):7569-7574.
Zreiqat et al. (2002) Mechanisms of magnesium-stimulated adhesion of osteoblastic cells to commonly used orthopaedic implants. *Journal of Biomedical Materials Research* 62(2):175-184.
Gegel et al. (2012) The effects of QuikClot Combat Gauze and movement on hemorrhage control in a porcine model. *Military Medicine* 177(12):1543-1547.

* cited by examiner

PLGA Methodology

FMS NPs

A) SiO$_2$ -> SiO$_2$-amine; using aminopropylsilane
SiO$_2$-amine -> SiO$_2$-thioacetyl; using SATP B) Deprotection:
SiO$_2$-thioacetyl -> SiO$_2$-SH; using NH$_2$OH C) Assay:
SiO$_2$-SH + DTNB -> yellow product

| Sample | PolyP Type | MonoP Conc. (uM) | Gold Particle Conc. (nM) | Aggregation # | UV-vis Peak for Bulk Gold | Peak After Centrifuging | Volume (uL) |
|---|---|---|---|---|---|---|---|
| MS_26_10 nm | 70 | 307.37 | 131.09 | 33.50 | 519 | 524 | 300 |
| MS_27_15 nm | 70 | 311.63 | 67.08 | 66.37 | 521 | 522 | 250 |
| MS_28_50 nm | 70 | 312.63 | 8.62 | 518.05 | 532 | 533 | 200 |

FIG. 102

POLYPHOSPHATE-FUNCTIONALIZED INORGANIC NANOPARTICLES AS HEMOSTATIC COMPOSITIONS AND METHODS OF USE

CROSS-REFERENCE TO RELATED APPLICATIONS

This application is a continuation of U.S. application Ser. No. 17/099,400, filed Nov. 16, 2020, now U.S. Pat. No. 11,707,550, which is a continuation of U.S. application Ser. No. 16/390,451, filed Apr. 22, 2019, now U.S. Pat. No. 10,842,908, which is a continuation of U.S. application Ser. No. 14/883,224, filed Oct. 14, 2015, now U.S. Pat. No. 10,293,077, which is a continuation of U.S. application Ser. No. 14/201,434, filed Mar. 7, 2014, now U.S. Pat. No. 9,186,417, which pursuant to 35 U.S.C. § 119(e), claims priority to the filing date of U.S. Provisional Application No. 61/775,354, filed Mar. 8, 2013, the disclosures of which are incorporated herein by reference.

GOVERNMENT SUPPORT

This invention was made with Government support under Grant No. W81XWH-11-2-0021 awarded by the U.S. Army Medical Research and Development Command (USAMRDC) and Grant No. W911NF-10-2-0114 awarded by the Army Research Office (ARO). The Government has certain rights in the invention.

INCORPORATION BY REFERENCE OF A SEQUENCE LISTING PROVIDED AS AN XML FILE

A Sequence Listing is provided herewith as a Sequence Listing XML, "UCSB-535CON4_seq_listing_ST26" created on Dec. 17, 2024 and having a size of 9,824 bytes. The contents of the Sequence Listing XML are incorporated by reference herein in their entirety.

INTRODUCTION

Treatment of bleeding wounds, particularly severely bleeding wounds, can require immediate attention to bring the bleeding under control. Severe bleeding poses a very real risk of death to the casualty if not treated quickly. Although loss of about 10-15% of total blood volume can be endured without clinical sequelae in a healthy person, if a laceration or penetrating trauma (e.g., knife or gun wound) is severe enough or involves critical arteries or veins, this volume of blood can be lost in a matter of minutes. The bleeding must be slowed immediately or irreversible damage to organs and mortality can result.

Bleeding wounds, even those that may be less severe, can pose serious difficulties and risks when a severe wound is inflicted in a remote area or other situations (such as found in a battlefield) where full medical assistance may be not immediately available. In such circumstances it can be critical to undertake measures to slow or stop bleeding so that the subject can be transported to a medical facility.

Various methods and hemostatic compositions for promoting blood clotting have been developed, and can be applied to help control bleeding in such situations. The field continues to develop additional hemostatic compositions that provide for, for example, rapid initiation of blood clotting, increased rate of blood clotting, sufficient blood clot strength, and/or reduced adverse side effects. Of interest are such hemostatic compositions that can be rapidly and safely applied in an emergency situation, such as on the battlefield or at the scene of an accident, without the need for intensive training or equipment.

SUMMARY

A hemostatic composition is provided. The hemostatic composition includes a hemostatically effective amount of a hemostatic agent that includes a nanoparticle and a polyphosphate polymer attached to the nanoparticle. Also provided are medical devices and methods of use to promote blood clotting.

Aspects of the present disclosure include a hemostatic composition that includes a hemostatically effective amount of a hemostatic agent that includes a nanoparticle and a polyphosphate polymer attached to the nanoparticle.

In some embodiments, the polyphosphate polymer includes 20 or more phosphate monomers. In some embodiments, the polyphosphate polymer includes 70 or more phosphate monomers.

In some embodiments, the hemostatic agent has a polyphosphate polymer to nanoparticle mass ratio of 1:2 or more. In some embodiments, the hemostatic agent has a polyphosphate polymer to nanoparticle mass ratio of 1:1 or more.

In some embodiments, the nanoparticle includes a material such as silica, diatomaceous earth, titanium dioxide, and calcium hydroxyapatite. In some embodiments, the nanoparticle includes silica.

In some embodiments, the nanoparticle has an average diameter of 100 nm or less.

In some embodiments, the hemostatic agent further includes a protecting agent attached to the hemostatic agent by an enzymatically-cleavable linking group. In some embodiments, the protecting agent includes a polyethylene glycol polymer. In some embodiments, the polyethylene glycol polymer has a molecular mass of 1000 Da or more.

Aspects of the present disclosure include a medical device that includes a hemostatic composition and a sterile substrate on which the hemostatic composition is disposed. The hemostatic composition includes a nanoparticle and a polyphosphate polymer attached to the nanoparticle.

In some embodiments, the substrate is adapted for delivery of the hemostatic composition to a bleeding wound. In some embodiments, the substrate is a bandage, gauze, or sponge.

In some embodiments, the medical device includes a sealed package containing the hemostatic composition.

Aspects of the present disclosure include a method of promoting blood clotting at a hemorrhage site. The method includes administering to a hemorrhage site in a subject the hemostatic composition as described herein for a period of time sufficient to at least initiate blood clotting at the hemorrhage site.

In some embodiments, the hemorrhage site is an external hemorrhage site. In some embodiments, the administering includes applying the hemostatic composition to the external hemorrhage site.

In some embodiments, the hemorrhage site is an internal hemorrhage site, and the hemostatic composition is a hemostatic composition includes a protecting agent attached to the hemostatic agent by an enzymatically-cleavable linking group. In some embodiments, the administering includes intravenously administering the hemostatic composition to the subject.

These and other embodiments of the invention will be readily apparent to the ordinarily skilled artisan upon reading the present specification.

BRIEF DESCRIPTION OF THE DRAWINGS

FIG. 9(left) shows an image of the blue coumarin dye experiment at time 0 min, and FIG. 9(right) shows an image of the blue coumarin dye experiment at time 20 min.

FIG. 34, panel B, shows gold particle pellet after centrifugation, according to embodiments of the present disclosure.

As shown in FIG. 35, panel A, samples are inserted into the dispersing channel. The inlet channel contains sol-gel silica, which precipitates upon contact with the media to form spherical nanoparticles. FIG. 35, panel B, shows a side view of the schematic, which illustrates how the spherical nanoparticles form. Particle sizes for PLGA averaged about 125 nm.

FIG. 43, right, shows images of the uptake of various samples by HDFs, with Ag NP concentration of 20 μg/ml; Kaolin concentration of 20 μg/ml; and MCF-26 concentration of 100 μg/ml.

FIG. 75, panel A, shows polyP conjugated to cystamine, and FIG. 75, panel B, shows polyP-cystamine attached to the surface of gold nanoparticles.

FIG. 83, panel A, shows a schematic representation. FIG. 83, panel B, shows an image of PAAc and PAAm aqueous solutions were mixed thoroughly at 20° C. FIG. 83, panel C, shows an image of a mixture that was heated to 40° C. FIG. 83, panel D, shows an image of a solution that was cooled back to 20° C.

FIG. 84, panel A, shows a reaction for the conjugation of PAAc or PAAm to cystamine or DDA. FIG. 84, panel B, shows PAAc-cystamine or PAAm-DDA attached to the surface of gold nanoparticles.

FIG. 102 shows the sample conditions for polyP70 conjugated to gold nanoparticles (10 nm, 15 nm, and 50 nm).

DEFINITIONS

Figure 1:
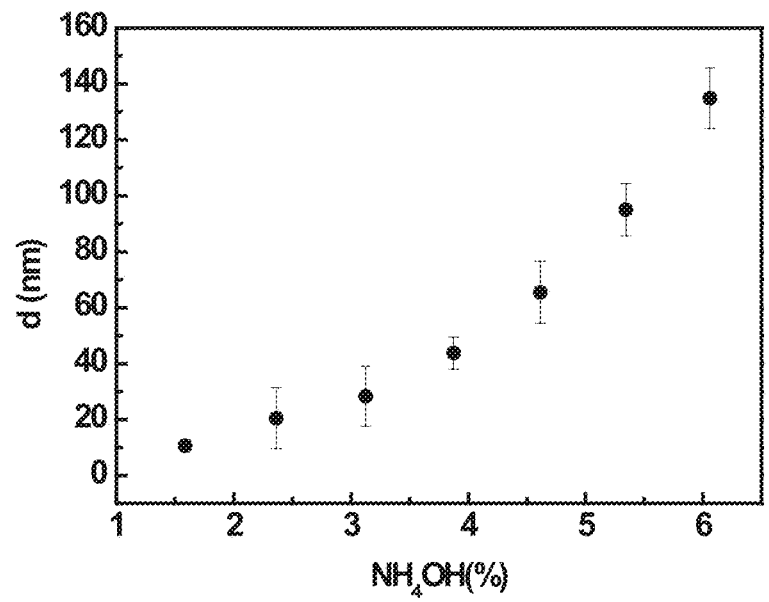
FIG. 1 shows a graph of average particle size (nm) vs. amount of $NH_4OH$ (%) added to a reaction to produce silica nanoparticles, according to embodiments of the present disclosure.

A "hemostatic agent" refers to an agent which promotes blood clotting, e.g., following administration to hemorrhage site (e.g., an external or internal wound). Hemostatic agents encompass, for example, inorganic materials (e.g., silica nanoparticles, polyphosphate, and the like, as described herein), as well as biologically active ions (e.g., ions that act as cofactors in the clotting cascade (e.g., by serving as an ionic bridge)), and/or facilitated colloid precipitation (e.g., red blood cell precipitation), clotting factor proteins (e.g., thrombin, etc.), combinations thereof, and the like.

A "hemostatic composition" refers to a composition that includes at least one hemostatic agent. A hemostatic composition may further include one or more additional components, which may be hemostatically active (e.g., promote blood clotting or promote activity of the hemostatic agent in the hemostatic composition in blood clotting). Hemostatic compositions can also contain agents that are hemostatically inert.

The term "hemostasis" as used herein refers to inhibition of bleeding, including the arrest of bleeding, which is accompanied by blood clot formation.

A "hemostatically effective amount" refers to an amount of a hemostatic composition which, following application to a hemorrhage site, is effective to facilitate blood clotting (e.g., as compared to time to clot formation in the absence of the hemostatic agent), increase blood clotting rate as compared to a blood clotting rate in the absence of the hemostatic agent, and/or improve blood clot strength as compared to blood clot strength in the absence of the hemostatic agent. Clot strength can be measured by Thrombelastograph® (TEG) measurements. Assays for assessing hemostatic activity are known in the art, with exemplary methods described herein.

The term "isolated" means the compound is present in an environment other than that in which it is found in nature. "Isolated" is meant to include compounds that are within samples that are substantially enriched for the compound of interest and/or in which the compound of interest is partially or substantially purified.

As used herein, the term "purified" refers to a compound that is removed from its natural environment and is at least 60% free, such as 75% or more free, or 90% or more free from other components with which it is naturally associated.

The terms "individual," "subject," "host," and "patient," used interchangeably herein, refer to any subject in need to treatment, e.g., mammals, including, but not limited to, humans, simians, felines, canines, equines, bovines, mammalian farm animals, mammalian sport animals, and mammalian pets. Human subjects in need of treatment are of interest.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise.

Thus, for example, reference to "a hemostatic agent" includes a plurality of such agents and reference to "the hemostatic agent" includes reference to one or more agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Embodiments of the present disclosure relate to hemostatic compositions that include a hemostatically effective amount of a hemostatic agent that includes a nanoparticle and a polyphosphate polymer attached to the nanoparticle. Also provided are medical devices and methods of use to promote blood clotting.

Hemostatic Agents

Aspects of the present disclosure include biologically active agents configured to promote blood clotting. These hemostatic agents include a nanoparticle and a polyphosphate polymer attached to the nanoparticle. By "nanoparticle" is meant a particle that has dimensions in the nanometer scale, such as dimensions of 1000 nm or less, such as 750 nm or less, including 500 nm or less, or 250 nm or less, or 200 nm or less, or 150 nm or less, or 100 nm or less, or 50 nm or less, or 40 nm or less, or 30 nm or less, or 25 nm or less, or 20 nm or less, or 15 nm or less, or 10 nm or less, or 5 nm or less. In some instances, the nanoparticle has dimensions of 100 nm or less. The term "average" as used herein is meant to be the arithmetic mean.

In certain embodiments, the nanoparticle is spherical in shape, although in other embodiments, other shapes of the nanoparticle may also be included. For example, some embodiments of the nanoparticle have a shape such as, but not limited to, an ellipsoid, a rod, a cone, a cube, a cuboid (e.g., a rectangular box), a pyramid, an irregular shape, etc. In certain instances, combinations of different shapes of nanoparticles may be included. As indicated above, the nanoparticle may be substantially spherical in shape, and thus may have dimensions measured as a diameter of the sphere, such as an average diameter of 1000 nm or less, such as 750 nm or less, including 500 nm or less, or 250 nm or less, or 200 nm or less, or 150 nm or less, or 100 nm or less, or 50 nm or less, or 40 nm or less, or 30 nm or less, or 25 nm or less, or 20 nm or less, or 15 nm or less, or 10 nm or less, or 5 nm or less. In some instances, a substantially spherical nanoparticle has an average diameter of 100 nm or less.

In certain embodiments, the nanoparticle is non-porous. By "non-porous" is meant that the nanoparticle is substantially solid, such that the accessible surface (e.g., solvent accessible surface, such as an exterior surface of the particle the may be contacted by a surrounding fluid) of the nanoparticle is the exterior surface of the nanoparticle. In some instances, a non-porous nanoparticle does not have pores exposed on the surface of the nanoparticle. In other embodiments, the nanoparticle is porous. A porous nanoparticle may have one or more pores exposed on the surface of the nanoparticle, such that the accessible surface of the nanoparticle includes the exterior surface of the nanoparticle and the interior surfaces of the one or more pores within the nanoparticle. In certain cases, a porous nanoparticle has a greater accessible surface area than a non-porous nanoparticle of the same shape and average dimensions.

The pore size of a porous nanoparticle can be selected to provide for desired clot-promoting activity (e.g., clotting rate, clotting time, clot strength, etc.). Average pore size is generally determined by the BET-BJH calculation of $N_2$ desorption/adsorption isotherm data. In some embodiments, the average pore size of a porous nanoparticle ranges from 1 to 100 nm, such as 1 nm to 75 nm, including 1 nm to 50 nm, or 5 nm to 50 nm, or 5 nm to 40 nm, or 5 nm to 30 nm, or 10 nm to 30 nm. In certain cases, the average pore size of the porous nanoparticle is from 10 nm to 30 nm. In some embodiments, the porous nanoparticle has an average pore size of 1 nm or more, such as 5 nm or more, including 10 nm or more, or 15 nm or more, or 20 nm or more, or 25 nm or more, or 30 nm or more, or 35 nm or more, or 40 nm or more, or 45 nm or more, or 50 nm or more, with the proviso that the average pore size is 100 nm or less. In certain embodiments, the porous nanoparticle has an average pore size of 10 nm or more. In some embodiments, the porous nanoparticle may have an average pore size of 50 nm or less, such as 45 nm or less, including 40 nm or less, or 35 nm or less, or 30 nm or less, or 25 nm or less, or 20 nm or less, or 15 nm or less, or 10 nm or less, or 5 nm or less, or 1 nm or less. In certain embodiments, the porous nanoparticle may have an average pore size of 30 nm or less.

In certain embodiments, the nanoparticle is composed of an oxide of silicon, aluminum, a transition metal (e.g., titanium, zirconium, and the like), aluminosilicate, or combination thereof. Exemplary materials for the nanoparticle include, but are not limited to, silicon dioxide (e.g., silica), titanium dioxide, silicon-aluminum-oxide, aluminum oxide, iron oxide, polymers (e.g., polystyrene), metals (e.g., gold), and the like. In some instances, the nanoparticle is composed of other inorganic materials, such as, but not limited to, diatomaceous earth, calcium hydroxyapatite, and the like. Combinations of the above materials may also be included.

In certain embodiments, the nanoparticle is a thermal treated nanoparticle. For example, the nanoparticle may be treated at high temperature, such as in a calcination process. In some instances, the nanoparticles are treated (e.g., calcined) at a temperature of 200° C. or more, such as 250° C. or more, or 300° C. or more, or 350° C. or more, or 400° C. or more, or 450° C. or more, or 500° C. or more, or 550° C. or more, or 600° C. or more, or 650° C. or more, or 700° C. or more, or 750° C. or more. In certain embodiments, the nanoparticles are treated (e.g., calcined) at a temperature of 250° C. In certain embodiments, the nanoparticles are treated (e.g., calcined) at a temperature of 550° C. In some instances, thermal treatment of the nanoparticles facilitates a reduction in the zeta potential of the nanoparticles. In some instances, a hemostatic agent with a lower zeta potential has increased hemostatic activity. In some cases, the hemostatic agent has a zeta potential of 0 mV or less, such as −1 mV or less, or −5 mV or less, or −10 mV or less, or −15 mV or less, or −20 mV or less, or −25 mV or less, or −30 mV or less. In certain embodiments, the hemostatic agent has a zeta potential of −15 mV or less.

In certain embodiments, the nanoparticle may have hemostatic activity, such that the nanoparticle promotes blood clotting (e.g., as compared to blood clotting in the absence of the hemostatic agent). As such, a nanoparticle with hemostatic activity may be described as being hemostatically effective. For example, without being limited to any particular theory, the nanoparticle may have a negative surface charge in body fluid (e.g., blood), which may facilitate activation of the coagulation cascade by activating Factor XII. The promotion of blood clotting may be described by one or more of the following factors: (1) reduction in initial time for blood clot formation (R, min); (2) increase in the rate of clot formation ($\alpha$, deg); (3) increase in clot strength or maximum amplitude (MA, mm); and (4) reduction in time until clot reaches 20 mm (K, min).

As described above, in certain embodiments, the hemostatic agent includes a polyphosphate polymer (polyP) attached to the nanoparticle. In certain instances, the polyphosphate polymer is hemostatically effective to promote blood clotting (e.g., as compared to blood clotting in the absence of the hemostatic agent). For example, without being limited to any particular theory, the polyphosphate polymer may facilitate activation of the coagulation cascade through activation of Factor Xa. As such, the polyphosphate polymer may facilitate blood clotting through activation of a different target (e.g., enzyme or zymogen) in the coagulation cascade than the nanoparticle.

In some cases, a hemostatic agent that includes a polyphosphate polymer attached to a nanoparticle has a greater hemostatic activity than the nanoparticle itself. For instance, a hemostatic agent that includes a polyphosphate polymer attached to a nanoparticle may have a clotting time, R, (e.g., time until first evidence of a clot is detected) as measured by thrombelastography that is less than the clotting time of the nanoparticle itself. In some cases, a hemostatic agent that includes a polyphosphate polymer attached to a nanoparticle has a clotting time, R, of 15 min or less, such as 10 min or less, or 5 min or less, or 4.5 min or less, or 4 min or less, or 3.5 min or less, or 3 min or less, or 2.5 min or less, or 2 min or less, or 1.5 min or less, or 1 min or less, or 0.5 min or less. In some embodiments, a hemostatic agent that includes a polyphosphate polymer attached to a nanoparticle has a clotting time, R, of 3 min or less. In some embodiments, a hemostatic agent that includes a polyphosphate polymer attached to a nanoparticle has a clotting time, R, of 2.5 min or less. In some embodiments, a hemostatic agent that includes a polyphosphate polymer attached to a nanoparticle has a clotting time, R, of 2 min or less. In some embodiments, a hemostatic agent that includes a polyphosphate polymer attached to a nanoparticle has a clotting time, R, of 1.5 min or less. In some embodiments, a hemostatic agent that includes a polyphosphate polymer attached to a nanoparticle has a clotting time, R, of 1 min or less.

In certain embodiments, a hemostatic agent that includes a polyphosphate polymer attached to a nanoparticle has a greater hemostatic activity that the polyphosphate polymer itself. For example, a hemostatic agent that includes a polyphosphate polymer attached to a nanoparticle may have a clotting time, R, (as described above) which is less than the clotting time of the polyphosphate itself. In some instances, a hemostatic agent that includes a polyphosphate polymer attached to a nanoparticle may promote blood clotting with a shorter polyphosphate polymer length as compared to polyphosphate alone (i.e., a free polyphosphate polymer). For instance, a hemostatic agent that includes a short (e.g., 100mer or less, such as 70mer) polyphosphate polymer attached to a nanoparticle may produce a significant reduction in clotting time as compared to a short polyphosphate polymer alone. In some instances, the clotting time of a hemostatic agent that includes a short (e.g., 100mer or less, such as 70mer) polyphosphate polymer attached to a nanoparticle may be less than or equal to the clotting time of a long (e.g., 500mer or greater) polyphosphate polymer alone.

The polyphosphate polymer may be composed of two or more phosphate monomers attached together to form the polyphosphate polymer. For example, the polyphosphate polymer may include 2 or more monomers, such as 5 or more, including 10 or more, or 20 or more, or 30 or more, or 40 or more, or 50 or more, or 60 or more, or 70 or more, or 80 or more, or 90 or more, or 100 or more, or 150 or more, or 200 or more, or 250 or more, or more, or 300 or more, or 400 or more, or 500 or more, or 600 or more, or 700 or more, or 800 or more, or 900 or more, or 1000 or more, or 1100 or more, or 1200 or more, or 1300 or more, or 1400 or more, or 1500 or more phosphate monomers. In certain cases, the polyphosphate polymer composition includes an average of 70 phosphate monomers per polymer. In other embodiments, the polyphosphate polymer composition includes an average of 700 phosphate monomers per polymer. Combinations of different sized phosphate polymers may also be included. For instance, the polyphosphate polymer composition may have from 2 to 200 phosphate monomers per polymer, such as from 5 to 200, including from 10 to 200, or from 10 to 150, or from 10 to 100, of from 20 to 100, or from 30 to 100, or from 40 to 100, or from 50 to 100 phosphate monomers per polymer. In other instances, the polyphosphate polymer composition may have from 100 to 1500 phosphate monomers per polymer, such as from 100 to 1400, or from 100 to 1300, or from 200 to 1300 phosphate monomers per polymer.

In certain embodiments, the polyphosphate polymer is attached to the nanoparticle. For example, the polyphosphate polymer may be adsorbed on the surface of the nanoparticle. The binding interaction can be based on one or more of a variety of binding interactions between the polyphosphate polymer and the nanoparticle, such as, but not limited to, covalent bonds, ionic bonds, electrostatic interactions, hydrophobic interactions, hydrogen bonds, van der Waals forces (e.g., London dispersion forces), dipole-dipole interactions, combinations thereof, and the like. The polyphosphate polymer may be attached to the nanoparticle through a linking group between the nanoparticle surface or pores and the polyphosphate polymer. The binding interactions may be substantially permanent (e.g., requiring a relatively large amount of energy to overcome the binding interaction, such as with covalent bonds) or may be reversible (e.g., requiring a relatively low amount of energy to disrupt the binding interaction, such as with dipole-dipole interactions). For example, the polyphosphate polymer may be attached to the nanoparticle via a phosphoramidate bond, ester linkage, carboxylic acid linkage, or another form of linkage. In certain embodiments, bonds may be altered in strength depending on factors present or arising in the body (e.g., enzymes, fibrin, etc.), or affected by externally applied fields (e.g., magnetic, etc.), or by injection of a modifier agent directed at the polyphosphate polymer, linkage, or nanoparticle.

Embodiments of the hemostatic agent include a nanoparticle and a polyphosphate polymer, as described above. In certain embodiments, the hemostatic agent has a composition with a particular mass ratio of the polyphosphate polymer to the nanoparticle. For instance, the hemostatic agent may have a polyphosphate polymer to nanoparticle mass ratio of 1:10 or more, such as 1:9 or more, including 1:8 or more, or 1:7 or more, or 1:6 or more, or 1:5 or more, or 1:4 or more, or 1:3 or more, or 1:2 or more, or 1:1 or more, or 2:1 or more, or 3:1 or more, or 4:1 or more, or 5:1 or more. In some embodiments, the hemostatic agent has a polyphosphate polymer to nanoparticle mass ratio of 1:2 or more, such as 1:2. In some embodiments, the hemostatic agent has a polyphosphate polymer to nanoparticle mass ratio of 1:1 or more, such as 1:1.

In certain embodiments, the hemostatic agent includes a protecting agent. The protecting agent may be substantially unreactive in the body, such as substantially unreactive towards elements of the coagulation cascade. The protecting agent may be configured to reduce or inhibit the hemostatic activity of the hemostatic agent. For example, in certain instances, the protecting agent may be configured to block or cover the accessible surface of the polyphosphate polymer, such that interactions between the polyphosphate polymer and its target (e.g., enzyme or zymogen or fibrin surfaces) are reduced or inhibited. This reduction or inhibition in the interaction between the polyphosphate polymer and its target may be sufficient to facilitate a reduction in the activation of the target as compared to when the protecting agent is not present. For example, a hemostatic agent that includes a protecting agent may have substantially no hemostatic activity, such that the hemostatic agent that includes a protecting agent does not significantly promote blood clotting as compared to blood clotting in the absence of the hemostatic agent.

In certain embodiments, the protecting agent is attached to the hemostatic agent. In some cases, the protecting agent is removably attached to the hemostatic agent. In these embodiments, the protecting group may be attached to the hemostatic agent and then may be subsequently detached (e.g., cleaved) from the hemostatic agent to release the hemostatic agent from the protecting agent. When the protecting agent is removed from the hemostatic agent, the polyphosphate polymer attached to the surface of the nanoparticle may be exposed, and thus may be accessible for interactions with its target as described above. In these embodiments, a removable protecting agent may facilitate activation of the hemostatic agent at a desired site of action, e.g., a hemorrhage site, such as an internal hemorrhage site in a subject. For example, removal of the protecting group from the hemostatic agent may produce a free hemostatic agent that has hemostatic activity, such that the free hemostatic agent promotes blood clotting as compared to blood clotting in the presence of the hemostatic agent attached to the protecting group (or as compared to blood clotting in the absence of the hemostatic agent).

In certain embodiments, the protecting agent is attached to the nanoparticle. In some instances, the protecting agent is attached to the polyphosphate polymer. The protecting agent may be attached to the end of the polyphosphate polymer, or attached to a fraction of the phosphate oxygen atoms in the polyphosphate polymer. In certain cases, the protecting agent is attached to the hemostatic agent at a combination of sites including the nanoparticle and the polyphosphate polymer (e.g., the end of the polyphosphate polymer and/or an internal binding site). The protecting group can be covalently or non-covalently associated to the hemostatic agent using a mediator having affinity to the nanoparticle (e.g., silica) or polyphosphate (e.g., phosphoramidate linkage). The mediator may be cleaved by one or more proteases. The mediator can be composed of alternating repeats of affinity parts, linkers, and cleavable parts. In certain instances, the summary affinity (avidity) is stronger than any partially cleaved product. The mediator can also be crosslinked to other mediators in the hemostatic agent, either covalently or non-covalently.

In certain instances, the protecting agent is composed of a polymer. The polymer may be configured to be substantially unreactive in the body, such as substantially unreactive towards elements of the coagulation cascade. As such, the polymer may be configured to reduce or inhibit the hemostatic activity of the hemostatic agent as described above. In some instances, the protecting agent includes a polyethylene glycol (PEG) polymer. The PEG polymer may be branched or unbranched as desired, as long as the function of the PEG polymer is maintained as described above. In some cases, the PEG polymer has an average molecular mass of 1000 Da or more, such as 1500 Da or more, including 2000 Da or more, or 3000 Da or more, or 4000 Da or more, or 5000 Da or more, or 6000 Da or more, or 7000 Da or more, or 8000 Da or more, or 9000 Da or more, or 10,000 Da or more, or 15,000 Da or more, or 20,000 Da or more. In certain instances, the PEG polymer has an average molecular mass of 2000 Da. In certain instances, the PEG polymer has an average molecular mass of 1000 Da.

In certain embodiments, the mass ratio of PEG to polyphosphate ranges from 1:1000 to 1000:1, such as from 1:900 to 900:1, including from 1:800 to 800:1, or from 1:700 to 700:1, or from 1:600 to 600:1, or from 1:500 to 500:1, or from 1:400 to 400:1, or from 1:300 to 300:1, or from 1:200 to 200:1, or from 1:100 to 100:1, or from 1:75 to 75:1, or from 1:50 to 50:1, or from 1:25 to 25:1, or from 1:10 to 10:1, or from 1:5 to 5:1. In some instances, the mass ratio of PEG to polyphosphate ranges from 1:50 to 50:1. In certain embodiments, the protecting agent is composed of one or more of the following: PEG; polyvinylpyrrolidone (PVP); poly(lactic-co-glycolic acid) (PLGA); polypropylene glycol; poly(carboxybetaine); poly(sulfobetaine); poly(carboxybetaine methacrylate) (PCBMA); polyoxamers; polypeptides; biodegradable materials such as polylactonic acid and its derivatives, collagens, albumin, gelatin, hyaluronic acid, starch, cellulose (e.g., methylcellulose, hydroxypropylcellulose, hydroxypropylmethylcellulose, carboxymethylcellulosephthalat, casein, dextrane, polysaccharides, fibrinogen, poly(D,L-lactide), poly(D,L-lactide-co-glycolide), and the like; polyurethanes; poly(ethylene vinyl acetate); silicones; acrylic polymers like polyacrylic acids, polymethylacrylic acid, polyacrylcyanoacrylate; polyethylene; polypropylene; polyamide; poly(ester urethane); poly(ether urethane); poly(ester urea); polyethers such as polyethylene oxide, polypropylene oxide, pluronics, polytetramethylene glycol; vinyl polymers such as polyvinylpyrrolidone, poly (vinyl alcohol), poly(vinylacetatephthalate); parylenes; polyurethane; poly(hydroxybutylate); poly(alkyl carbonates); poly(orthoesters); polyesters; poly(hydroxyvaleric acid); polydioxanone; poly(ethylene terephthalate); poly (malic acid); poly(tartronic acid); polyanhydrides; polyphosphohazenes; and the like, or copolymers thereof. Polymer variations are further described in EP 1830902 A2, the disclosure of which is incorporated herein by reference.

In certain embodiments, the protecting agent is attached to the hemostatic agent by a linking group. In some cases, the linking group is an enzymatically-cleavable linking group. For example, the linking group may be an enzymatically-cleavable peptide linking group. The cleavable peptide linking group may be configured such that it is specifically recognized and cleaved by a target enzyme. For instance, the target enzyme may be an enzyme that has an activity localized to a particular area(s) in a subject, such as a particular target site of action for the hemostatic agent. In some cases, the target enzyme may have an activity localized to a hemorrhage site in a subject, such as an internal hemorrhage site in a subject or an external hemorrhage site in a subject. For example, the enzymatically-cleavable linking group may be configured such that it is specifically cleaved by one or more enzymes involved in the coagulation cascade, such as, but not limited to, thrombin (Factor IIa), Factor VIIa, Factor IXa, Factor Xa, FactorXIa, Factor XIa, Factor XIIa, Factor XIIIa, tissue plasminogen activator (tPA), urokinase plasminogen activator (uPA), activated protein C, plasmin, and the like.

In these embodiments, the corresponding protected hemostatic agent provides post administration-activated, controlled release of the hemostatic agent, because it requires enzymatic cleavage to initiate release of the hemostatic agent from the protecting group. In certain instances, the rate of release of the hemostatic agent depends upon the rate of enzymatic cleavage at the target site of action. Accordingly, the protected hemostatic agent can be configured such that it does not provide significant plasma levels of the active hemostatic agent and is not readily decomposed to afford the biologically active hemostatic agent other than by enzymatic cleavage at the target site of action.

The enzyme capable of cleaving the enzymatically-cleavable linking group may be a peptidase—the enzymatically-cleavable linking group being linked to the hemostatic agent through an amide (e.g., a peptide: —NHCO—) bond. In some embodiments, the enzyme is a peptidase such as those involved in the coagulation cascade. Examples include Factor Xa, FactorXIa, Factor VIIa, and thrombin, and the like.

The enzymatically-cleavable linking group attached to the hemostatic agent through an amide bond may be, for example, a residue of an amino acid or a peptide. The peptide may contain, for example, up to 10 amino acid residues. For example, it may be a dipeptide or tripeptide. In certain embodiments, each amino acid is an L-amino acid. Examples of naturally occurring amino acids are alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine. Accordingly, examples of enzymatically-cleavable linking groups include residues of the L-amino acids listed above and dipeptides and tripeptides, or longer peptides, formed from the L-amino acids listed above.

In certain embodiments, the enzymatically-cleavable linking group is attached to the nanoparticle, such as covalently bound to the nanoparticle. The enzymatically-cleavable linking group may be covalently bound to the surface of the nanoparticle using any of a variety of compounds typically used to functionalize the surface of molecules, such as, but not limited to, silanization reagents, such as an aminosilane, e.g., (3-aminopropyl)triethoxysilane (APTES), and the like. In certain embodiments, the ratio of silanization reagent (e.g., APTES) to nanoparticle is 1.5 µL/g or more, such as 1.6 µL/g or more, including 1.7 µL/g or more, or 1.8 µL/g or more, or 1.9 µL/g or more, or 2 µL/g or more. In some cases, the ratio of silanization reagent (e.g., APTES) to nanoparticle ranges from 1.5 µL/g to 2 µL/g, such as from 1.6 µL/g to 2 µL/g.

In certain embodiments, the hemostatic agent may include a specific binding agent. A specific binding agent can be any molecule that specifically binds to a protein or nucleic acid sequence or biomacromolecule that is being targeted (e.g., a target located at a target site of interest, such as a hemorrhage site). Depending on the nature of the target, a specific binding agent can be, but is not limited to, an antibody against an epitope of a peptide target, or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a peptide aptamer binding pair; and the like. For example, a specific binding agent may be a part of the protecting agent, which may be configured to bind to cells or surfaces in the blood, or vessel walls, or tissues, thereby altering the dispersement or concentration of the hemostatic agent in the subject. Affinity may be derived from groups within or attached to the protecting agent (e.g., on the end of PEG), or may be derived from the polyphosphate component, or a specific binding agent separate from the protecting agent (e.g., separately bound to the nanoparticle or the polyphosphate polymer).

Examples of a specific binding agent include, but are not limited to: a fibrin binding ligand (e.g., a fibrin binding peptide such as CREKA (SEQ ID NO: 2), a fibrin binding aptamer, a fibrin binding protein, a fibrin binding antibody, etc.); a collagen binding peptide (e.g., KLWVLPK (SEQ ID NO: 3)); an affinity ligand for activated platelets, thrombomodulin/thrombin complexes, specific endothelial cells (e.g., activatable peptide from thrombin-activatable fibrinolysis inhibitor (TAFI) (SEQ ID NO: 4), tissue factor, lipid membranes, and the like; an enzyme with an exposed fibrin binding motif; a ligand configured to form a covalent bond to fibrin (e.g., alpha2AP N-terminal peptide H-NQEQVSPLTGLK-NH$_2$ (SEQ ID NO: 5)); a thrombin binding ligand (e.g., a thrombin binding aptamer or peptide); antibody domains; inhibitors (e.g., peptides with a reactive ketone, etc.); combinations thereof, and the like.

Additional Agents for Use with the Hemostatic Agent in a Hemostatic Composition

The hemostatic agents disclosed herein can be provided alone as a hemostatic composition or can be provided in combination with one or more additional biologically active agents (e.g., hemostatic agents, antibiotics, ions (e.g., calcium, potassium, etc.) and the like) in a hemostatic composition. In general, optionally additional agents can include components which may be active or inert with respect to the activity of the hemostatic composition in promoting blood clotting, or may provide for an additional or different biological activity (e.g., antibacterial, anti-inflammatory, and the like). Such additional agent(s) can be provided in admixture (e.g., in dry or hydrated (e.g., solution)) with the hemostatic agent (e.g., in a slurry) or provided on the surface (e.g., for a non-porous hemostatic agent) or loaded into the hemostatic agent structure itself (e.g., for a porous hemostatic agent).

In some embodiments, the hemostatic composition includes an additional biologically active agent that can facilitate blood clotting, wound healing, and/or reduce the risk of infection. Such exemplary additional agents can include an agent with hemostatic activity, an antibiotic, a growth factor, a cytokine, and the like, which can promote wound healing and/or reduce the risk of infection. Such components can be from any suitable source, e.g., a recombinant source of the same or different animal origin as the subject to be treated (e.g., human, bovine, etc.). The hemostatic agent can be loaded with the biologically active agent to provide for biological activity as a varying weight percent of the hemostatic composition, e.g., 1% or more, 2% or more, 5% or more, 10% or more, 15% or more, 20% or more, 25% or more, or even greater weight percentages, depending on the biologically effective amount needed to produce the desired effect in the subject.

In some embodiments, the hemostatic composition includes a clot-promoting factor in addition to the hemostatic agent described herein. For example, the hemostatic composition can include a clotting factor or platelet activating agent. Exemplary agents include thrombin, Factor VII, Factor VIIa, serotonin, collagen, thromboxane A2, and ADP, combinations thereof, and the like. Such components can be from a recombinant source of the same or different animal origin as the subject to be treated (e.g., human, bovine, etc.).

In some embodiments, the hemostatic agent in the hemostatic composition is modified to include a bound biologically active agent, which may be a protein, an ion, or the like. Agents that have hemostatic activity are of interest. For example, a surface (e.g., external and/or internal surface) of the hemostatic agent may be modified to provide for a bound clot-promoting factor (e.g., thrombin, recombinant Factor VIIa, etc.), an antibiotic (e.g., silver ions), and the like. "Bound" as used in this context (which may be used interchangeably with the term "loaded") is meant to encompass covalent and non-covalent binding, including van der Waals forces, hydrogen bonds, chemisorption, physisorption, electrostatic forces, physical trapping within pores and/or channels of the hemostatic agent, and the like. Thus an agent that is "bound" to a surface of the hemostatic agent includes binding by absorption, adsorption, adhesion, covalent linkage, and the like.

Biologically active agent-loaded hemostatic agent can be produced by a variety of different methods. For example, the hemostatic agent can be soaked in a solution containing one or more agents of interest to provide for adsorption of the agent(s) onto a surface (e.g., external and/or internal surface) of the hemostatic agent. Following soaking for a desired period of time (e.g., to provide for a desired amount of agent loaded on and/or into the hemostatic agent), the biologically active agent-loaded hemostatic agent can then be washed to remove unbound material. The loaded hemostatic agent can then be dried or stored in hydrated or partially hydrated form, as may be desired according to the biologically active agent used.

In another example, the hemostatic agent can be heat treated to present a hydroxylated surface for condensation attachment of an oxo- or hydro-group expressing biologically active agents. This production method can provide for covalent binding of biologically active agent (e.g., protein, polyphosphate, silananizing agent, hydroxyl-PEG) to an external and/or internal surface of the hemostatic agent.

In another example, the surface of the hemostatic agent may be functionalized with, e.g., organosilanes, amino acids, carboxylic acids, esters and/or phosphate groups, to promote the non-covalent or covalent binding of an active agent. For example, the hemostatic agent can be functionalized with amine groups (e.g., primary, secondary or tertiary) to express a positive surface charge capable of electrostatically attracting negatively charged substituents in solution. Alternatively, the hemostatic agent can be functionalized with carboxylate groups to express a negative surface charge capable of electrostatically attracting positively charged substituents in solution. Other chemical groups that increase, decrease, or neutralize surface charge may be employed.

In another example, the oxide surface of the hemostatic agent can be functionalized with, e.g., organosilanes, amino acids, amines, carboxylic acids, and/or phosphate groups, to promote the attachment of biologically active materials. For example, silicon dioxide may express a negative surface charged when immersed in a solution with a pH greater than the isoelectric point of silicon dioxide. However, if silicon dioxide is first functionalized by attaching amine groups to the surface of silicon dioxide, the effective surface charge may be positive as a consequence of the positively charged amine groups on the periphery. Amine functionalized silica may electrostatically attract negatively charged substituents. Negatively charged silica, absent amine functional groups, may electrostatically repel negatively charged substituents.

Biologically active agents that find use in the hemostatic composition of the present disclosure, and which may used to provide a biologically active agent-loaded hemostatic agent can be selected from a variety of different active agents. Exemplary active agents include, but are not limited to, polypeptides (e.g., enzymes (including zymogens and activated enzymes), glycoproteins, peptides, and the like), phospholipids, ions, such as ions that act as cofactors in the clotting cascade (e.g., by serving as an ionic bridge) and/or ions that facilitate colloid precipitation (e.g., red blood cell precipitation), and/or ions that have antibiotic activity (e.g., silver ions), and the like), and other active agents that have a biological activity of interest (e.g., clot-promoting agents, antibiotics, anti-inflammatories, and the like). Where the active agent is a polypeptide or nucleic acid, the agent may be recombinant or synthetic (e.g., produced by non-genetic methods). Of interest are active agents that have activity in promoting blood clotting (e.g., thrombin) and/or antibacterial activity (e.g., silver ions). Biologically active agents, such as polypeptides, can be of any suitable origin, e.g., human, bovine, etc.

Exemplary biologically active polypeptide agents include, but are not limited to, prothrombin, thrombin, Factor VII, Factor VIIa, Factor X, Factor Xa, Factor XI, Factor XIa, Factor XII, Factor XIIa, Factor XIII, Factor XIIIa, fibrin, collagen, fibrinogen, growth factors (e.g., vascular endothelial growth factor (VEGF), epidermal growth factors, fibroblast growth factors, transforming growth factors, and the like), prekallikrein, high molecular weight-kininogen, protein concentrates (e.g., clotting factor concentrates (e.g., alphanate FVIII concentrate, bioclate FVIII concentrate, monoclate-P FVIII concentrate, haemate P FVIII, von Willebrand Factor concentrate, helixate FVIII concentrate, hemophil-M FVIII concentrate, humate-P FVIII concentrate, hyante-C™, Porcine FVIII concentrate, koate HP FVIII concentrate, kogenate FVIII concentrate, FVIII concentrate, mononine FIX concentrate, fibrogammin p FXIII concentrate, and the like), combinations thereof, and biologically active fragments thereof. It should be noted that the term "biologically active polypeptide agents" is meant to encompass active (e.g., processed) as well as activatable forms (e.g., zymogen) forms of polypeptides (e.g., where the polypeptides is an enzyme).

Exemplary ions that find use as a biologically active agent include, but are not necessarily limited to, $Ca^{2+}$, $Mg^{2+}$, $Ag^+$, $Na^+$, $K^+$, $Zn^{2+}$, $PO_4^{3-}$, $SO_4^{2-}$, $NO_3^-$, and the like. Such ions can be provided in the form of a salt, e.g., a salt-loaded hemostatic agent.

Exemplary salts that find use in the hemostatic compositions include, but are not limited to, aluminum sulfate, silver nitrate, calcium chloride, magnesium chloride, and the like. In certain embodiments, the hemostatic composition may include silver nitrate.

Exemplary anti-inflammatory agents that find use in the hemostatic compositions disclosed herein include, but are not necessarily limited to, leukocyte migration preventing agents, silver sulfadiazine, acetylsalicylic acid, indomethacin, nafazatrom, and the like.

Other biologically active agents that can find use in the hemostatic compositions disclosed herein include, but are not limited to, antibiotics (e.g., bacteriocides, bacteristatics, fungicides, antivirals, and the like). Examples of such active agents include, but are not limited to, $Ag^+$ ions, which may be provided as a silver salt, e.g. $AgNO_3$; β-lactams, cefoxitin, n-formamidoyl thienamycin, thienamycin derivatives, neomycin, metronidazole gramicidin, bacitracin, sulfonamides, aminoglycosides such as gentamycin, kanamycin, amikacin, sisomicin, or tobramycin, nalidixic acids and analogs such as norfloxican, combinations of fluoroalanine/pentizidone, nitrofurazones, combinations thereof, and the like. Such antibiotics are generally selected so as to be compatible with the site of delivery (e.g., type of hemorrhage site to be treated, the site of the wound, and the like), and the microbial infection to be prevented and/or treated.

Further exemplary biologically active agents may include analgesics, anesthetics, steroids, vasoconstrictors, lymphokines, cytokines, vitamins, and the like.

Hemostatic Compositions and Devices

As noted above, the hemostatic agent can be provided alone or in combination with one or more additional biologically active agents. Where the hemostatic composition is composed of a hemostatic agent with one or more additional biologically active agents, such hemostatic compositions may be provided in a variety of formats. For example, the biologically active agents of the hemostatic composition may be provided as a mixture (e.g., blended or admixed), may be provided as a coating on a substrate (e.g., where one or both of the biologically active agent and/or hemostatic agent is provided as a coating adhered to a substrate), or may be provided in a single package in the same or separate compartments of the package. The hemostatic agent and the additional biologically active agent(s) may also be provided in two or more packages that are to be opened and administered simultaneously (e.g., concurrently or consecutively) to a hemorrhage site.

In certain embodiments, the hemostatic composition includes a hemostatic agent, as described herein. In some instances, the hemostatic agent includes a nanoparticle and a polyphosphate polymer attached to the nanoparticle, as described herein. In some instances, the hemostatic agent includes a nanoparticle, a polyphosphate polymer attached to the nanoparticle, and a protecting agent attached to the nanoparticle or polyphosphate polymer by an enzymatically-cleavable linking group, as described herein. In some instances, the hemostatic composition includes a first hemostatic agent that includes a nanoparticle and a polyphosphate polymer attached to the nanoparticle, and a second hemostatic agent that includes a nanoparticle, a polyphosphate polymer attached to the nanoparticle, and a protecting agent attached to the nanoparticle or polyphosphate polymer by an enzymatically-cleavable linking group.

In general, a hemostatic composition can be provided as a sterile composition, and as such are generally provided in a sealed, sterile container which maintains the sterility of the hemostatic composition until use. Where desired, the container can further provide for maintenance of a hydration state of the hemostatic composition, e.g., through use of materials that provide a water vapor-resistant barrier (e.g., mylar, plastic, etc.). For example, the hemostatic composition can be provided in a sterile container in the form of a sealable mylar foil bag.

The hemostatic composition may further include fillers (e.g., aluminum sulfate) or thickening agents that facilitate the selective application of the hemostatic composition in various forms (e.g., as a paste, gel, powder, spray, aerosol, cement, or erodable (e.g., biodegradable) solid member). For example, in certain embodiments, the hemostatic composition may be configured for administration to an external hemorrhage site, and thus may be in various forms, such as a paste, gel, powder, spray, aerosol, cement, or erodible composition as described above. In other embodiments, the hemostatic agent may be configured for administration to an internal hemorrhage site. In these instances, the hemostatic composition may be administered in a form compatible to intravenous administration of the hemostatic composition, such as an aqueous, injectable formulation (e.g., a solution, a suspension, and the like).

Dosage Forms and Carriers

The hemostatic composition of the present disclosure can be provided in a variety of dosage forms, and, optionally, can be provided in combination with a variety of different, compatible carriers. Exemplary carriers include those which facilitate application to a hemorrhage site, such as an external wound, e.g., by facilitating delivery of the hemostatic composition from its packaging to a wound, facilitating application and/or maintenance at a wound site, and the like. Accordingly, the hemostatic composition, where compatible with the hemostatic activity of the hemostatic composition, can be provided as a dry formulation (e.g., a powder or other formulation that does not contain a liquid as a carrier), a paste, gel, or the like. In some embodiments, the hemostatic composition is provided as a dry, flowable dosage form that can be dispensed from a container (e.g., from a pouch or other sealed container). The hemostatic composition can also be provided in aerosol form, and thus can be provided in a sterile spray (e.g., which can be provided in combination with a propellant, or in a sprayable solution). Hemostatic compositions can be stored in a suitable sterile container, e.g., in a water vapor-resistant container, optionally under an air-tight and/or vacuum seal. In other embodiments, where the hemostatic composition is configured for administration to an internal hemorrhage site, the dosage form may include a carrier suitable for intravenous administration of the hemostatic composition, such as an aqueous solution, saline solution, buffer solution, blood substitute, and the like.

Hemostatic Devices

The hemostatic composition disclosed herein can be provided in connection with a device adapted for storage and/or delivery of a hemostatic composition to a hemorrhage site. As discussed above, the hemostatic composition is generally provided in a sterile container, which may further provide a water and/or vapor resistant barrier to prevent hydration of the hemostatic composition, as may be desired.

The container can be in the form of a pouch (e.g., a mylar pouch), canister, tube, or other container. The container can include a frangible portion to facilitate rapid opening of the container to provide for quick access to and delivery of the hemostatic composition contained therein. For solution-based formulations, the container may include a bag, pouch, vial, bottle, or other container suitable for containing a liquid formulation. For example, the container may include an IV bag configured for intravenous administration of the hemostatic composition, or a sealed vial from which a desired dose of the hemostatic composition may be withdrawn, e.g., via a syringe, for administration to the subject.

The hemostatic composition can be provided in conjunction with a variety of different devices, which can be adapted to facilitate administration of the hemostatic composition to a hemorrhage site. For example, the hemostatic composition can be packaged in the same or separate container with one or more of a sterile sponge, gauze, bandage, swab, spray, aerosol, gel, cement, compression bandage, pillow (e.g., to facilitate application to a head wound), sleeve (e.g., for covering a wound on a limb), and the like. In some embodiments, the device serves as a substrate for the hemostatic composition, where the hemostatic agent in the hemostatic composition can be adhered to the device. For example, the hemostatic composition can be provided on a blood-accessible surface of the device (e.g., as a surface coating), and/or within the device (e.g., permeating at least a portion of an absorbent material, such as gauze). It is to be understood that a "coating" is at least on the surface of the substrate to which it is applied, and may permeate beyond the surface, such as where the substrate is an absorbent material.

Where the hemostatic composition contains the hemostatic agent and one or more additional biologically active agent, the hemostatic agent and other agent(s) may be present as a loose mixture (e.g., as in a pouch to be opened prior to use). In certain embodiments, one or more biologically active agents are loaded on a hemostatic agent in the hemostatic composition. In other embodiments, the hemostatic composition is provided as a coating on a substrate, where the hemostatic agent may be optionally loaded with a biologically active agent (e.g., thrombin). Alternatively or in addition, the hemostatic agent may be provided as a coating on a substrate (e.g., bandage or sponge) and a second biologically active agent may be provided loose and in the same sealed packaging as the substrate.

Where the hemostatic composition is configured for administration to an internal hemorrhage site, the hemostatic composition may include the hemostatic agent and one or more additional biologically active agents, where the hemostatic agent and other agent(s) may be present in the same solution (or suspension). In certain embodiments, one or more biologically active agents are loaded on a hemostatic agent in the hemostatic composition, and thus may be provided in a single solution (or suspension). In other embodiments, the other active agent(s) may be provided in separate containers from the hemostatic composition and may be administered simultaneously (e.g., concurrently or consecutively) to the subject.

Methods of Use of Hemostatic Compositions and Devices

The hemostatic compositions disclosed herein can be used to facilitate clotting of an internal or external bleeding wound. As such, the hemostatic compositions can be used to enhance blood clotting at a hemorrhage site of a subject in need thereof, and at least temporarily stabilize a wound (e.g., at least temporarily stabilize a patient that might otherwise have died as a result of exsanguinations). Such methods generally involve contacting a hemostatic composition disclosed herein to a bleeding external or internal wound of a subject for a time sufficient to promote blood clot formation. As such, the method may include administering to a hemorrhage site in a subject the hemostatic composition as described herein for a period of time sufficient to at least initiate blood clotting at the hemorrhage site.

The hemostatic composition can be contacted with a wound that is externally accessible by, for example, accessing the wound and pouring the hemostatic composition onto the wound. Alternatively or in addition, the hemostatic composition can be delivered to an external wound by applying a hemostatic device to the wound, where the device includes a hemostatic composition coated on a substrate. Contact can be maintained through application of pressure, and may be held in place either by hand and/or through use of a bandage. Contact may be maintained at least until blood flow from the wound has slowed or has detectably ceased, i.e., until the wound is stabilized through formation of a clot. Once the clot is formed, the hemostatic composition can be removed from the wound. Where necessary, the wound can be irrigated to remove any loose hemostatic agent in the wound.

Where the hemostatic composition is configured for administration to an internal hemorrhage site, the method may include intravenously administering the hemostatic composition to the subject. As such, the method may include locating an appropriate intravenous site on the subject and injecting the hemostatic composition into the subject at the intravenous site. In certain embodiments, as described herein, the hemostatic agent may include a protecting agent that is configured to reduce or inhibit the hemostatic activity of the hemostatic agent. Upon injection of the protected hemostatic agent into the subject, the hemostatic agent may circulate through the body of the subject until activated at a target site (e.g., a target internal hemorrhage site). As described above, the protecting agent may be removed from the hemostatic agent through cleavage of a cleavable linking group by an enzyme localized at the target site, thus restoring the hemostatic activity of the hemostatic agent at the desired target site. In certain embodiments, the protecting agent is not significantly removed at other non-specific sites in the subject, such that the protected hemostatic agent does not have detectable non-specific hemostatic activity at other sites in the subject, and thus only has detectable hemostatic activity when specifically activated at the desired target site (e.g., the desired target internal hemorrhage site).

These methods are applicable to a variety of different types of wounds, which may have been inflicted intentionally or through accident and at any portion of the body amenable to application of a hemostatic composition disclosed herein. The hemostatic composition finds use in wounds of all degrees of severity ranging from bleeding skin surface wounds to wounds involving laceration of the femoral artery or other major artery or vein.

Subjects include any subject in need of treatment at an external or internal hemorrhage site, and can include both human and veterinary applications (e.g., mammals such as dogs, cats, livestock (e.g., cattle, horses, sheep, goats, etc.), and the like).

Utility

The subject hemostatic compositions, devices and methods find use in a variety of different applications where the treatment of an external or internal hemorrhage site in a subject is desired. In some instances, the wound may be an external hemorrhage site. In other embodiments, the wound may be an internal hemorrhage site. In some instances, the wound may include both external and internal hemorrhage sites. The wound may be a surgical wound or a trauma wound, such as, but not limited to, a surgical or traumatic soft tissue wound.

As described herein, the subject hemostatic compositions, devices and methods find use in promoting blood clotting at a hemorrhage site, whether an external or internal hemorrhage site. In certain embodiments, the subject hemostatic compositions, devices and methods find use in promoting blood clotting at a hemorrhage site under conditions of coagulopathy. By "coagulopathy" is meant a condition where clot formation in a subject is impaired, such as a condition where the subject's coagulation cascade is impaired. Coagulopathy may include one or more of a subset of conditions, such as dilution, hypothermia and acidosis. As such, the subject hemostatic compositions, devices and methods find use in promoting blood clotting at a hemorrhage site when a subject's coagulation cascade is impaired, such as under one or more coagulopathy conditions, such as dilution, hypothermia and acidosis.

For example, the subject hemostatic compositions, devices and methods find use in promoting blood clotting at a hemorrhage site under a dilution condition, e.g., the subject hemostatic compositions, devices and methods are hemostatically effective even when the concentration of procoagulant factors at the hemorrhage site is insufficient to have a significant hemostatic effect, as may occur as the result of trauma and/or loss of blood. Similarly, in certain embodiments, the subject hemostatic compositions, devices and methods find use in promoting blood clotting at a hemorrhage site under a condition of hypothermia, e.g., the subject hemostatic compositions, devices and methods are hemostatically effective even when the subject's body temperature drops below 37° C., as may occur as the result of trauma and/or loss of blood. In addition, in some embodiments, the subject hemostatic compositions, devices and methods find use in promoting blood clotting at a hemorrhage site under a condition of acidosis, e.g., the subject hemostatic compositions, devices and methods are hemostatically effective even when the pH of blood is below its typical value of pH 7.4, as may occur as the result of trauma. In certain embodiments, the subject hemostatic compositions, devices and methods find use in promoting blood clotting at a hemorrhage site under one, or a combination of two or more, coagulopathy conditions.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric.

Example 1

Materials

Ethanol (99%), tetraorthoxilicate (TEOS), ammonia $NH_4OH$ (28%), (3-aminopropyl)triethoxysilane (APTES) were supplied by Sigma Aldrich. Deionized water was obtained using a Milli-Q water purification system. Frozen pooled normal plasma (PNP) and Factor XII-deficient plasma were purchased from George King Biomedical (Overland Park, KS) and handled according to package inserts. Phospholipid solutions in chloroform were purchased in Avanti Polar Lipids: L-alpha-phosphatidycholine (PC) and L-alpha-phosphatidylserine (PS). Sodium chloride, potassium chloride, sodium phosphate, dibasic and potassium phosphate—for Phosphate Buffer Saline (PBS), were supplied by Sigma Aldrich.

Synthesis of Silica Nanoparticles

Silica nanoparticles (SNP) were synthesized following a modified Stober method. (W. Stöber, A. Fink, E. Bohn, Controlled growth of monodisperse silica spheres in the micron size range, Journal of Colloid and Interface Science. 26 (1968) 62-69). For the synthesis of silica nanoparticles, tetraethoxysilane (TEOS) and ammonia were added dropwise and consecutively into 57 mL of ethanol while stirring at 300 rpm at room temperature. The stirring was continued for 24 h. pH and particle size was measured after synthesis. The material was recovered by centrifugation (14 k, 30 min), washed with ethanol to remove ammonia and unreacted TEOS (3 times). After redispersing the material in ethanol by sonication (FS20 Fisher Scientific), the products were dried overnight at 60° C. and once homogenized, calcined at 550° C. during 4 h. Different amounts of TEOS (0.5-4 mL) and ammonia (0.5-4 mL) were used to produce different particle sizes.

Figure 2:
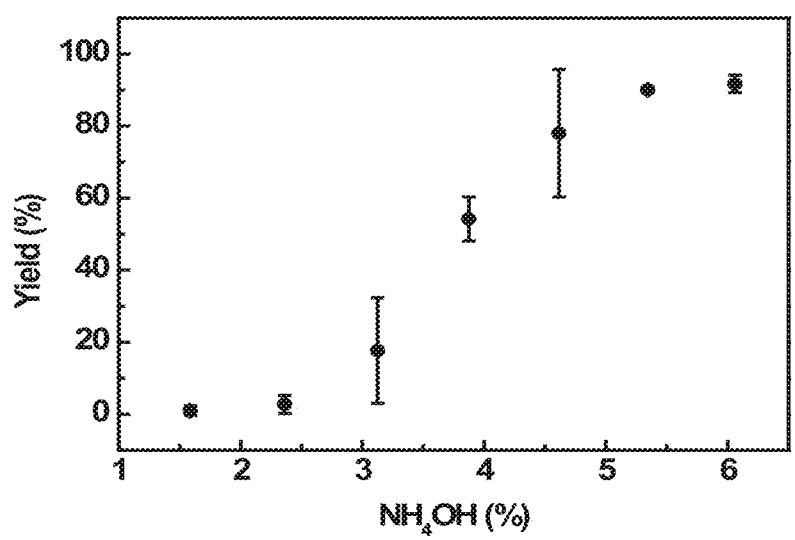
FIG. 2 shows a graph of the yield (%) vs. amount of $NH_4OH$ (%) added to a reaction to produce silica nanoparticles, according to embodiments of the present disclosure.

Particles above 10 nm were synthesized following the modified Stöber method and recovered using centrifugation as described above. Different nanoparticle sizes were obtained by varying the amounts of TEOS and ammonia ($NH_4OH$). FIG. 1 shows a graph of average particle size (nm) of the silica nanoparticles vs. amount of $NH_4OH$ (%) added to the reaction. The average size increased as the amount of $NH_4OH$ added increased. Sigma Aldrich supplied Ludox silica nanoparticles for nanoparticles with average sizes below 10 nm. Silica nanoparticles below 50 nm were isolated by ultrafiltration and ultracentrifugation to provide a stock for coagulation and functionalization experiments. FIG. 2 shows a graph of the yield (%) of silica nanoparticles vs. amount of $NH_4OH$ (%) added to the reaction. The yield increased significantly for $NH_4OH$ of 4% or more. Syntheses below 4% $NH_4OH$ produced a yield below 40%. In some instances, a low amount of ammonia may slow catalysis of the TEOS hydrolysis reaction.

Preparation of Polyphosphate Polymer

Medium chain polyphosphate (30-130mer, "P70" was purified from commercially available industrial source phosphate glass ("P70", BK Guilini GMBh, Germany). Long chain polyphosphate ("P700"), was solubilized from phosphate glass, practical grade, water insoluble (Sigma Aldrich) in 250 mM LiCl+50 mM LiOH, pH 10.5 at 100° C. The material was then precipitated with 50 mM NaCl in 2 times the volume of isopropanol, and resuspended in double distilled $H_2O$.

Two different sizes of polyphosphate polymer were used: P70, with an average chain length of 70 monomers, and P700, with a size range between 200 and 1300 monomers and a peak concentration at about 700 monomers.

Synthesis Silica-Polyphosphate Nanoparticles

The synthesized polyphosphate was used to functionalize the silica nanoparticles. The silica nanoparticles were dispersed by sonication in Milli-Q water and placed at 30° C. Then polyphosphate was added under vigorous stirring. The stirring was continued for 12 h. The functionalized nanoparticles were recovered after two centrifugation steps (14 k, 30 min), washing with ethanol, redispersing by sonication in ethanol and finally drying overnight at 60° C. Successful functionalization of the nanoparticles was identified using a dynamic light scattering (DLS) instrument.

Characterization of the Nanoparticles

Zeta Potential and Particle Size Determination

Zeta potential and particle size were measured by laser diffractometry using a Zetasizer Nano ZS instrument (ZEN 3600, Malvern Instruments) at 20° C. with an incident wavelength of 633 nm and 1730 backscattering angle. Zeta potential was measured in water at different pH and in PBS buffer (137 mM NaCl, 2.7 mM KCl, 12 mM phosphate). Disposable cells were cleaned with ethanol and water prior to sample loading. Particle size was measured just after the particles were synthesized (with ethanol as a solvent) and after the calcination step, redispersed by sonication in water at 1 mg/mL. Disposable cells were cleaned with each respective solvent before sample loading.

Zeta potential tests showed that SNPs had a negative charge in simulated body fluid, which may facilitate activation of the intrinsic pathway by activating Factor XII. Zeta potential exhibited no systematic change in coagulation with respect to size or pH.

Figure 97:
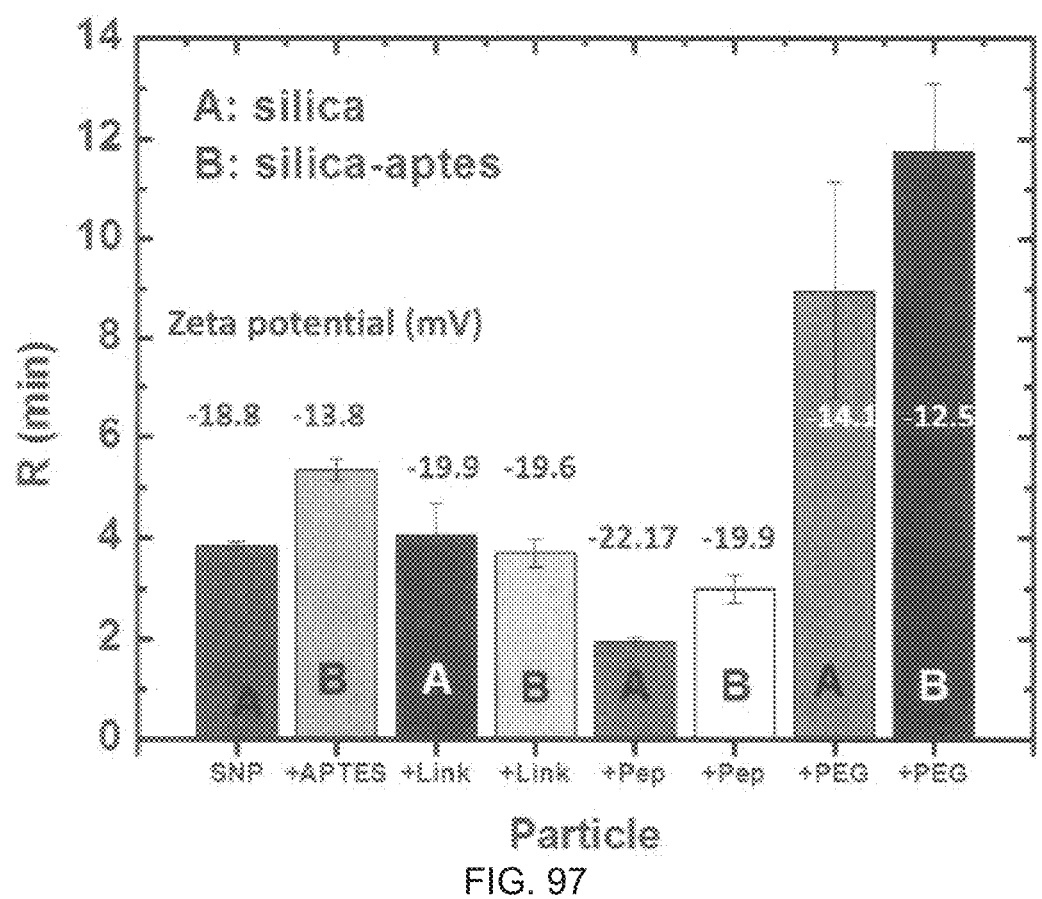
FIG. 97 shows a graph of clotting times for various SNPs, according to embodiments of the present disclosure.
Figure 98:
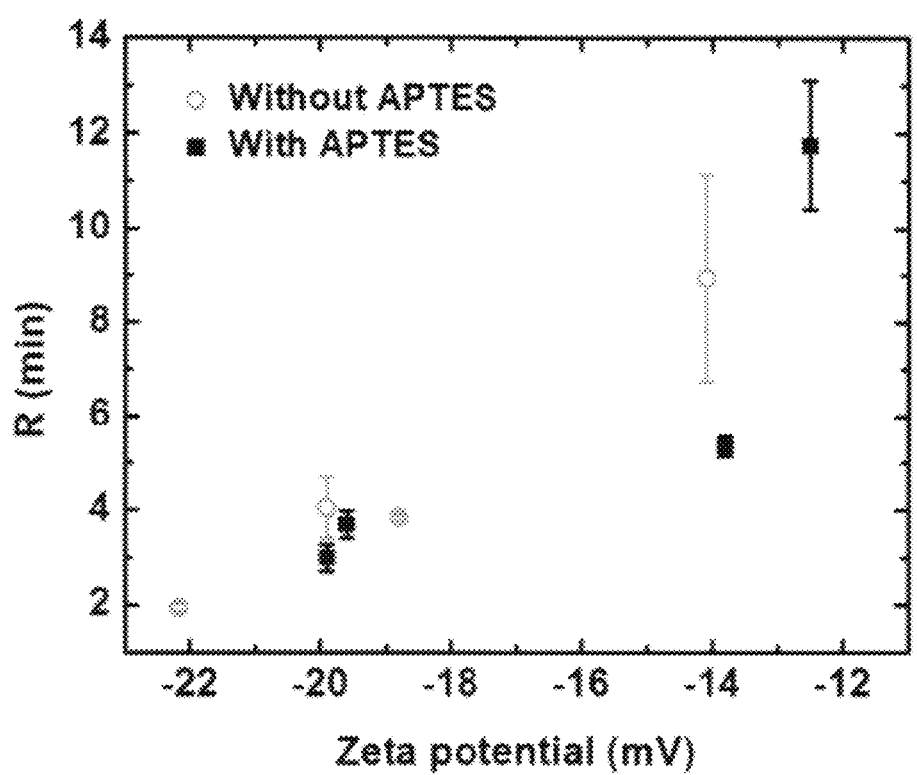
FIG. 98 shows a graph of the relationship between zeta potential and clotting time for SNP with and without APTES, according to embodiments of the present disclosure.

FIG. 97 shows a graph of clotting times for various SNPs (e.g., SNP, SNP+APTES, SNP+linker, SNP+APTES+linker; SNP+peptide, SNP+APTES+peptide, SNP+PEG, and SNP+APTES+PEG; see examples below for a description of the linker and peptide). Zeta potentials for each type of particle are also indicated on the graph. SNP+PEG and SNP+APTES+PEG had zeta potentials that were less negative than other particles, which corresponded to longer clotting times, R. The relationship between zeta potential and clotting time for SNP with and without 3-aminopropyltriethoxysilane (APTES) is shown in FIG. 98.

Figure 99:
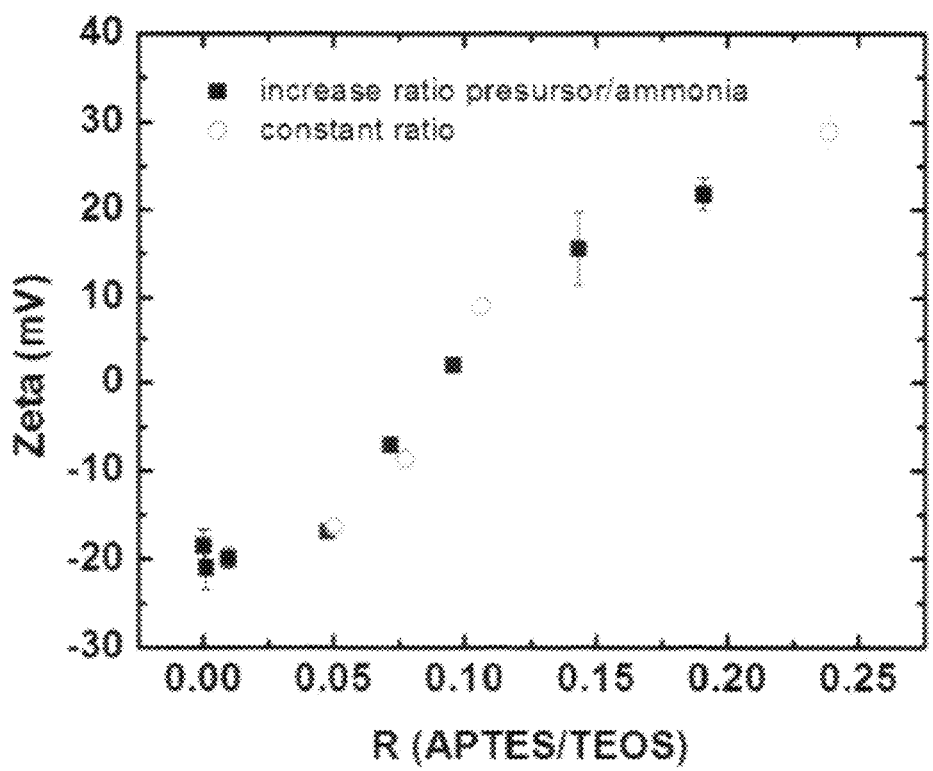
FIG. 99 shows a graph of zeta potential vs. the ratio of APTES/TEOS used in the synthesis of SNPs, according to embodiments of the present disclosure.
Figure 100:
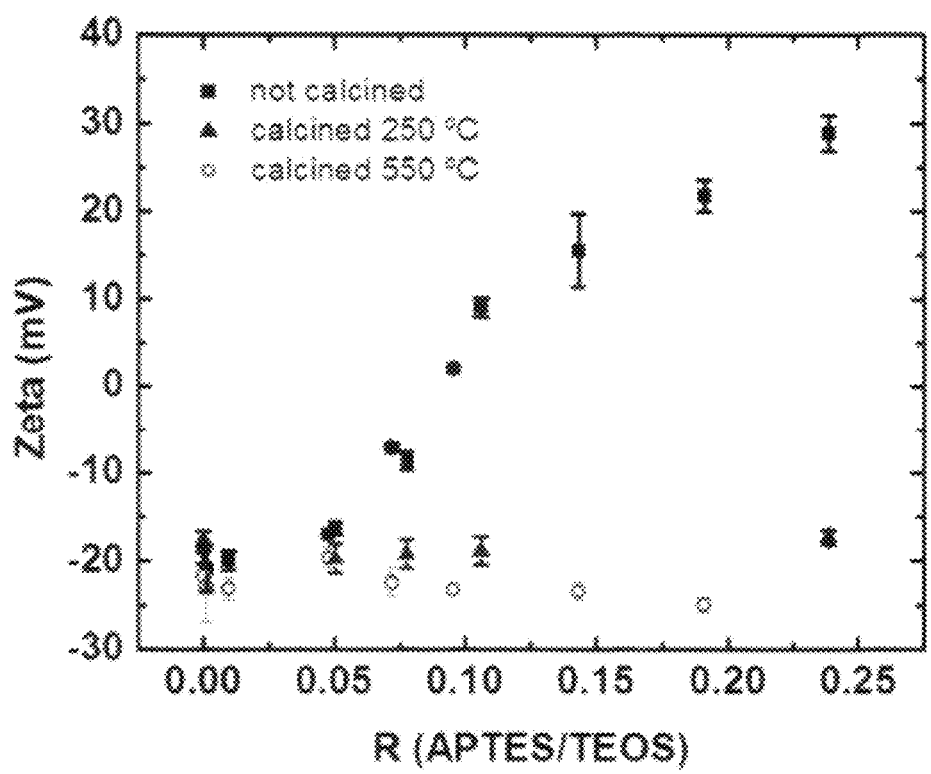
FIG. 100 shows a graph of zeta potential vs. the ratio of APTES/TEOS for calcined and not calcined SNPs, according to embodiments of the present disclosure.
Figure 101:
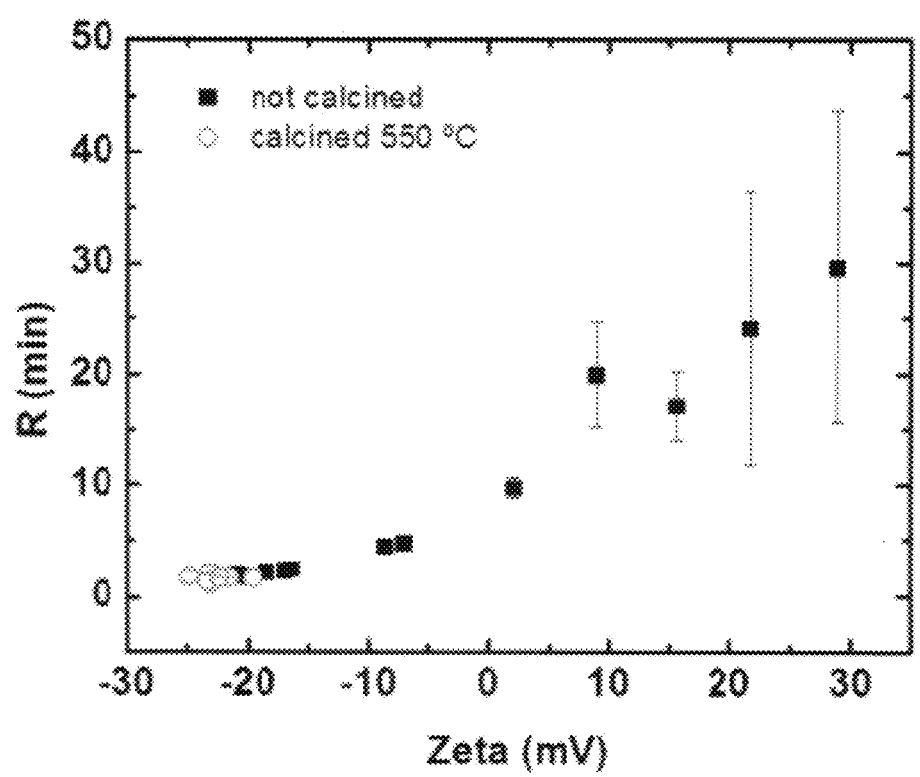
FIG. 101 shows a graph of clotting time vs. zeta potential for calcined and not calcined SNPs, according to embodiments of the present disclosure.

FIG. 99 shows a graph of zeta potential vs. the ratio of APTES/TEOS used in the synthesis of SNPs. A more positive zeta potential indicated the presence of amino groups on the particle surface. FIG. 100 shows a graph of zeta potential vs. the ratio of APTES/TEOS for calcined and not calcined SNPs. With calcination, the amino group decomposed and the zeta potential was more negative. FIG. 101 shows a graph of clotting time vs. zeta potential for calcined and not calcined SNPs. A negative zeta potential produced a lower clotting time.

Morphology and Structure of the Particles

The morphology, structure and particle size of the nanoparticles were determined via transmission electron microscopy (TEM). TEM micrographs were obtained on a FEI Tecnai G2 Sphera electron microscope with an accelerating voltage of 200 kV.

Figure 4:
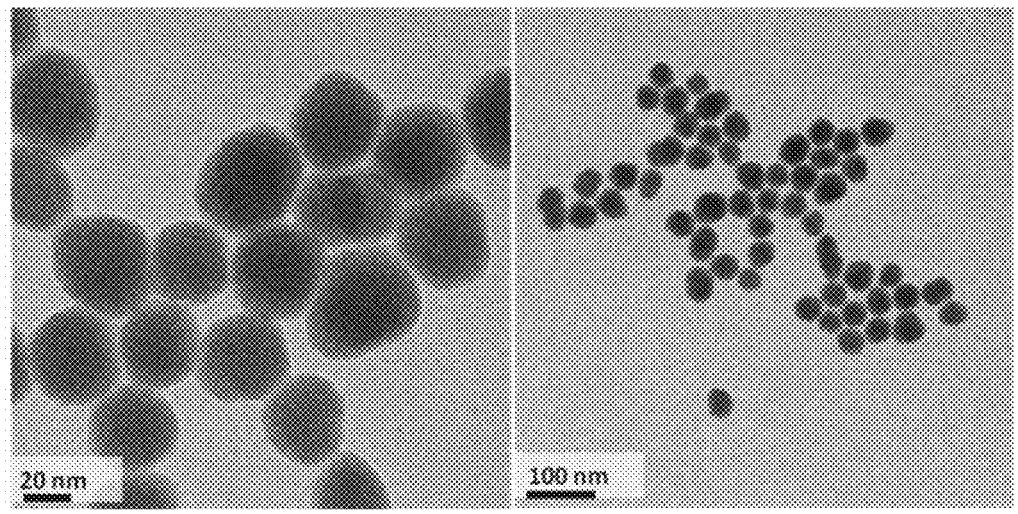
FIG. 4 shows TEM micrographs of silica nanoparticles of 55 nm average size, according to embodiments of the present disclosure.

P70 directly adsorbed to silica was found to only slightly increase the particle size (by several nm). FIG. 4 shows TEM micrographs of silica nanoparticles of 55 nm average size.

Quantification of the Polyphosphate

The polyphosphate content on the particles was quantified by hydrolysis to monophosphate using calf intestinal alkaline phosphatase, followed by phosphate analysis using a malachite green assay.

Determination of Clotting Activity

The clotting activity was determined by two different methods: standard coagulometry and rotational thromboelastometry (TEG) in a thrombelastograph (TEG® 5000, Haemonetics). These tests measure several parameters that are relevant to coagulation, such as initial time for clot formation (R, min), rate of clot formation (a, deg), time until clot reaches 20 mm (K, min) and clot strength or maximum amplitude (MA, mm). For the tests, the particles were dispersed in HBS containing phospholipid vesicles and sonicated. The phospholipids were 80% phosphatidylcholine (PC) and 20% phosphatidylserine (PS) and were prepared by sonication from the commercial solutions in chloroform. The subsequent dilutions were made by diluting the stock dispersion in this same solvent.

For the coagulometry tests, 50 µL of the particles were placed into a pre-warmed coagulometer cuvette followed by 50 µL of pooled normal plasma (PNP). After incubating for 33 minutes at 37° C., to activate the contact pathway and allow the mixture to reach the proper temperature, 50 µL of pre-warmed 25 mM CaCl2) was added into the cuvette. The results were the average values of duplicate tests.

In the TEG tests, first 340 µL of pooled normal plasma (PNP) and 10 µL of the clotting agent were added in the TEG cup and incubated at 37° C. After 3 minutes, 20 µL of 0.2 M CaCl2) was added to the cup and the test was started immediately after. The results shown were the average value of, typically, 4 to 6 replicates. Concentration- and size-dependent analyses were done.

Results and Discussion

Experiments were performed with silica nanoparticles (SNPs) and polyphosphate-functionalized silica nanoparticles (SNP—P70) to measure the effect of the silica particles' size and concentration on coagulation. Clotting experiments compared the silica particles at either a fixed concentration of 0.68 mg/mL (25 mg/mL stock solution) or at a fixed size of 55 nm to determine high activity range boundaries. Each particle formed an initial clot (R) between 3 and 5 min. The threshold for minimum R value occurred at a particle size of ~30 nm. Experiments in which particles below 20 nm were synthesized exhibited a bimodal size distribution when measured using DLS, which may be attributed to an amount of ammonia that was too low for the catalysis of the TEOS hydrolysis reaction.

Figure 3:
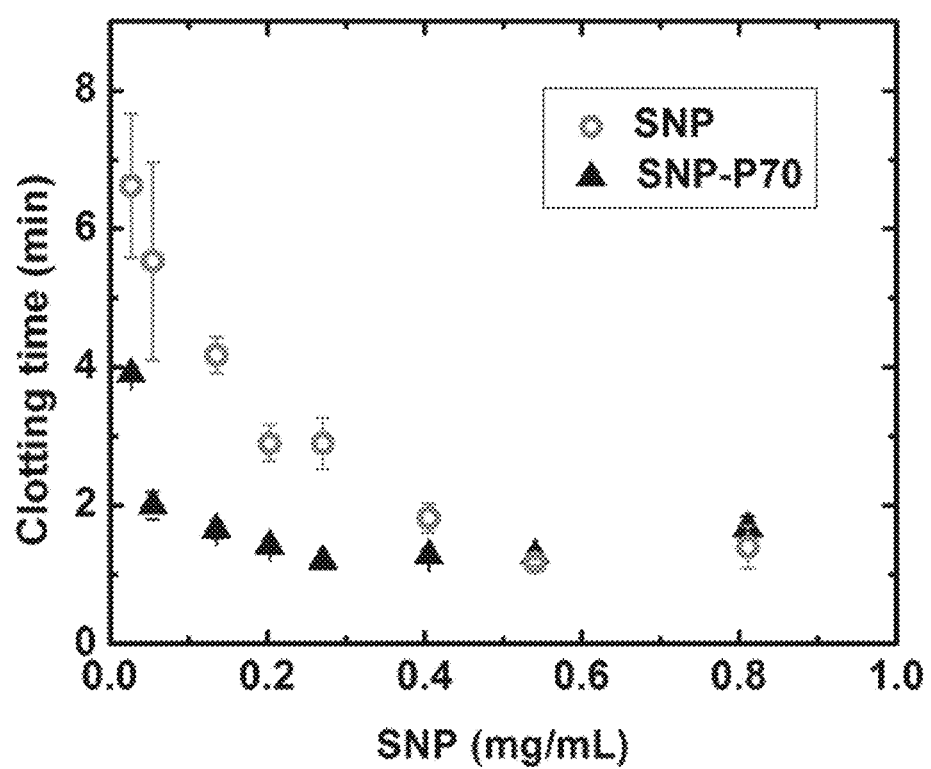
FIG. 3 shows a graph of R value (min) vs. concentration (mg/mL) of silica nanoparticles (SNP) and silica nanoparticles functionalized with polyphosphate polymer (SNP—P70) (70 monomer chain length) at 37° C. and 10.8 mM $Ca^{2+}$, according to embodiments of the present disclosure.

TEG experiments were performed to determine clotting time, R, vs. concentration (mg/mL) of silica nanoparticles (SNP) and silica nanoparticles functionalized with polyphosphate polymer (SNP—P70) (70 monomer chain length) at 37° C. and 10.8 mM Ca2+. As shown in FIG. 3, the concentration dependence of R for SNP and SNP—P70 was examined. P70 was a polyphosphate chain that was approximately 70 monomers in length. At low particle concentrations, the R value was relatively high (e.g., clotting time was long). As the particle concentration increased, R decreased until a minimum R value was obtained. For bare (i.e., unfunctionalized) silica, the minimum R value occurred at 0.54 mg/ml. SNP—P70 reached a minimum R value at a concentration of 0.27 mg/ml, half that of bare SNP. SNP—P70 also improved clotting time when compared to P70 added directly to plasma.

Figure 5:
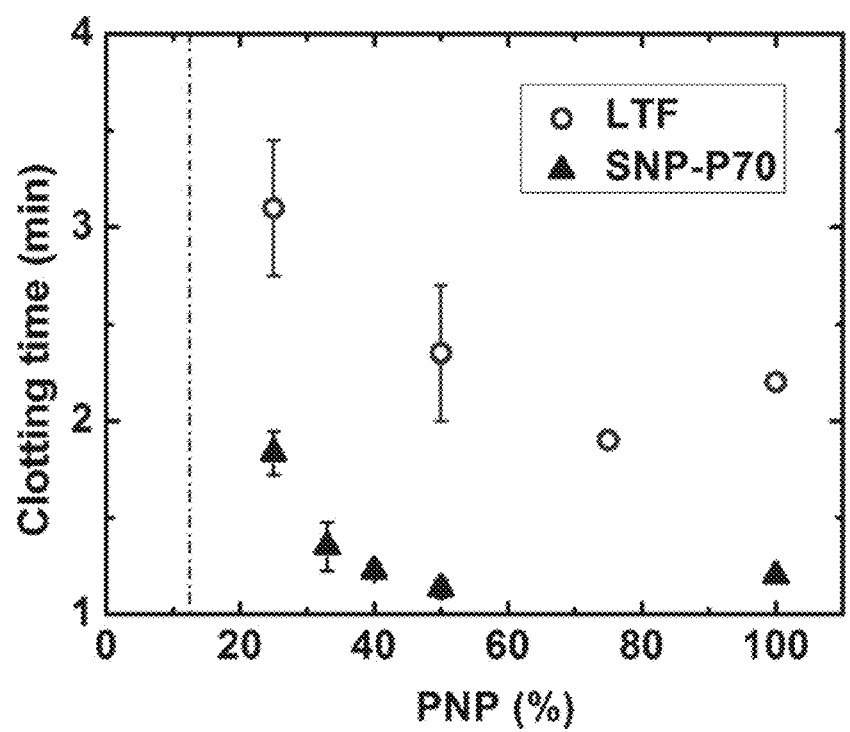
FIG. 5 shows a graph of clotting time, R, for SNP—P70 and lipidated tissue factor (LTF) at various dilutions of pooled normal plasma (PNP) at 37° C. and 10.8 mM $Ca^{2+}$, according to embodiments of the present disclosure.

TEG experiments were performed to determine clotting time, R, for SNP—P70 and lipidated tissue factor (LTF), a protein initiator of the extrinsic pathway, at various dilutions of pooled normal plasma (PNP) at 37° C. and 10.8 mM $Ca^{2+}$. The concentration of LTF used was 0.5 ng/mL and the concentration of SNP—P70 used was 0.27 mg/mL. As shown in FIG. 5, when compared with LTF, SNP—P70 induced rapid coagulation even under conditions of hemodilution.

Figure 6:
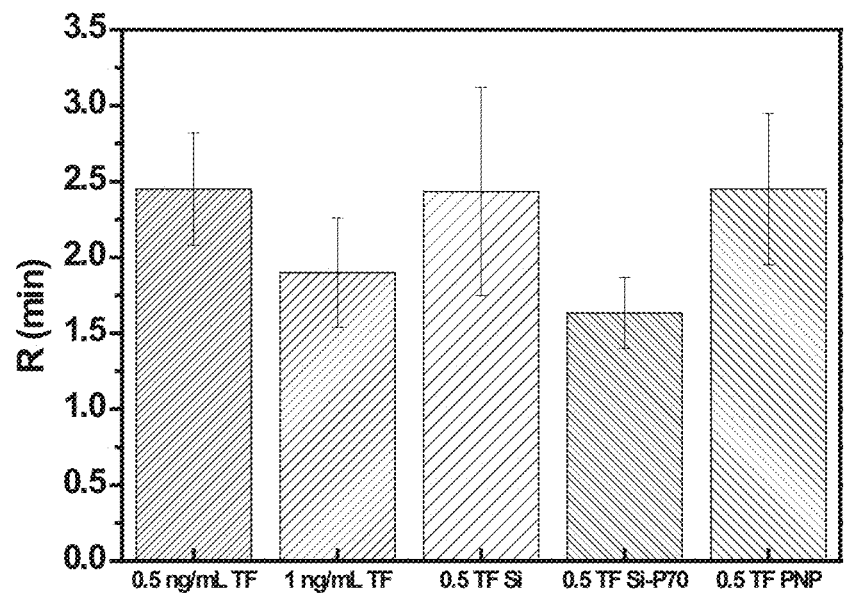
FIG. 6 shows a graph of clotting time (R) for various conditions using FXII deficient plasma, according to embodiments of the present disclosure. SNP—P70 showed the smallest and most consistent R value. The last bar in the graph was a control using lipidated tissue factor (LTF) in pooled normal plasma (PNP).
Figure 7:
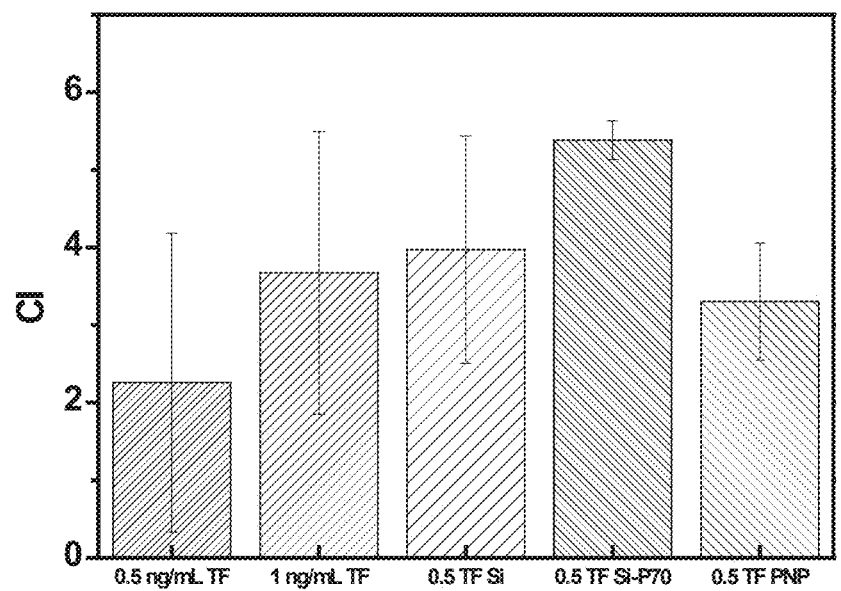
FIG. 7 shows a graph of coagulation index (CI) for various conditions using FXII deficient plasma (higher index indicates increased clotting), according to embodiments of the present disclosure. SNP—P70 had the highest and most consistent CI value. The last bar in the graph was a control using lipidated tissue factor (LTF) in pooled normal plasma (PNP).

Experiments were performed to determine the mechanism by which P70-bound nanoparticles induce clotting by determining clotting times using FXII deficient plasma (FIGS. 6 and 7). As they activate clotting through FXII activation and the intrinsic pathway, the bare nanoparticles cold not induce clotting. With the intrinsic pathway blocked, coagulation only occurred through the addition of tissue factor (TF) and the extrinsic pathway. Since P70 accelerated coagulation through FXa, a combination of TF and P70-bound silica improved clotting. Various mixtures of TF and nanoparticles were tested. The two lowest clotting times (R) occurred as a result of either 1 ng/mL TF or 0.5 ng/mL TF mixed with 0.676 mg/mL SNP—P70 (FIG. 6). Although the two conditions shared a similar clotting time, the P70-bound silica rapidly accelerated clot growth as shown by the significantly larger coagulation index (CI) score (FIG. 7). The P70-bound silica also exhibited the best reproducibility of all the conditions, which may facilitate a reduction in adverse side-effects. The tissue factor formed a small clot upon addition to plasma, but the clot grew at a slow rate. These tests showed that the P70 bound particles increased clotting through mediating FXa and thrombin, which may facilitate treating hemorrhage.

Figure 8:
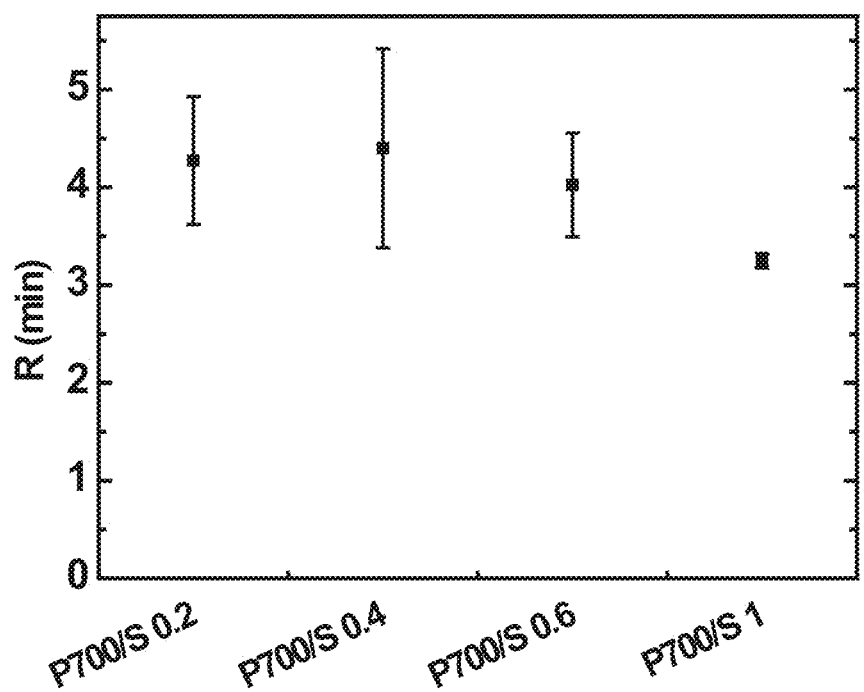
FIG. 8 shows a graph of clotting time, R, for various different polyphosphate (P700) to SNP ratios (0.2, 0.4, 0.6, and 1), according to embodiments of the present disclosure.

Experiments were performed to determine clotting time, R, for various different polyphosphate to SNP ratios. Polyphosphate that included about 700 monomer polyphosphate (P700) was used in the experiments. Polyphosphate with a size range above 500mers was shown to accelerate the contact or intrinsic pathway by activating FXII. The P700 was attached to the SNP using the same methods described above. Four different ratios of P700:SNP were tested –0.2, 0.4, 0.6, and 1. Similar to P70, clotting assays showed that clot time decreased with a ratio of P700:SNP above 0.5. As shown in FIG. 8, a 1:1 ratio of P700:SNP minimized clot time.

Experiments were performed to determine the effect the amount of polyphosphate in the functionalized SNP had on coagulation. 200-mg samples of SNP, SNP—P70, and SNP—P700 nanoparticles were tested for polyphosphate quantification and coagulation tests. These tests showed that SNP—P70 particles with a concentration of 25 nmol $PO_4$/mg SNP (quantified by hydrolysis) exhibited higher procoagulant activity than SNP—P70 particles with a higher nmol $PO_4$/mg SNP concentration.

Figure 9:
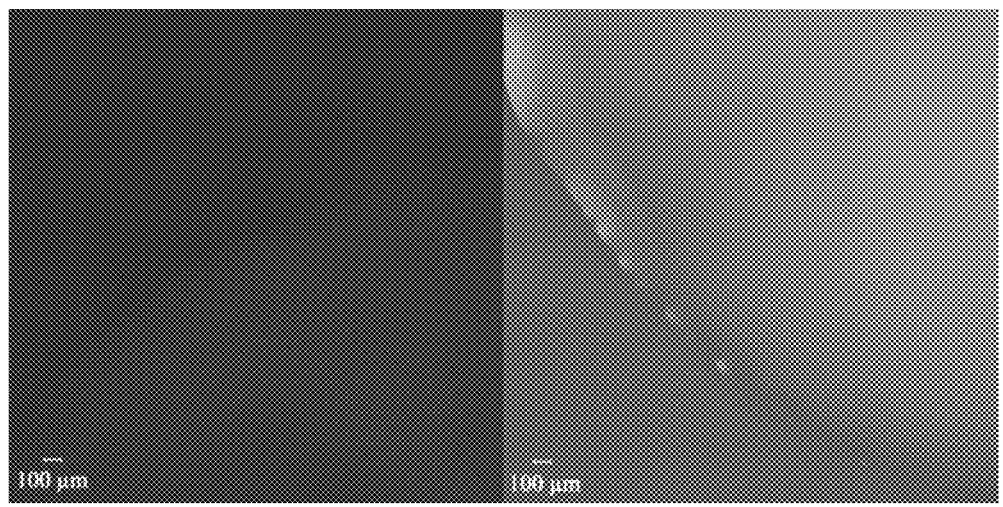
FIG. 9 shows fluorescence microscope images of a thrombin-specific blue coumarin dye experiment to qualitatively determine the coagulation threshold response, according to embodiments of the present disclosure.

In addition to TEG, the coagulation threshold response was also observed using a thrombin-specific blue coumarin dye. These experiments used a method developed by the Ismagilov group (Kastrup, C J, Shen, F, Runyon, M K, et al. (2007). Characterization of the threshold response of initiation of blood clotting to stimulus patch size. *Biophysical Journal*, 93(8), 2969-77). A small concentration of dye was added to recalcified plasma. As clotting progressed and thrombin was produced, the thrombin cleaved the coumarin dye which caused the solution to fluoresce. Signified by rapid fluorescence, the thrombin burst quickly led to clot formation. A fluorescence microscope captured the qualitative change as shown in FIG. 9.

Figure 10A:
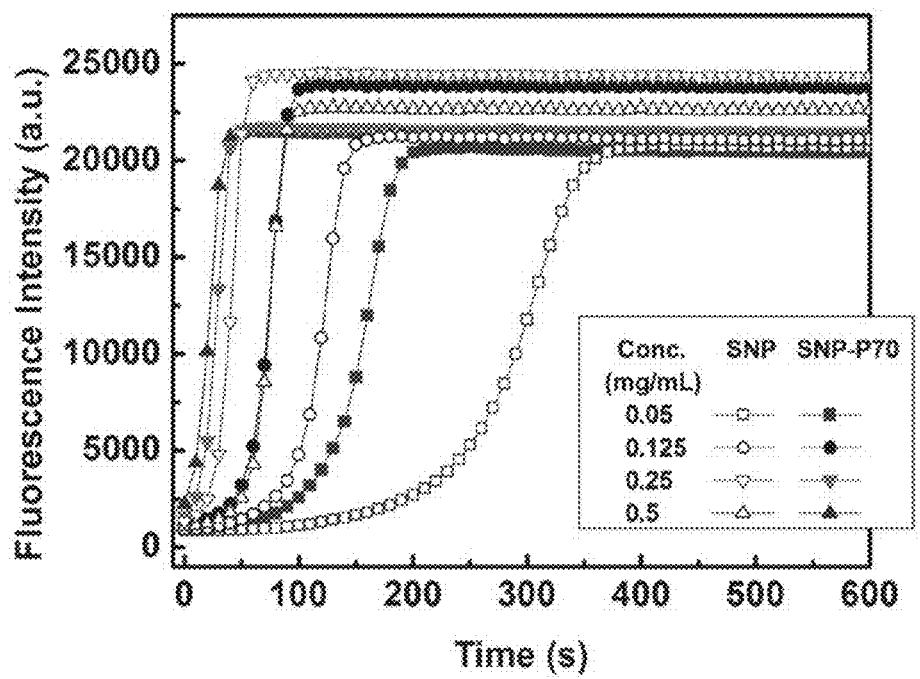
FIGS. 10A and 10B show a graph of fluorescence intensity (a.u.) vs. time for various concentrations of SNP and SNP—P70 (see FIG. 10A), and a graph of clot time (half-time, s) vs. concentration (mg/mL) for SNP and SNP—P70 (see FIG. 10B), according to embodiments of the present disclosure.
Figure 10B:
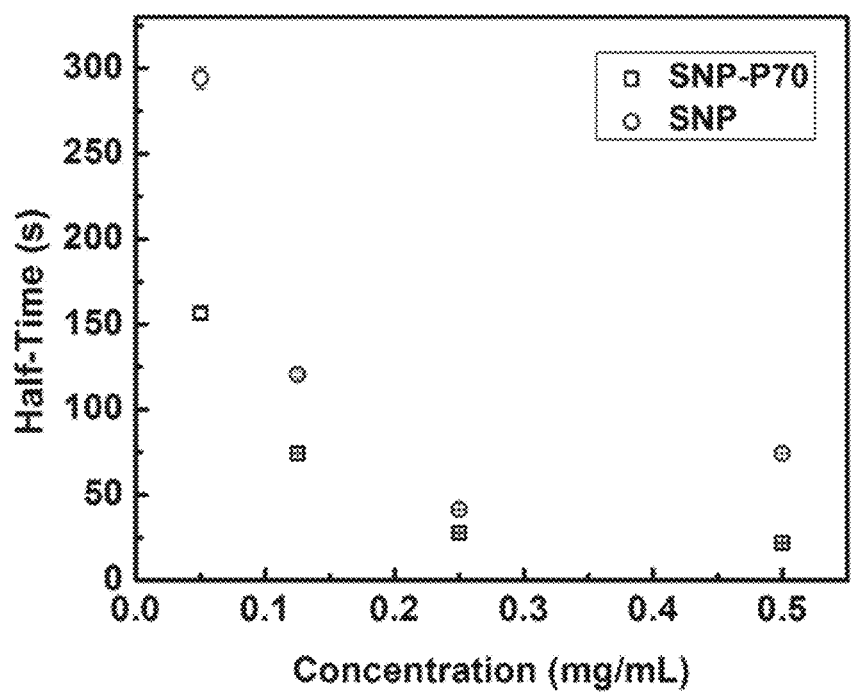

Thrombin generation was also monitored using a plate reader. By reading fluorescence every 10 seconds, the thrombin burst was identified. As clotting occurred near the rapid rise section of the thrombin burst, the clot time was determined from the fluorescence data plot. FIG. 10 shows a graph of fluorescence intensity (a.u.) vs. time for various concentrations of SNP and SNP—P70 (see FIG. 10A), and a graph of clot time (half-time, s) vs. concentration (mg/mL) for SNP and SNP—P70 (see FIG. 10B).

Experiments were performed to determine hemostatic activity at various coagulopathy conditions, such as dilution, hypothermia and acidosis. A dilution condition was tested using a phosphate buffered solution (PBS). Hypothermia was tested by incubating plasma below the usual 37° C., which created a hypothermic condition. Acidosis was tested using a dilute phosphoric acid solution to acidify the plasma below a pH of 7.1. The experiments utilized a set concentration of lipidated tissue factor (LTF)—0.5 ng/ml for TEG tests, 0.185 ng/ml for fluorescence dye tests—to ensure timely initiation of the coagulation cascade through the extrinsic pathway and the body's main response to vessel injury. The SNP—P70 was tested at 0.25 mg/ml without LTF to compare its ability to form clots.

Figure 11A:
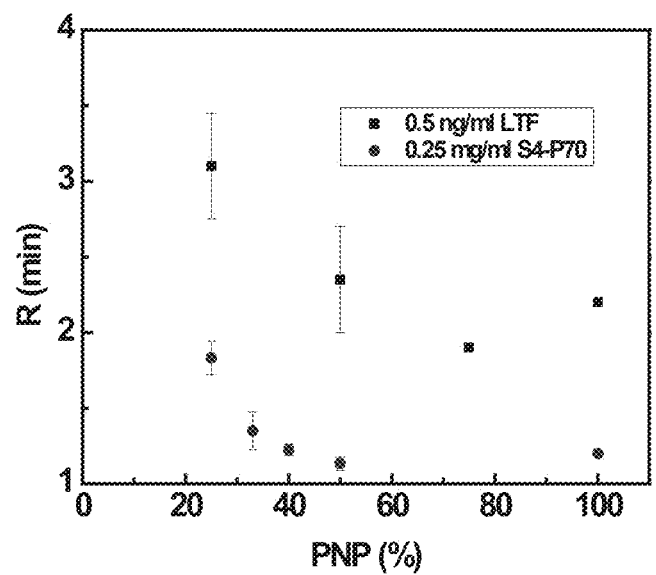
FIG. 11A shows a graph of clotting time, R, (min) vs. % of pooled normal plasma (PNP) for experiments to determine hemostatic activity in diluted samples, according to embodiments of the present disclosure.
Figure 11B:
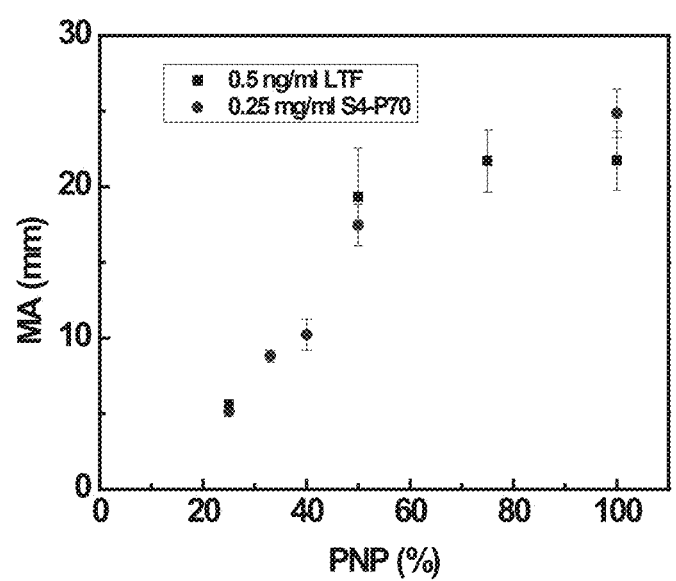
FIG. 11B shows a graph of clot size, MA, (mm) vs. % of pooled normal plasma (PNP), according to embodiments of the present disclosure.

Using TEG and dye fluorescence, a dilution baseline was established. SNP—P70 was added at the threshold concentration (i.e., concentration that resulted in a minimum clotting time, R) of 0.25 mg/ml identified in the TEG experiments above. As shown in FIG. 11A, SNP—P70 lowered clotting time in diluted samples. FIG. 11B shows a graph of clot size, MA, (mm) vs. % of pooled normal plasma (PNP).

Figure 12A:
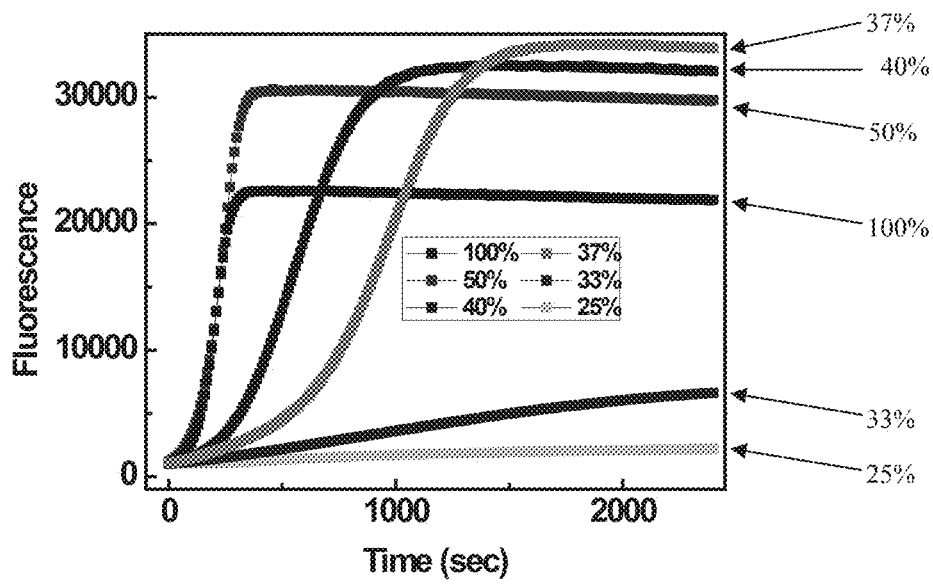
FIG. 12A shows a graph of fluorescence vs. time (sec) for thrombin generation times from 100% plasma to 25% plasma (i.e., 100% plasma is 100% plasma and 0% dilutant) with no SNP—P70 added.
Figure 12B:
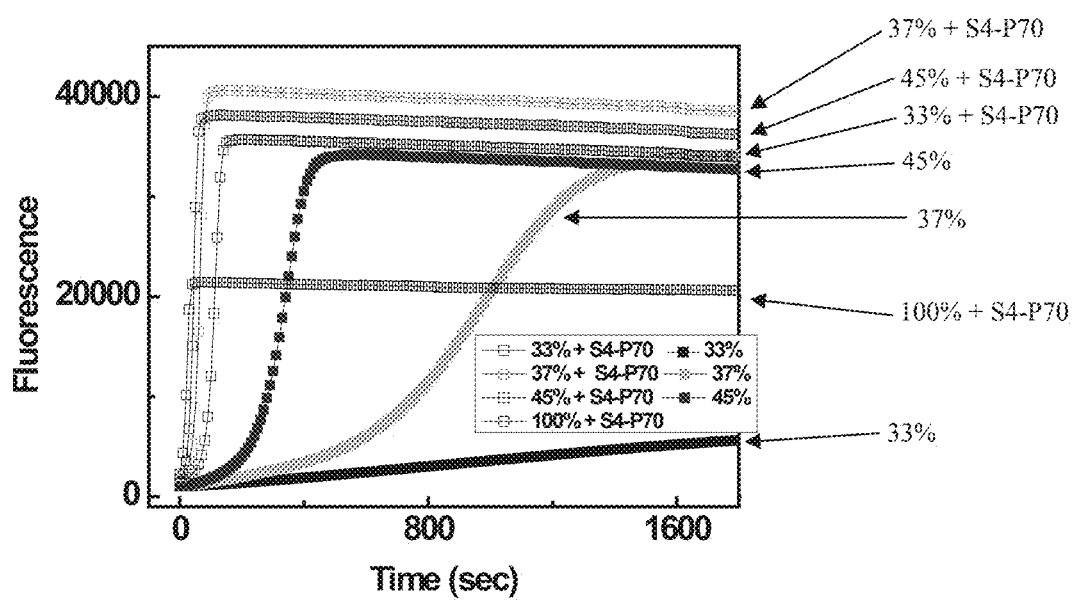
FIG. 12B shows a graph of fluorescence vs. time (sec) for thrombin generation times at various dilution conditions for samples with SNP—P70 added, according to embodiments of the present disclosure.

Results of the dye fluorescence experiments at various dilution conditions are shown in FIGS. 12(*a*) and 12(*b*). FIG. 12A shows a graph of fluorescence vs. time (sec) for thrombin generation times from 100% plasma to 25% plasma (i.e., 100% plasma is 100% plasma and 0% dilutant) with no SNP—P70 added. FIG. 12B shows a graph of fluorescence vs. time (sec) for thrombin generation times at various dilution conditions for samples with SNP—P70 added. As shown in FIG. 12B, the addition of SNP—P70 generated thrombin quickly even under plasma dilution conditions.

Figure 13A:
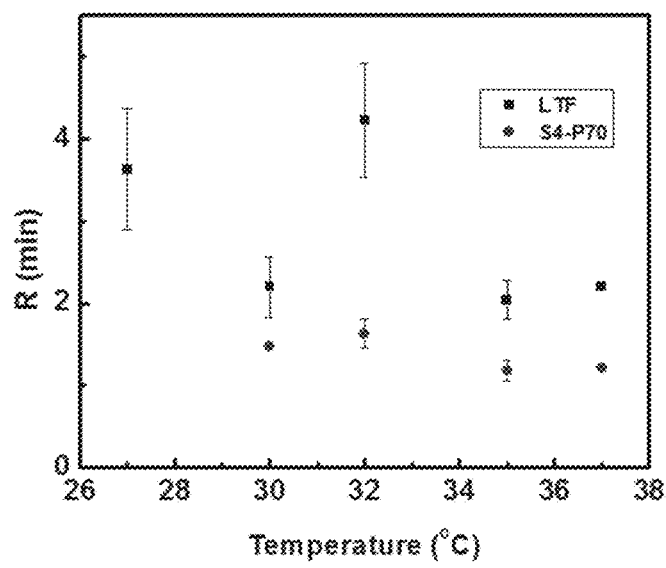
FIG. 13A shows a graph of clotting time, R, (min) vs. temperature (° C.) for experiments to determine hemostatic activity of SNP—P70 under hypothermic conditions, according to embodiments of the present disclosure.
Figure 13B:
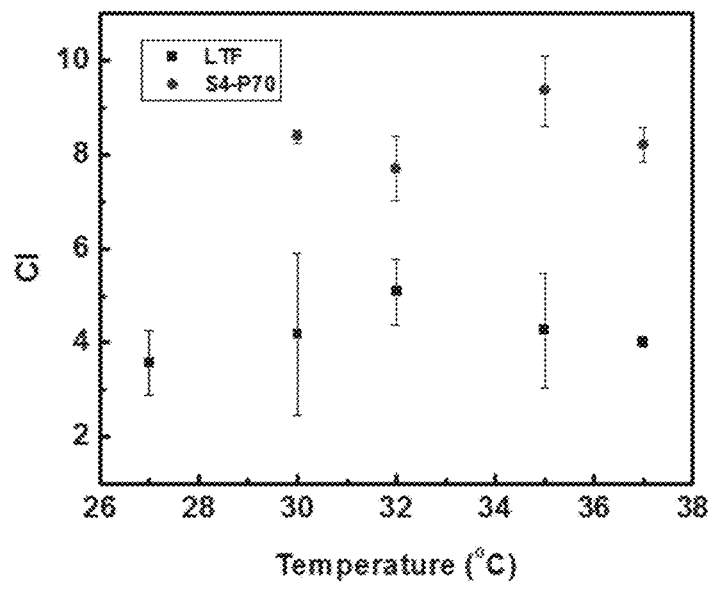
FIG. 13B shows a graph of coagulation index (CI) vs. temperature (° C.) for SNP—P70 under hypothermic conditions, according to embodiments of the present disclosure.

Hypothermia occurs when the body temperature drops below 37° C. The drop in temperature may lead to a decreased rate in the kinetics of many of the coagulation factors, such as formation of the tissue factor-FVIIa (TF-FVIIa) complex during the initiation phase of coagulation. FIG. 13A shows a graph of clotting time, R, (min) vs. temperature (° C.) for experiments to determine hemostatic activity of SNP—P70 under hypothermic conditions. FIG. 13B shows a graph of coagulation index (CI) vs. temperature (° C.) for SNP—P70 under hypothermic conditions. The addition of SNP—P70 to hypothermic plasma resulted in improved coagulation across all TEG parameters, including a decrease in clotting time and an increase in coagulation index. The coagulation index (CI) showed that SNP—P70 had significant procoagulant activity. The coagulation index (CI) combines all four TEG facets—R, K, alpha, and MA—into a single value; the more positive the CI, the stronger the procoagulant.

The experiments described above show that SNP—P70 has significantly greater hemostatic activity than bare SNP and LTF in lowering clot times while forming strong clots. Experiments on FXII deficient plasma showed that SNP—P70 initiated clotting through the FXa coagulation pathway. SNP—P70 also decreased clot time and quickened thrombin generation under coagulopathic conditions, such as dilution and hypothermia.

PEGylated Nanoparticles

Experimental Protocols

Functionalization of SNP with APTES 0.5 g of SNP and 50 Ml ethanol were added to a flask and sonicated. 1 µL of APTES was added while stirring vigorously. The mixture was stirred 24 hours at RT. After 24 hours, the mixture was put in centrifuge tubes and spun for 30 min at 14k. Supernatant was discarded, ethanol was added and the mixture was sonicated. The mixture was centrifuged for 30 min at 14k. Supernatant was discarded, ethanol was added and the mixture was sonicated. The resulting SNP-APTES was dried overnight at 60° C.

PEGylation of SNP to Produce SNP-APTES-PEG-$OCH_3$ 12.5 mg of SNP-APTES was prepared in 250 µL 1 mM NaOH (50 mg/mL). 2 mg of NHS-PEG-$OCH_3$ was prepared in 25 µL DMSO (2 kDa, 5 kDa, 20 kDa). 25 µL PEG-solution per 250 µL SNP-APTES was added to the SNP-APTES. The mixture was sonicated and incubated 15 min at RT. The mixture was centrifuged 2× for 5 min at 3.5k, and cleaned with DI. The volume was brought to 250 µL, and the mixture was sonicated.

Adding Linking Group to SNP-APTES

Four different linkers were used.

| Linker | MW (g/mol) |
|---|---|
| SPDP-PEG8-NHS | 735.87 |
| SPDP-PEG16-NHS | 1087.30 |

| Linker | MW (g/mol) |
| --- | --- |
| SPDP-PEG2k-NHS | 2000 |
| SPDP-NHS | 312 |

50 mg/mL of the SNP-APTES particles were dispersed in 10 mM NaOH (e.g., 25 mg in 495 μL DI and 5 μL 0.1 M NaOH). The mixture was sonicated. 5 μL of the linker in DMSO (10 mM) was added per 500 μL of SNP-APTES, pH 7-8 (100 μM final linker). The mixture was sonicated. The mixture was incubated 30 min to 2 hours at RT. The mixture was centrifuged 2× for 10 min at 6k, and cleaned with DI, pH 5-8. The volume was brought to 500 μL with MIlli-Q water.

Adding Peptide to SNP-APTES-Linker

The following peptides were used.

| Long name | Short name | Use | MW |
| --- | --- | --- | --- |
| Ac-CGGIEGRGG SGGKG-NH2 | C-IE-GK (CG-14) | This peptide included: a Cys, to attach to the OPSS linker; an IEGR sequence for being recognized by FXa; and a Lys, where the PEG was attached. | 1232.34 |
| Ac-CGGIEGRGG K(FAM)GGKG-NH2 | C-IE-FK (CG-14) | This peptide included a Cys for binding to the linker; an IEGR sequence for cleavage; a fluorescein dye (FAM) used to monitor cleavage; and a Lys for NHS-PEG attachment. The fluorescein (FAM) was to the right side of the cleavage site, which resulted in fluorescein in the supernatant after cleavage by FXa. | 1631.78 |
| FAM-x-CGGIEGRGG SGGKG-NH2 | CF-IE-GK (CG-14) | This peptide included a Cys for binding to the linker; an IEGR sequence for cleavage; a dye used to monitor cleavage; and a Lys for NHS-PEG attachment. The fluorescein (FAM) was to the left side of the cleavage site, which resulted in fluorescein remaining on the particle after cleavage by FXa. | 1661.79 |
| FAM-x-CGGERGIGG SGGKG-NH2 | CF-Ersc-GK (CG-14) | This peptide included a Cys for binding to the linker; a dye used to monitor cleavage; and a Lys for NHS-PEG attachment. The peptide does not include the IEGR sequence necessary for cleavage by FXa. | 1661.79 |

Peptide solutions were prepared in Milli-Q water, e.g. 0.75 mM. Concentrations of peptide used were: (a) 1.1 mg/mL C-IE-GK, (b) 2 mg/mL C-IE-FK, (c) 2.1 mg/mL CF-IE-GK, and (d) 2.1 mg/mL CF-Ersc-GK. 50 μL of the peptide solution was added to 500 μL particle solution (50 mg/mL particles). The mixture was incubated for 10 min at RT, and then centrifuged 10 min at 6k. Supernatant was removed and reaction product was washed with DI, and the volume was brought to 500 μL. Spinning and washing were repeated, and the volume was brought to 500 μL with Milli-Q water.

Functionalization of SNP Through SPDP

Nanoparticles were prepared with the following structure: SNP-APTES-SPDP-cysPep-K-PEG-OCH$_3$.

SNP was prepared by adding dropwise 7.6 mL of TEOS into a stirred solution 280 mL of ethanol. 11.4 mL NH4OH (28%) was added dropwise and the mixture was stirred for 24 hours. The mixture was centrifuged 3× for 30 min at 13k, and washed with ethanol. SNPs were dried overnight at 60° C. SNPs were calcined at 550° C. for 4 hours.

SNP-APTES was prepared by adding 0.5 g of SNP in 50 mL ethanol and sonicating. APTES was added while stirring vigorously. The mixture was stirred for 24 hours, and then centrifuged 2× for 30 min at 13k, and cleaned with ethanol. The SNP-APTES was dried at 60° C. overnight and then ground with a mortar.

Succinimidyl 3-(2-pyridyldithio)propionate (SPDP) was added as follows. 50 mg/mL of SNP-APTES was dispersed in 10 mM NaOH (e.g., 25 mg in 495 μL DI and 5 μL 0.1 M NaOH) and sonicated. 3.1 mg/mL SPDP in DMSO (MW 312) (10 mM stock) (e.g., 1 mg in 320 mL) was prepared. 5 μL SPDP per 500 μL of SNP-APTES, pH 7-8 (100 μM final SPDP) was added and the mixture was sonicated. The mixture was incubated 30 min to 2 hours at RT. The mixture was centrifuged 2× for 10 min at 6k, and cleaned with DI, pH 5-8. The volume was brought to 500 μL.

A peptide was added as follows. 50 μL of 2 mg/mL cys-peptide-K (e.g., biotin-x-CDGSRPARSGR-"SAGGKDA-OH) was added to the above solution and incubated 10 min at RT. The mixture was centrifuged 2× for 5 min at 6k, and cleaned with DI. The volume was brought to 500 μL.

SNP-APTES-SPDP-cysPep-K was PEGylated as follows. 4 mg of NHS-PEG-OCH3 in 50 μL DMSO (2k PEG or larger) was prepared. 50 μL PEG solution per 500 μL SNP-APTES-SPDP-cysPep-K was added and the mixture was incubate 10 min at RT. The mixture was centrifuged 2× for 10 min at 6k, and cleaned with DI. The volume was brought to 500 μL.

The resulting structure was SNP-APTES-SPDP-cysPep-K-PEG-OCH3. The PEG protected nanoparticle were noncoagulating.

The cleavable peptide linker was cleaved by adding an enzyme as follows. To 50 μL of SNP-APTES-SPDP-cysPep-K-PEG-OCH$_3$ was added 50 μL of uPA enzyme (urokinase plasminogen activator) or trypsin, and the mixture was sonicated, 10-60 min (e.g., 30 min) at 37° C. The mixture was centrifuged, washed and volume adjusted to 50 µL with DI.

The structure was now SNP-APTES-SPDP-cysPepR-OH, and was hemostatically active.

SNP-APTES Conversion to PEG-OPSS and Coupling to Biomolecule

Reactions:

OPSS is S—S-Pyridyl, which reacts with thiols to form a disulfide product:

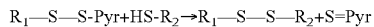

where $R_1$ is the nanoparticle, $R_2$ is the biomolecule

SNP-APTES 0.1 g (220 nm diameter) was dispersed in 5 mL DI with sonication. NHS-PEG-OPSS 5 kDa, 10 mg, was dissolved in DMSO (0.5 mL). The PEG solution was added to the SNP-APTES solution and the mixture was sonicated. pH was adjusted to pH 7 with HEPES buffer. The mixture was sonicated and incubated 1 hour. The mixture was centrifuged and cleaned 2-3× with washing buffer. The volume was brought to 5 mL. The coupling reaction to a thiol-containing biomolecule was performed by adding together 200 µL SNP-linker-PEG-OPSS, 200 µL buffer (1M Hepes), and 20 µL 1 mg/ml peptide in 1M Hepes. The mixture was incubated at room temperature for 1 hour, cleaned 3 times, and stored at 4° C.

Results and Discussion

Figure 14:
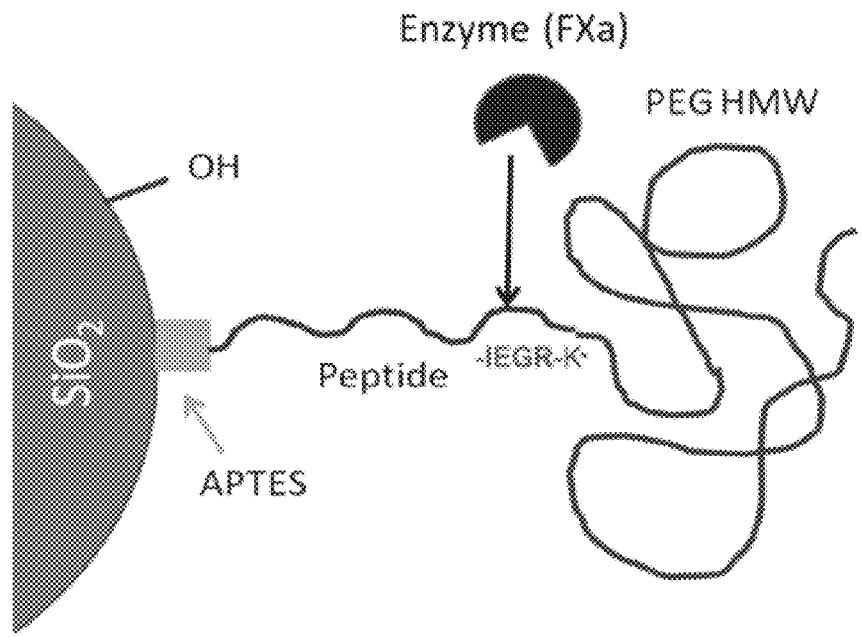
FIG. 14 shows a schematic of a silica nanoparticle that includes PEG attached to the nanoparticle through a cleavable peptide linking group that may be cleaved by Factor Xa, thrombin or other enzymes, according to embodiments of the present disclosure.

PEGylated nanoparticles were prepared that included a cleavable peptide linking group with an IEGR sequence that connected the nanoparticle to the PEG (FIG. 14). Activated Factor X (FXa) cleaved the peptide at the IEGR (SEQ ID NO: 1) sequence, removing the PEG and leaving the activated SNP.

Figure 15:
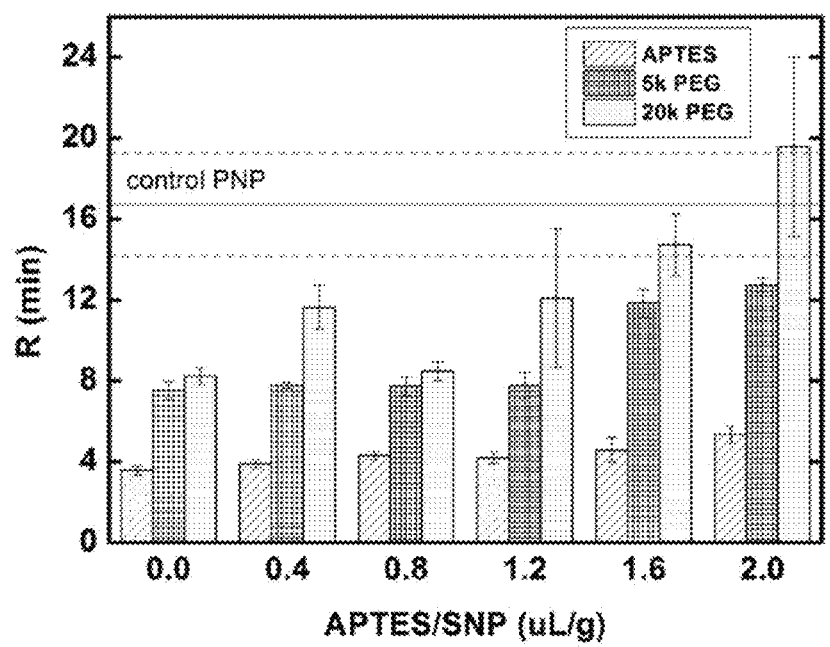
FIG. 15 shows a graph of clotting time, R, vs. 3-aminopropyl triethoxysilane (APTES) to SNP ratio, according to embodiments of the present disclosure.
Figure 16:
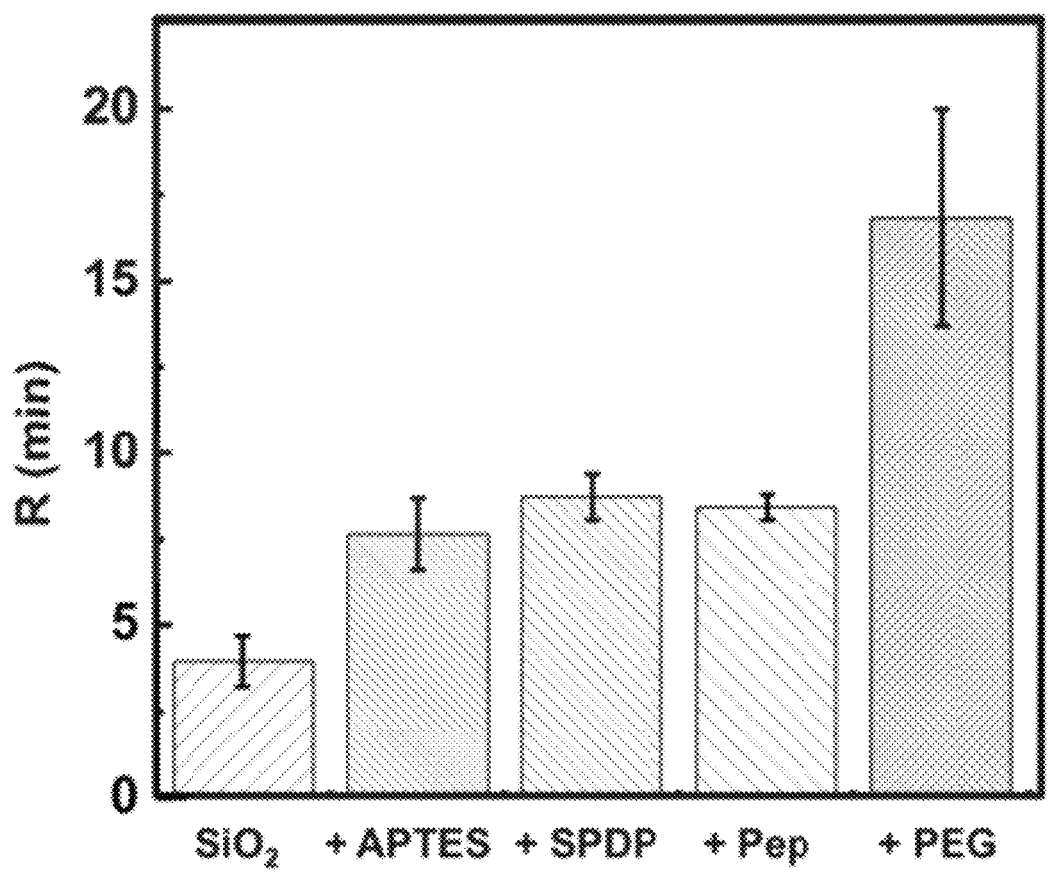
FIG. 16 shows a graph of clotting time, R, for unfunctionalized SNP and various functionalized SNPs (Pep: peptide; SPDP: succinimidyl 3-(2-pyridyldithio)propionate; PEG used was 2 kDa), according to embodiments of the present disclosure.

FIG. 15 shows a graph of clotting time, R, vs. 3-aminopropyl triethoxysilane (APTES) to SNP ratio, according to embodiments of the present disclosure. FIG. 16 shows a graph of clotting time, R, for unfunctionalized SNP and various functionalized SNPs (Pep: peptide; SPDP: succinimidyl 3-(2-pyridyldithio)propionate; PEG used was 2 kDa), according to embodiments of the present disclosure.

When bound to the nanoparticle surface, cross-linkers such as 3-aminopropyl triethoxysilane (APTES) reduced the active surface for coagulation (FIGS. 15 and 16). The ratio of APTES to silica was decreased to obtain a PEG-linker-APTES-silica SNP that would retain a dual nature—inert in healthy blood vessels while converting to procoagulant when activated by a linker-specific protease. When functionalized solely with APTES, at low coverage, the SNP retained its procoagulant nature. When PEG attached to these nanoparticles via the APTES, the SNP became protected. Coupling PEG (2 kDa or more, e.g., 5 kDa) increased clotting times back to that of normal recalcified plasma. Removing PEG activated the procoagulant activity of the SNP.

Example 2

Particle Design and Tests

Experiments were performed to conjugate polyP onto the surfaces of organic and inorganic particles to investigate the effects of particle surface properties (i.e. surface charges and ligands) and particle sizes. Hybrid particles were generated with thermal sensitive or chemically responding polymers and polyP at the surface. Under the switch conditions (such as, lower temperature or over expressed chemicals), the polymer brushes were extended or folded to either shield or expose the surface ligands such as polyP.

Figure 17:
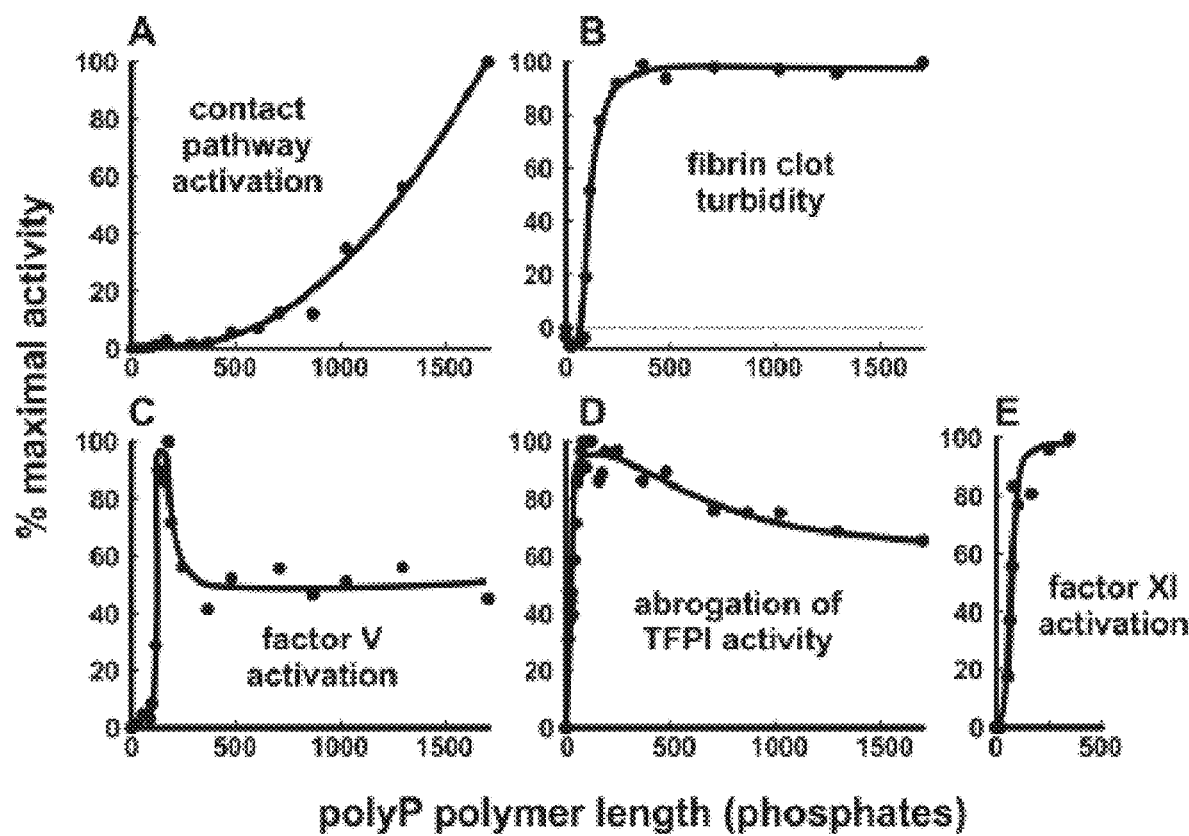
FIG. 17 shows graphs of the size-dependence of a phosphate polymer's (polyP's) procoagulant activities, according to embodiments of the present disclosure. Data are plotted as % maximal activities versus phosphate polymer (polyp) polymer length.

In certain embodiments, polyP activates and accelerates the clotting cascade. In some instances, steps in clotting are enhanced by polyP. Size dependence of polyP's procoagulant activities showed that shorter polyP polymers accelerated the activation of factors V and XI, while longer polyP polymers initiated clotting via the contact pathway (FIG. 17). In some cases, the specific procoagulant activity of polyP-containing nanoparticles may be tailored by varying the polyP polymer lengths used, as well as by controlling the amount of polyP per particle. The polyP particles may have the capacity to induce clotting in a controlled and directed manner, compared to free polyP. Without being limited to any particular theory, in some instances, polyP particles may interact with blood plasma and cause a series of events, including the adsorption of albumin, IgG and fibrinogen, platelet adhesion and activation, and thrombosis. PolyP may shorten the clotting time, depending on the concentration, size and surface properties of the particles.

Experiments were performed for covalently attaching polyP to primary amines, which facilitated polyP-nanoparticle assembly. This reaction used the zero-length cross-linking reagent, EDAC (1-ethyl-3-[3-dimethylamino)propyl]carbodiimide), to promote the formation of stable phosphoramidate linkages between primary amines and the terminal phosphates of polyP. Other functional groups may be used at the termini of polyP, in order to broaden the types of coupling reactions that may be used. Nearly 80% end labeling was achieved using polyamines such as spermine and spermidine. The reaction product contained primary amines attached to the ends of the polyP polymers, which reacted with a wide variety of derivatizing reagents that target primary amines. Free sulfhydryls groups may also be introduced onto the termini of the labeled polyP polymers, in order to use sulfhydryl-labeling chemistries.

Multiple terminal amine surface groups may also be used to conjugate a controlled number of polyP with these surface amines. G4Poly(amido amine) (PAMAM) dendrimers associated tightly with polyP and may serve as a platform for assembling polyP-containing nanoparticles. PolyP conjugation to three types of particles (e.g., G4Poly(amido amine) (PAMAM) dendrimers, amino polystyrene, and amine ligands bound to gold nanoparticles) were investigated to verify three hypothesis: (1) plasma clotting kinetics and mechanism was affected by the size (or curvature) of the particles and an optimized condition could be selected; (2) the choice of the biocompatible core material would not have significant effects on the plasma clotting kinetics or mechanism; and (3) the functionalities of the particles was determined by the surface properties (e.g., neutral vs. charged and the chain length of polyPs).

In certain embodiments, the total number of polyP chains affected clotting of plasma. In some cases, the mechanism and time to clot changed with free chains of polyP. Three control groups were selected to compare with the particles-polyP conjugates: (1) free polyP with the same molecular weight at the same concentration; (2) linear polyP with the molecular weight equivalent to the summation of polyP the molecular weight attached on a single particle (e.g., polyP molecular weight times the conjugation number); and (3) particles without polyP.

Dendrimer-polyP Conjugation

PolyP (45-mer) was conjugated to the G4 PAMAM dendrimer, which had 64 primary amines on the surface. The zero-length cross linking reagent, EDAC was used to couple primary amines to phosphates via phosphoramidate linkages. The separation of free polyP and dendrimer-polyP conjugate was done by employing size exclusive columns. The plasma clotting efficiency was tested by using a viscosity based coagulometer.

To find out the optimized conditions for conjugation, various conditions, such as the temperature, pH and reaction time were tested. The fluorescamine assay was used to test the amount of the unreacted primary amines on dendrimer, which indicated the conjugation efficiency.

Figure 18:
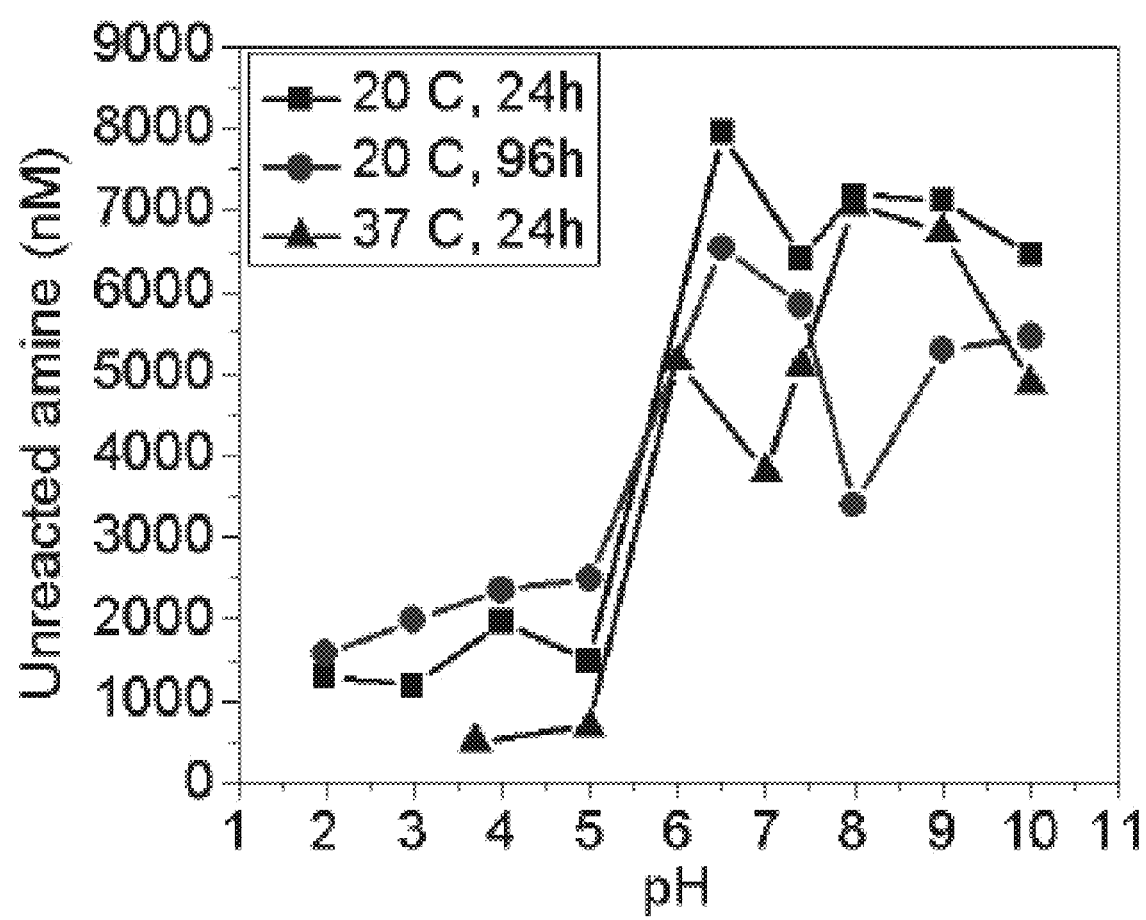
FIG. 18 shows a graph of the efficiency of dendrimer-polyP conjugation at different pH, temperature and time conditions, according to embodiments of the present disclosure.

The conjugation efficiency under various conditions was tested and shown in FIG. 18. The reactions were more efficient at low pH conditions. The amine concentration before the reaction was about 3400 nM. In some cases, there was a higher amine concentration after reaction as compared to the control, which was due to the degradation of the dendrimer (discussed below). The optimized condition was selected as 4 hours at 37° C. and pH 4, after which >80% of the primary amine on dendrimer had reacted with polyP.

Dendrimer and polyP Stability

Figure 19:
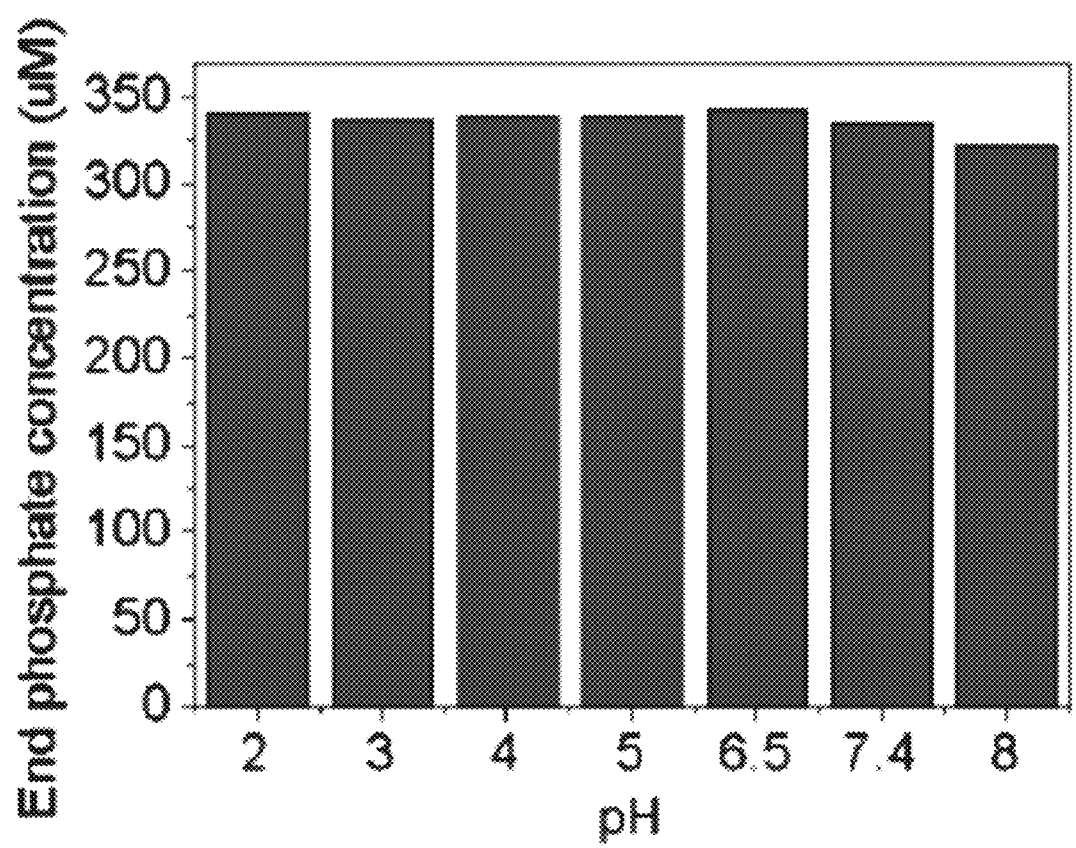
FIG. 19 shows a graph of the stability of polyP at 37° C. and various pH conditions, according to embodiments of the present disclosure.
Figure 20:
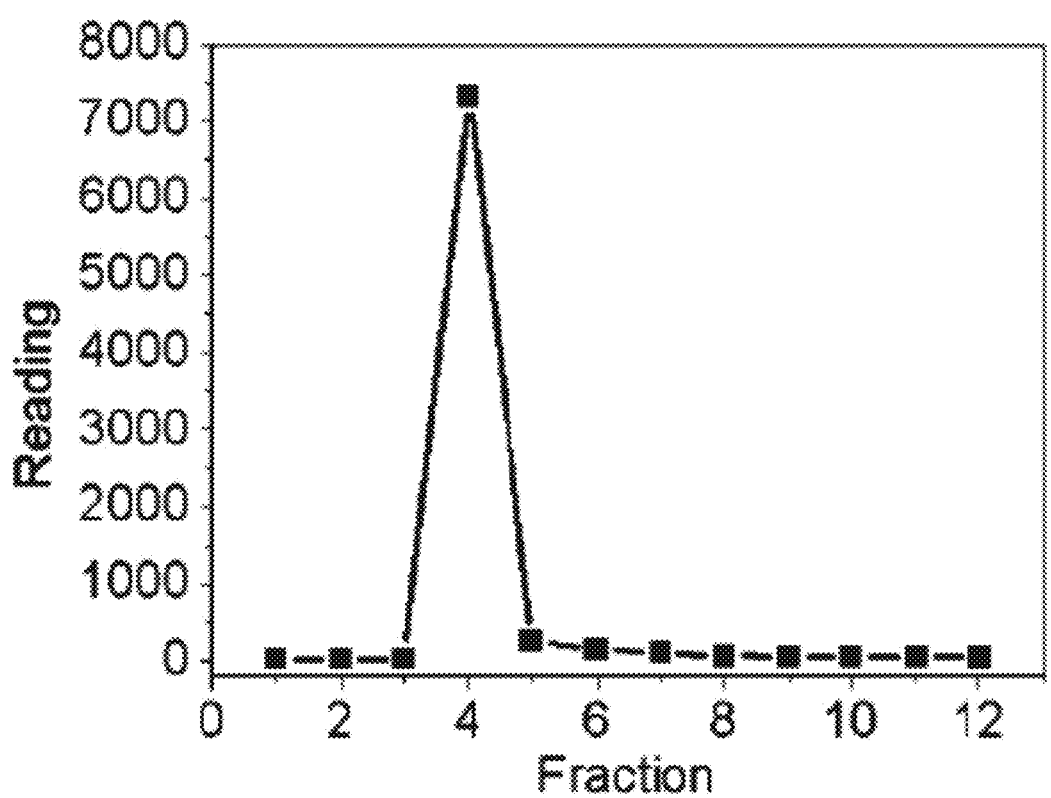
FIG. 20 shows a graph of dendrimer running through the Econo-Pac 10 DG Columns, according to embodiments of the present disclosure. The running phase was DI water.
Figure 21:
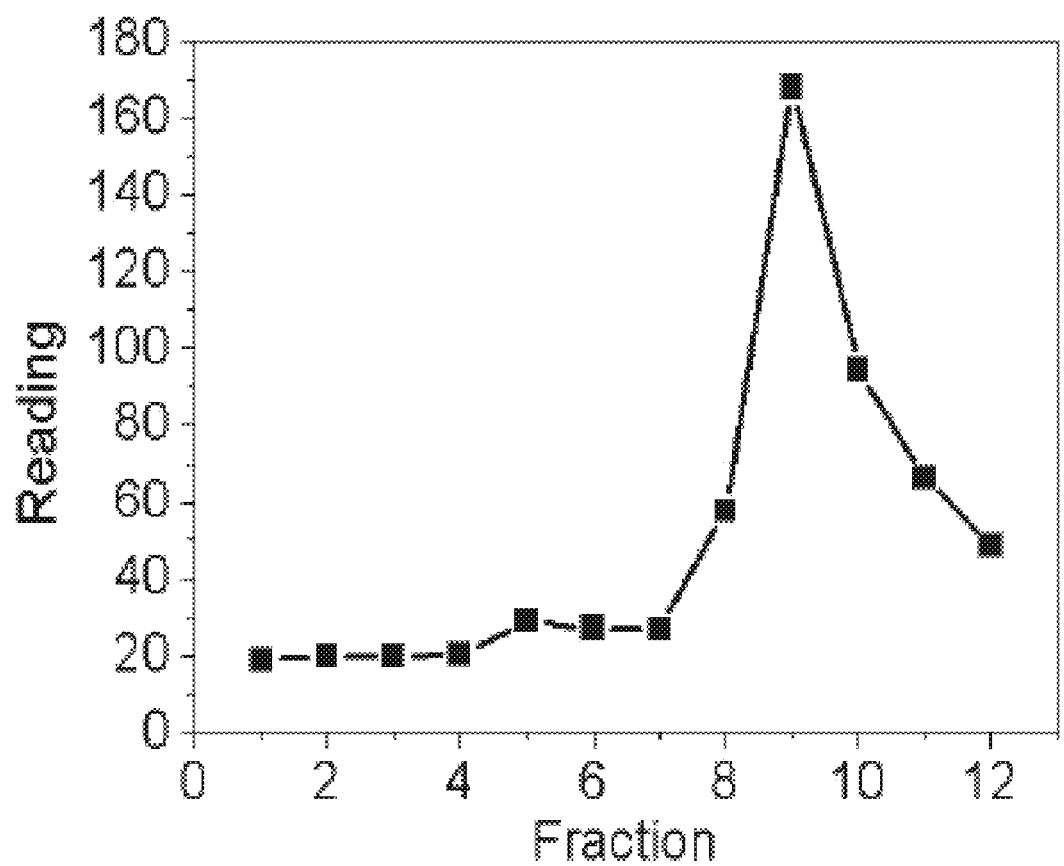
FIG. 21 shows a graph of dendrimer running through the Econo-Pac 10 DG Columns, according to embodiments of the present disclosure. The running phase was 25 mM borate acid buffer at pH 9.
Figure 22:
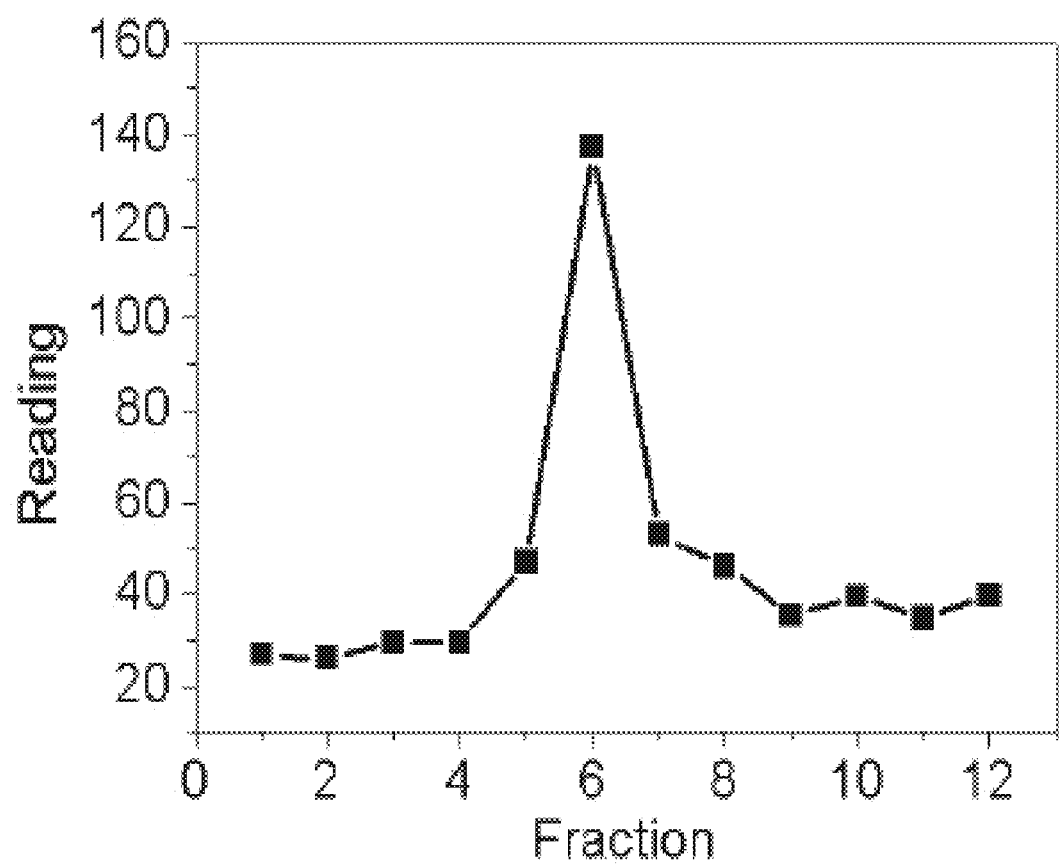
FIG. 22 shows a graph of dendrimer-polyP running through the Econo-Pac 10 DG Columns, according to embodiments of the present disclosure. The running phase was borate acid buffer. The reading was for dendrimer.
Figure 23:
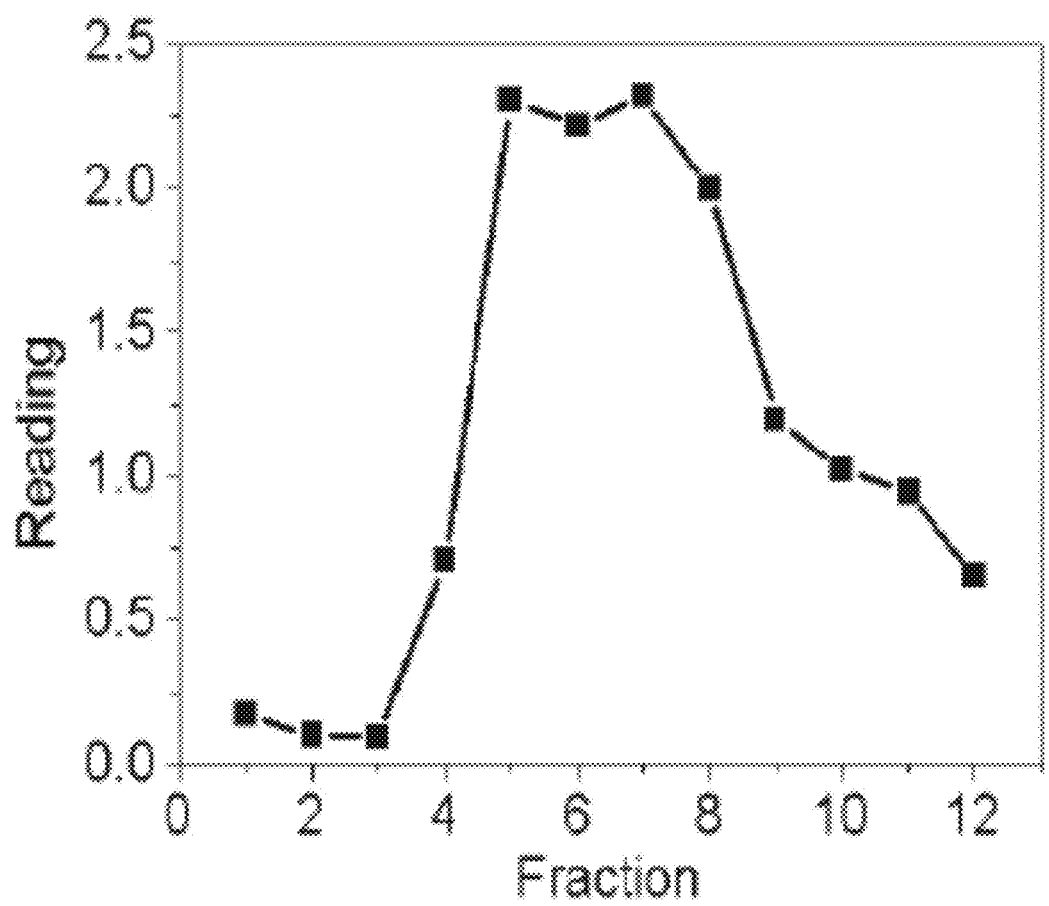
FIG. 23 shows a graph of dendrimer-polyP running through the Econo-Pac 10 DG Columns, according to embodiments of the present disclosure. The running phase was borate acid buffer. The reading was for polyP.

The stability of polyP at 37° C. after 24 hours was tested as a function of pH (FIG. 19). Compared to the sample at pH 7.4, there was no increase of free phosphate, which indicated little degradation. Therefore, polyP was stable for the first 24 hours at 37° C. and as low as pH 2. The stability of dendrimer at various conditions was also tested. Below pH 4 and above 32° C., more than 25% dendrimer degraded within 4 hours. At 20° C. and pH 4, the dendrimer was stable for the first 4 hours and about 10% degradation happened at 24 hours. Separation Econo-Pac 10DG Columns were first used to separate the free polyP and dendrimer-polyP conjugates. Recovery of dendrimer was highly depend on the running phase. When purified water was used as the running phase, as shown in FIG. 20, the dendrimer eluted in the 9th fraction but recovery of dendrimer was only about 5%. In some cases, the dendrimer may have been trapped in the column because of ionic interactions. Therefore, in later experiments, buffers with at least 20 mM salt concentration were used to eliminate the effect of ionic interactions between the gel and the solute. As an example, with 25 mM borate acid buffer at pH 9, dendrimer eluted at the 4th fraction and recovery rate was above 85% (FIG. 21). Dendrimer-polyP conjugate was then separated on the column (FIGS. 22 and 23). The dendrimers eluted at the 6th fraction, while the peak of polyP was from the 5th fraction to the 7th fraction. Therefore, separation of free polyP from the conjugate through the Econo-Pac 10 DG Column was not achieved.

Figure 24:
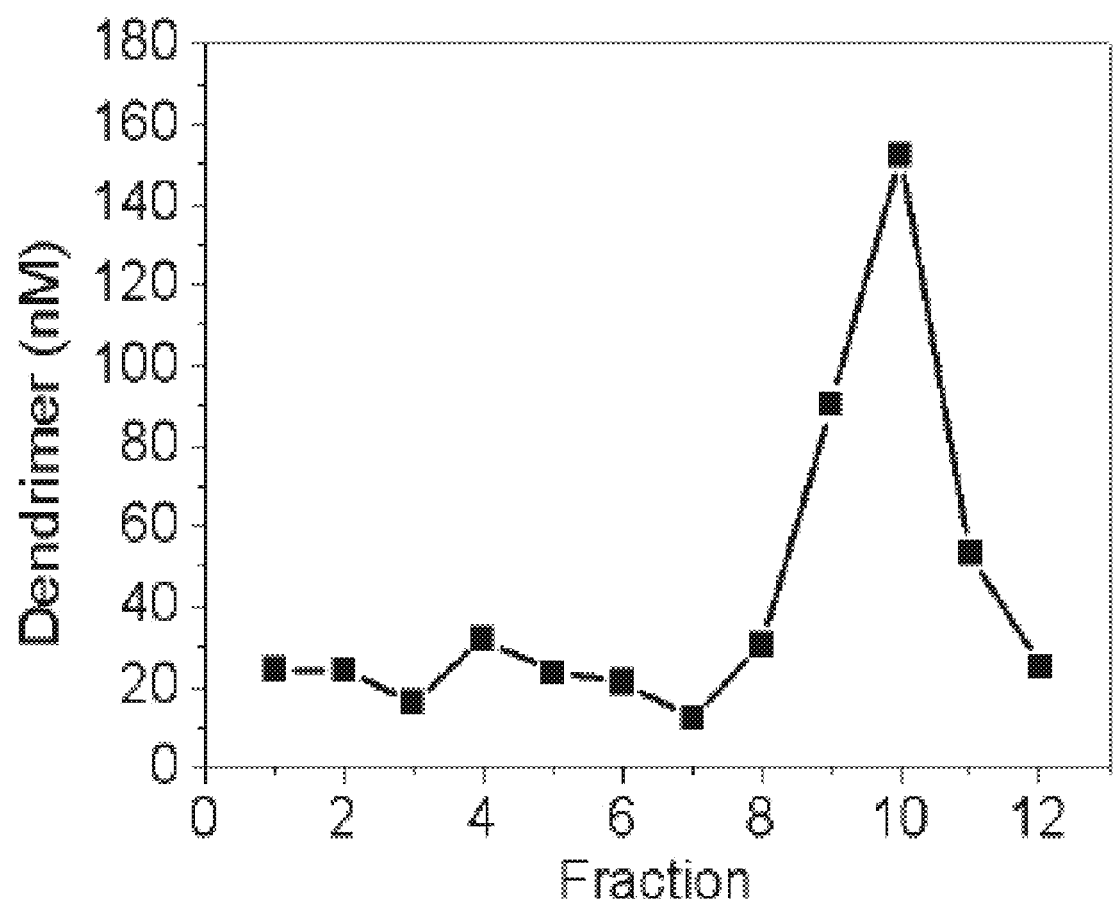
FIG. 24 shows a graph of dendrimer-polyP running through the BG P-10 Gel packed columns, according to embodiments of the present disclosure. The running phase was 1M LiCl. The reading was for dendrimer.
Figure 25:
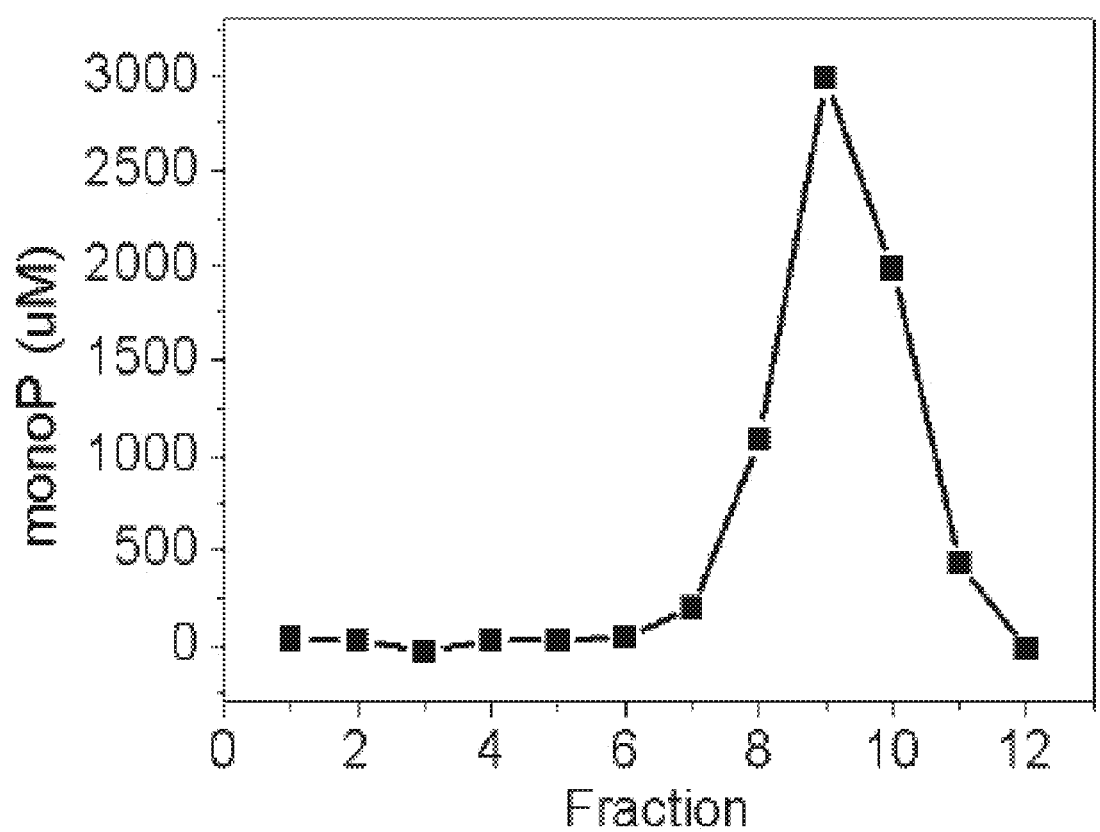
FIG. 25 shows a graph of dendrimer-polyP running through the BG P-10 Gel packed columns, according to embodiments of the present disclosure. The running phase was 1M LiCl. The reading was for PolyP.

Size exclusion columns packed with Bio-Gel® P-10 gel were then used for the separation of conjugated polyP from the un-reacted polyP. Bio-Gel® P-10 Gel with a molecular weight (MW) fractionation range from 1,500-20,000 was selected, which was suitable to separate the polyP-dendrimer conjugation (MW>20,000) from the un-reacted ones (MW<13,700) The dendrimer eluted at the 10th fraction and the polyP came out at the 9th fraction (FIGS. 24 and 25), which was deemed insufficient separation.

Figure 26:
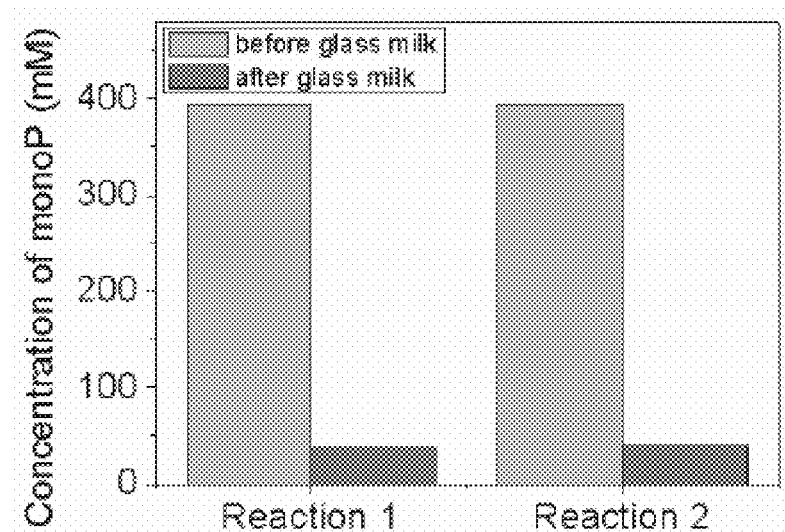
FIG. 26 shows a graph of PolyP concentration before and after glass milk assay performed on two previous reactions, according to embodiments of the present disclosure.

Another separation method tested was with "glass milk", which consisted of silica particles in aqueous solution. 1 μL of glass milk was added to 500 μL of dendrimer-polyP reaction. The glass milk and reaction was then mixed for 30 minutes with occasional vortexing. After mixing, the solution was then centrifuged for 10 minutes at 3,500 RPM. The purified supernatant was collected and the malachite green assay (which quantified phosphate following acid digestion of polyP) was performed to quantify polyP concentration against the same reaction that had not undergone glass milk purification. FIG. 26 shows a decrease in phosphate concentration of over 90% before and after the glass milk separation.

Figure 27:
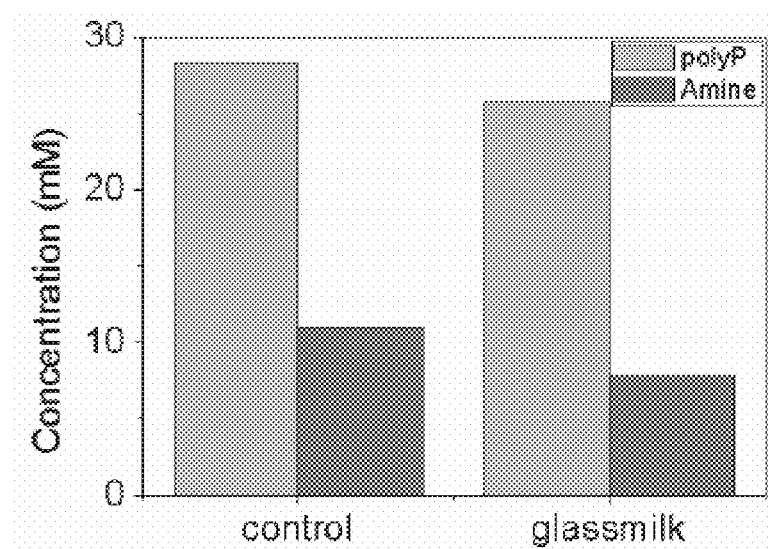
FIG. 27 shows a graph of the concentration of primary amine and PolyP before and after glass milk separation assay, according to embodiments of the present disclosure.

The glass milk assay was performed again and both the malachite green and fluorescamine assays were performed to ensure that only free polyP was removed by the glass milk and that the dendrimer remained in solution. The results in FIG. 27 indicated less efficient separation of polyP than the previous experiment as well as a similar decrease in primary amine and polyP concentrations before and after the glass milk assay. The concentration of primary amine in the control reaction increased from the initial amount expected before reaction, which may have been due to degradation of the reacted dendrimer over time.

Clotting Tests

Figure 28:
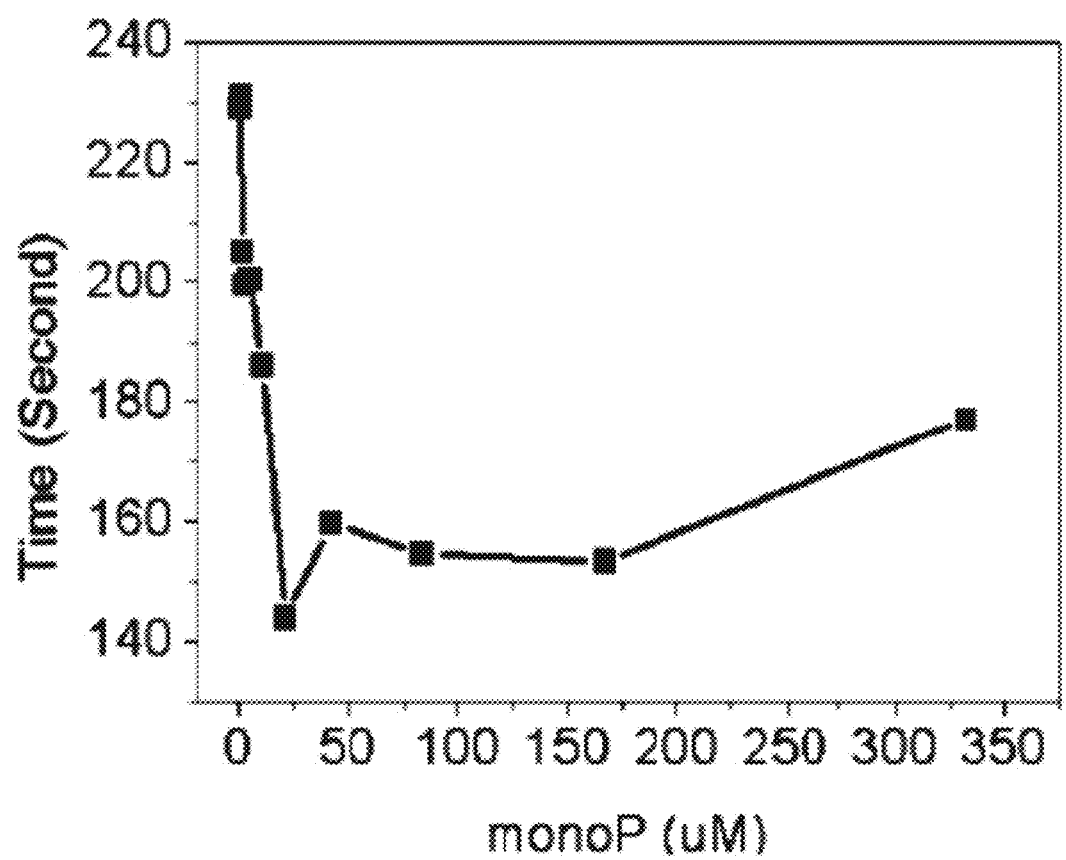
FIG. 28 shows a graph of a blood clotting test for Dendrimer-PolyP conjugation, according to embodiments of the present disclosure.

Plasma clotting times were tested by using a coagulometer. The sample was dendrimer-polyP conjugate which reacted at 37° C., pH 4 for 24 hours. The clotting time for this sample was 143.8 seconds (FIG. 28).

Polystyrene (PS)-polyP Conjugation

Experiments were performed for making a polystyrene (PS)-polyP conjugation. The general procedure for making the PS-polyP conjugation was as follows:

1-2 mL reactions were setup using conditions previously described in amine polyP reactions.

250 mM of 45-mer polyP was added from an aqueous bulk solution made from sodium phosphate glass purchased from Sigma Aldrich.

100 mM pH 4 MES buffer was added to the reaction.

300 mM of EDAC was added to the reaction to activate the reaction between polyP and primary amine.

The amount of primary amine on the surface of the PS particle was characterized using fluorescamine assay. 0.21 mM of primary amine was added to the solution. This was approximately 5 times less than the concentration of polyP chains.

The reaction was brought up to volume with DI water.

The reaction was allowed to proceed for up to 24 hours with vigorous stirring with the concentrations of primary amine consumed tested at various time points.

Figure 29:
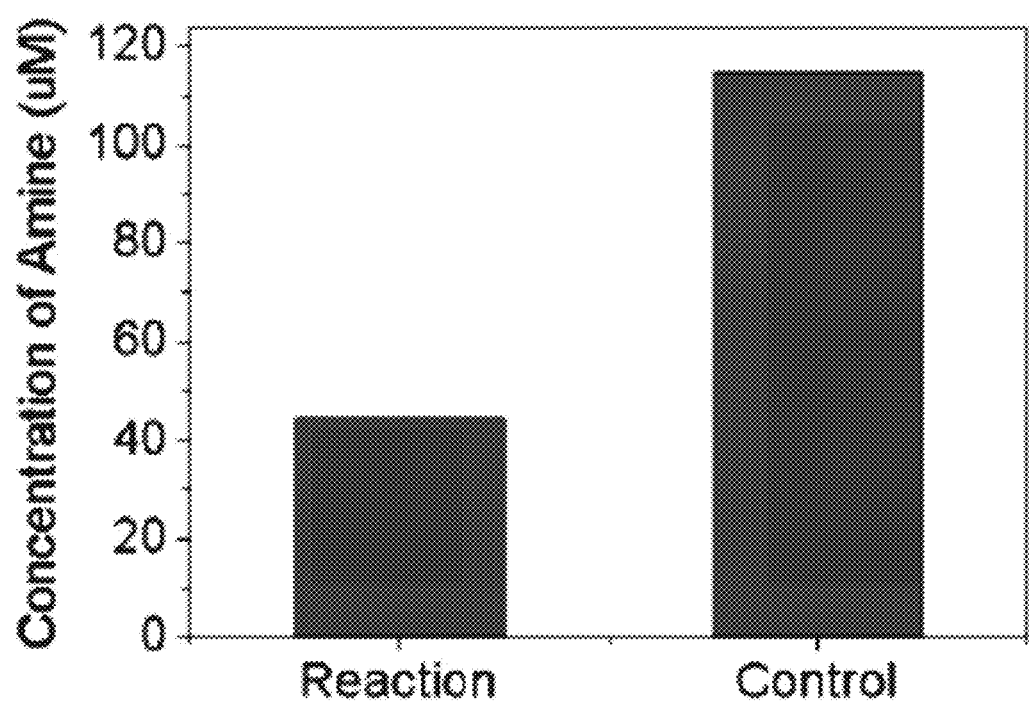
FIG. 29 shows a graph of PS-polyP conjugation, according to embodiments of the present disclosure. The reaction conditions were at room temperature, pH4, and 24 hours.

Polystyrene beads (diameter of 50 nm) with primary amine as the surface functional group were used to conjugate polyP. The reaction condition was 20° C. and pH 4. After 24 hours, more than 60% of the primary amine was reacted with polyP (FIG. 29).

Figure 30:
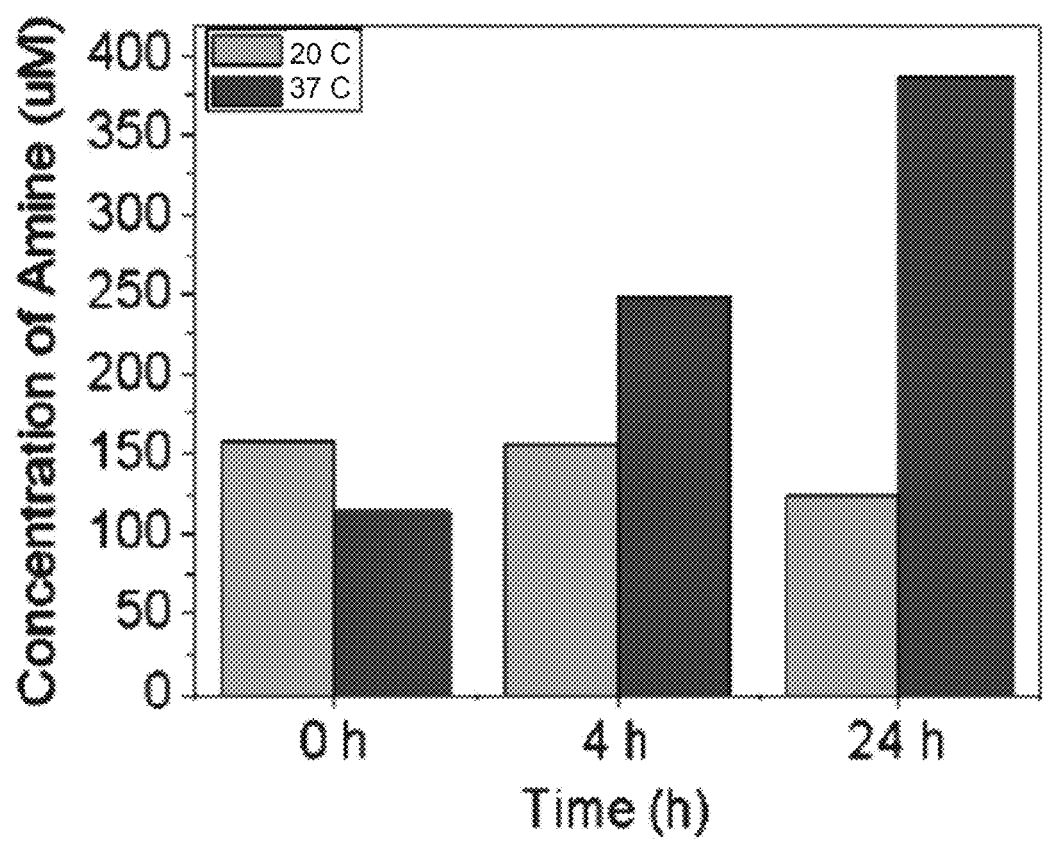
FIG. 30 shows a graph of the amount of amine exposed on the surface of the PS particles at pH 4, according to embodiments of the present disclosure.

The stability of PS beads was tested. As shown in FIG. 30, the amount of amine was stable at 20° C., but increased at 37° C. In some cases, this may be due to that at higher temperature and low pH, amine groups buried inside the particles could be exposed on the surface, which may result in an underestimation of the reaction efficiency.

Gold Nanoparticle-polyP Conjugation

Experiments were performed for making a gold nanoparticle-polyP conjugation. The general procedure for making the gold nanoparticle-polyP conjugation is shown below.

General Reaction Mechanism:
  A. A bulk solution of the thiol-amine ligands of 10.2 mM was made in water and stored at 4° C.
  B. PolyP and amine ligands were reacted as previously described with a ratio of 5:1 excess of polyP. Reactions were performed in pH 4 MES Buffer at 37° C. and at ambient temperature (25° C.).
  C. The amount of reacted ligand was determined using the fluorescamine assay.
  D. Thiol-reacted ligands were bound to 5 nm citrate-coated gold nanoparticles by adding a 20× dilution of the ligand reaction with an excess of 50:1 thiol ligand to gold nanoparticles. About 12-16 ligands were bound to each nanoparticle based on studies that found that 130 ligands were normally bound to 15 nm gold nanoparticles.

E. The mixture was periodically vortexed and continuously mixed for 8 hours.

F. The gold nanoparticle mixture was centrifuged at 13,500 RPM for 20 minutes to remove excess polyP and unbound ligands.

G. The supernatant was removed and the pellet was washed and resuspended with 450 μL DI water.

H. The centrifuging and washing was repeated twice.

I. UV spectroscopy, malachite green assays, and fluorescamine assays were performed to quantify the number of polyP chains bound the surface of the gold nanoparticle.

Figure 31:
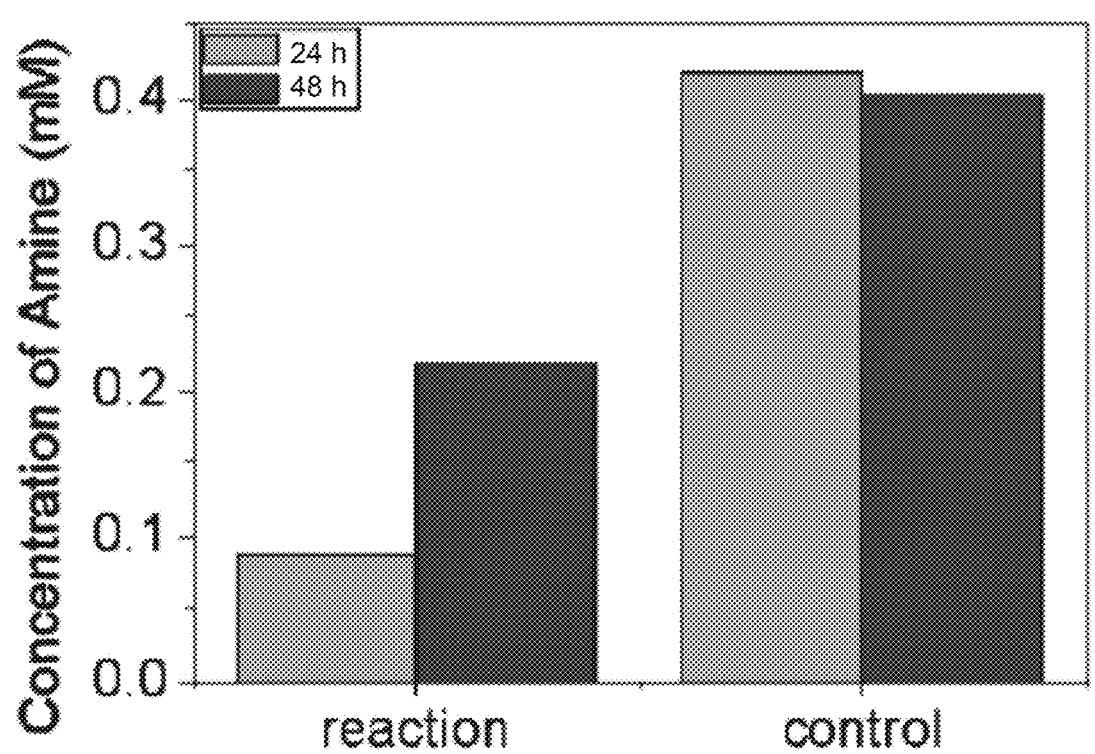
FIG. 31 shows a graph of 24 and 48 hour primary amine concentration of a ligand polyP reaction vs. control under conditions without EDAC, according to embodiments of the present disclosure.
Figure 32:
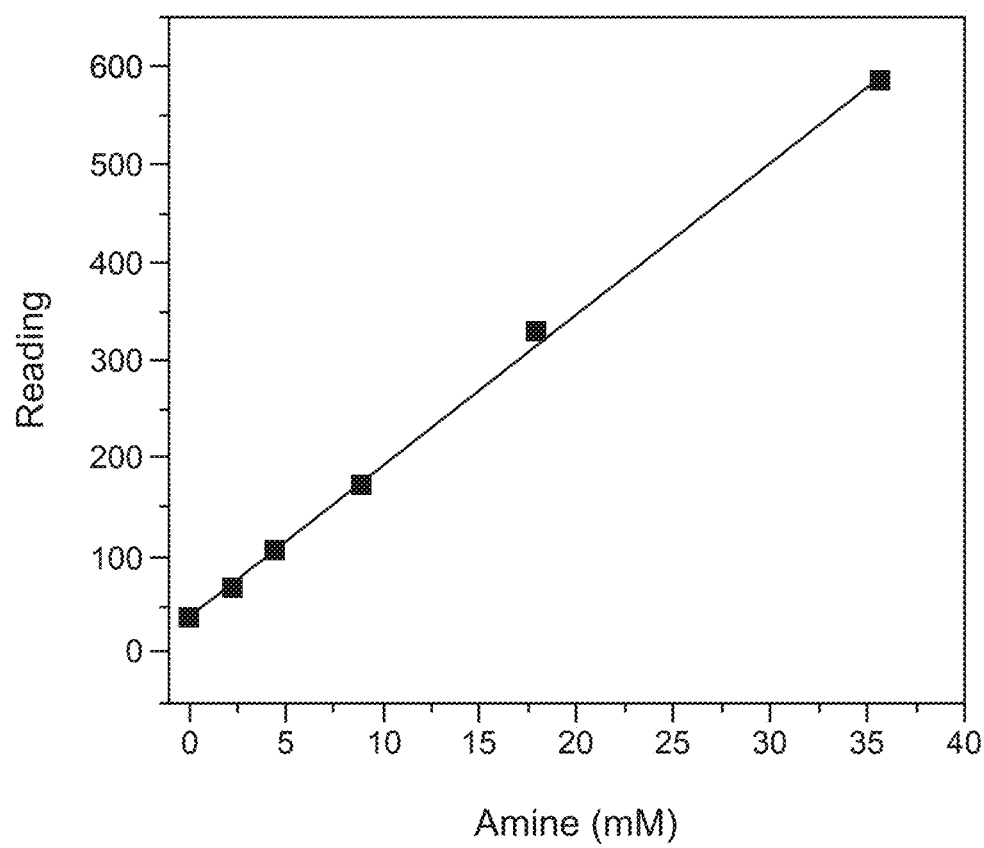
FIG. 32 shows a calibration curve of primary amine concentration at excitation and emission wavelengths of 410 and 480 nm, respectively, according to embodiments of the present disclosure.

A preliminary study of the reaction of amine ligands with polyP at 37° C. demonstrated that primary amine levels decreased around 75% after 24 hours of reaction, indicating a 75% reaction completion of amine with polyP. However, the level of primary amine increased to approximately half of its control concentration after 48 hours which suggested that bonds may have hydrolyzed. The concentration of amine in the control at 37° C. did not substantially change, which may indicate that the difference in the reaction amine concentration cannot be explained by the assay itself (FIG. 31). A calibration curve of primary amine concentration at excitation and emission wavelengths of 410 and 480 nm, respectively, is shown in FIG. 32.

Figure 33:
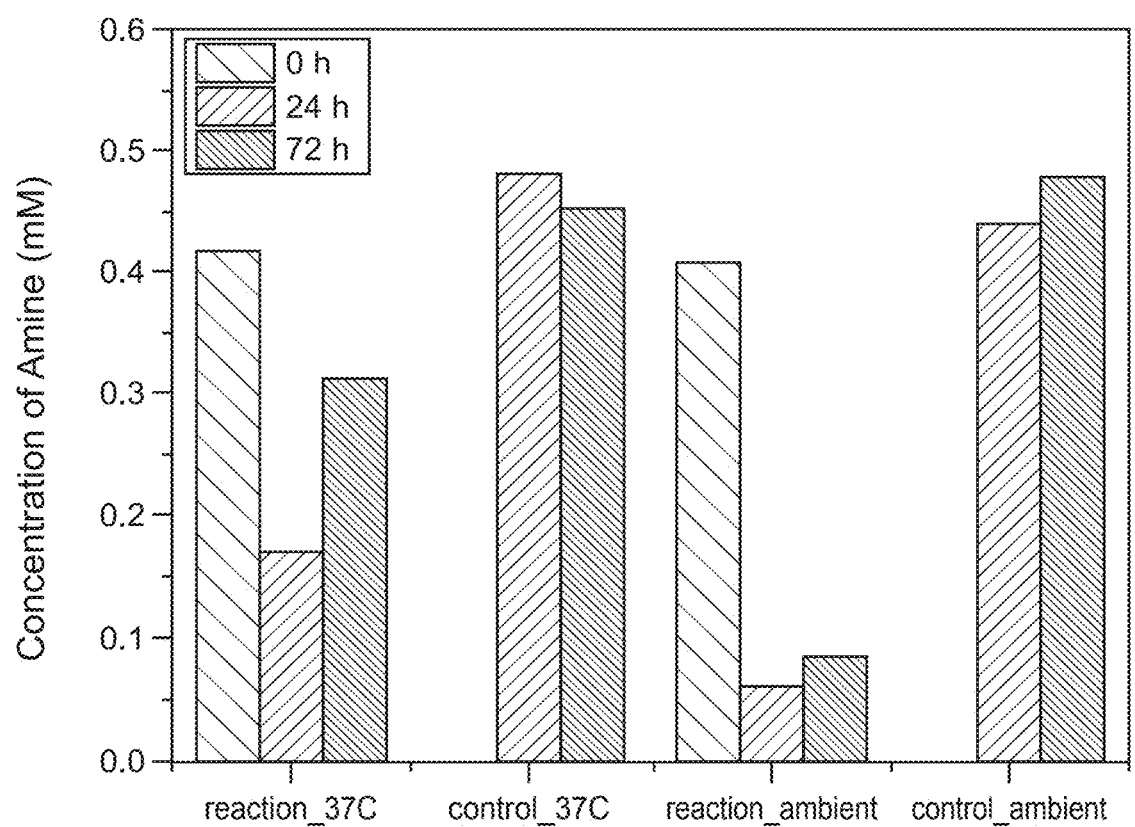
FIG. 33 shows a graph of primary amine concentration after the amine-thiol ligand reacted with polyP, according to embodiments of the present disclosure.

The thiol-amine ligand reaction with polyP at room temperature was shown to have been completed between 75% to 80% of the ligands in solution. FIG. 33 details the results of the reaction optimization. The concentrations in the above reaction scheme except with a 0.42 mM concentration of amine bound ligand, yielded approximately a 5:1 ratio of polyP chains to amine. Comparing the reactions performed at 37° C. with the ones performed at room temperature indicated that the bonds of the amine-polyP hydrolyzed at 37° C. over time. Therefore, both reactions had similar efficiencies and after 72 hours at room temperature more than 75% amine was consumed.

Figure 34:
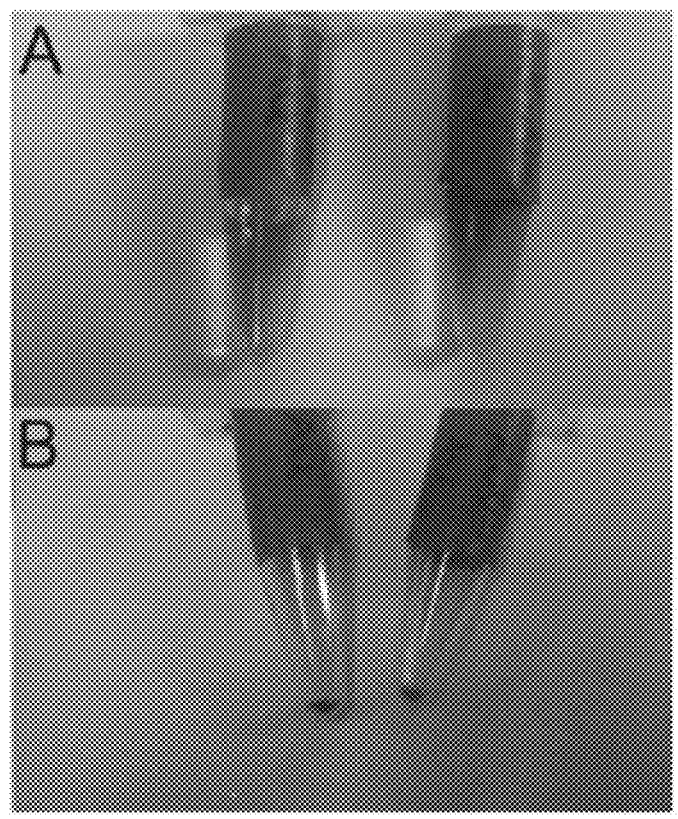
FIG. 34, panel A, shows the gold nanoparticles ligand mixture before centrifugation, according to embodiments of the present disclosure.

Different ratios of polyP to amine were tested, which may affect the final ratios of amine-thiol ligand to the polyP-thiol ligand. The completed reactions mixed with gold nanoparticles were pelleted after centrifugation (FIG. 34).

Modification of the gold nanoparticles may also be performed, such as, but not limited to: (1) producing various particle sizes; (2) modifying with other reaction mechanisms; and (3) separation and purification. To demonstrate that the core material does not substantially affect the clotting kinetics, experiments may be performed to: (1) compare the gold-polyP conjugates with other particles, and (2) crosslink a thin polymer layer and then dissolve the gold.

Particle Design and Tests

Experiments were performed to design and synthesize solid and porous nanoparticle materials that exhibit biocompatibility and rapid thrombus formation. In certain embodiments, the nanoparticles restricted activity to a local region of above-threshold coagulation activity. Experiments were performed on two nanoparticles—procoagulant silica and medical implant compatible titania. The nanoparticle scaffolds were functionalized with a procoagulant compound—thrombin, tissue factor, or polyP—to form a threshold-switchable particle (TSP) that further promoted clot formation. Thrombin, a protein in the coagulation cascade, has a hydrodynamic radius of roughly 8.4 nm. A porous nanoparticle with a minimum pore size of 10 nm can be loaded thrombin. Characterization of the particles included microscopy, zeta potential, dynamic light scattering, and other tests. Thromboelastography (TEG) plasma clotting experiments were used to study the procoagulant activity of functionalized and un-functionalized nanoparticles introduced to recalcified pooled normal plasma (PNP).

Silica Nanoparticle Synthesis—Mesocellular Foam

Experiments were performed to synthesize a porous nanoparticle with a diameter smaller than 200 nm and a pore size greater than 20 nm. A nanoparticle of this size may facilitate a reduction in organ damage, while being able to transport and deliver thrombin and other coagulation factors.

Experiments were performed to synthesize a mesoporous mesocellular foam with a 26 nm pore size (MCF-26) and particle diameter below 1 μm. Mesocellular foams (MCF) with pore sizes of 11.2 nm, 24.3 nm, and 30.9 nm pore size were created. The foams were characterized using BET. Window size was determined from desorption isotherms using the Broekhoff-de Boer (BdB) method; pore size from the adsorption isotherm using the same BdB method. Particle diameters were measured using scanning electron microscopy (SEM) imaging. The experiments demonstrated the ability to precisely define pore sizes in the range desired for enzyme and large biomolecule delivery using a particle size <200 nm, which may be useful for cardiovascular delivery.

A second synthesis procedure was used for the synthesis of flocculated mesoporous silica (FMS) particles with nanofiber or nanosphere morphology (FMS-nf, FMS-ns). FMS-nf and FMS-ns were chosen to synthesize nanoparticles under 200 nm. Dynamic light scattering indicated a particle size of 250+/−50 nm. Capping and coagulation experiments were carried out using FMS silica nanoparticles.

Figure 35:
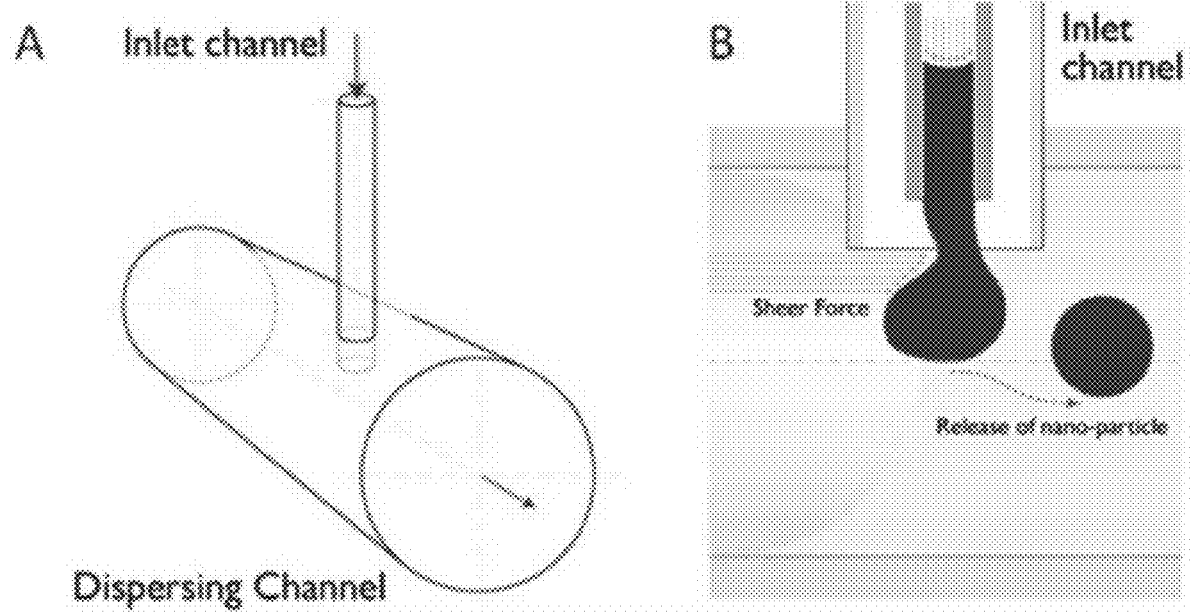
FIG. 35, panel A, and FIG. 35, panel B, show a schematic of the PLGA-based silica nanoparticle synthesis, according to embodiments of the present disclosure.

These two procedures used solution sol gel or colloidal silica precursors. The silica synthesis methodology was based on the poly(lactic-co-glycolic acid) (PLGA) method for drug delivery as shown in FIG. 35, panel A, and FIG. 35, panel B. The silica synthesis procedure used trimethylbenzene (TMB) and $NH_4F$ used in the MCF synthesis; and a triblock copolymer, P123, combined with a cationic surfactant, CTAB, to create a liquid silica precursor. Using this approach, silica particles with average nanoparticle diameters of 125+/−25 nm were synthesized. The 18.2 nm pore size was sufficient for embedding thrombin.

Figure 36:
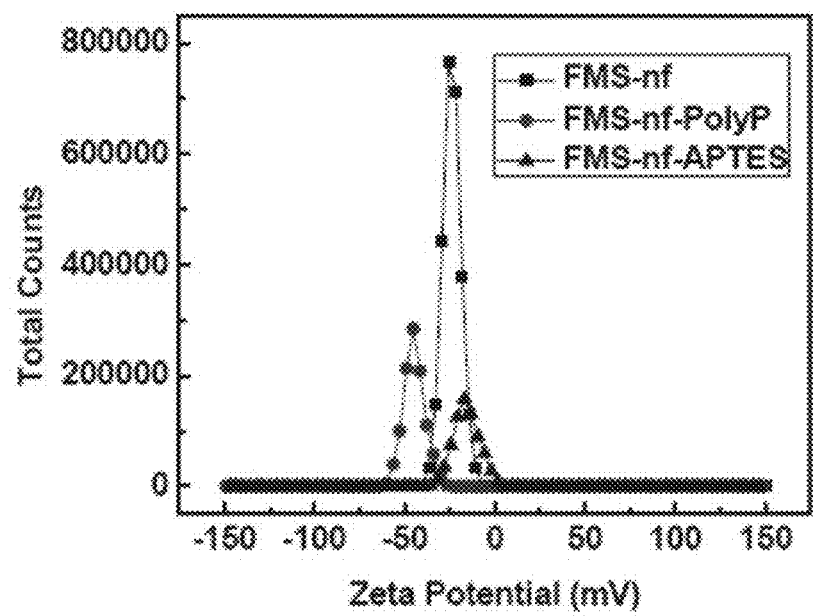
FIG. 36 shows a graph of zeta potentials of FMSnf, FMS-nf loaded with polyP, and FMS-nf loaded with APTES particles, according to embodiments of the present disclosure.
Figure 37:
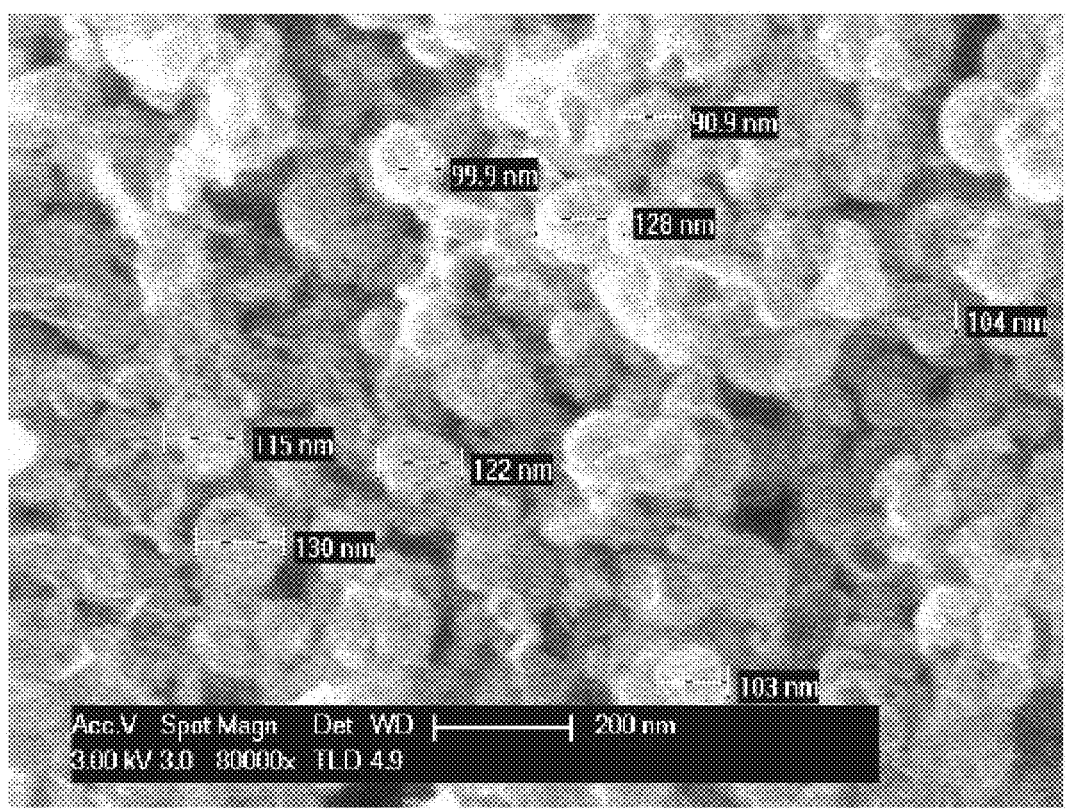
FIG. 37 shows scanning electron microscopy (SEM) images of silica nanoparticles (NPs), e.g., mesocellular foam, prepared using the PLGA system, according to embodiments of the present disclosure. Average particle diameter was 125+/−25 nm as determined by dynamic light scattering. The conjoined nature of the separate particles occurred due to sputtering for SEM imaging.
Figure 38:
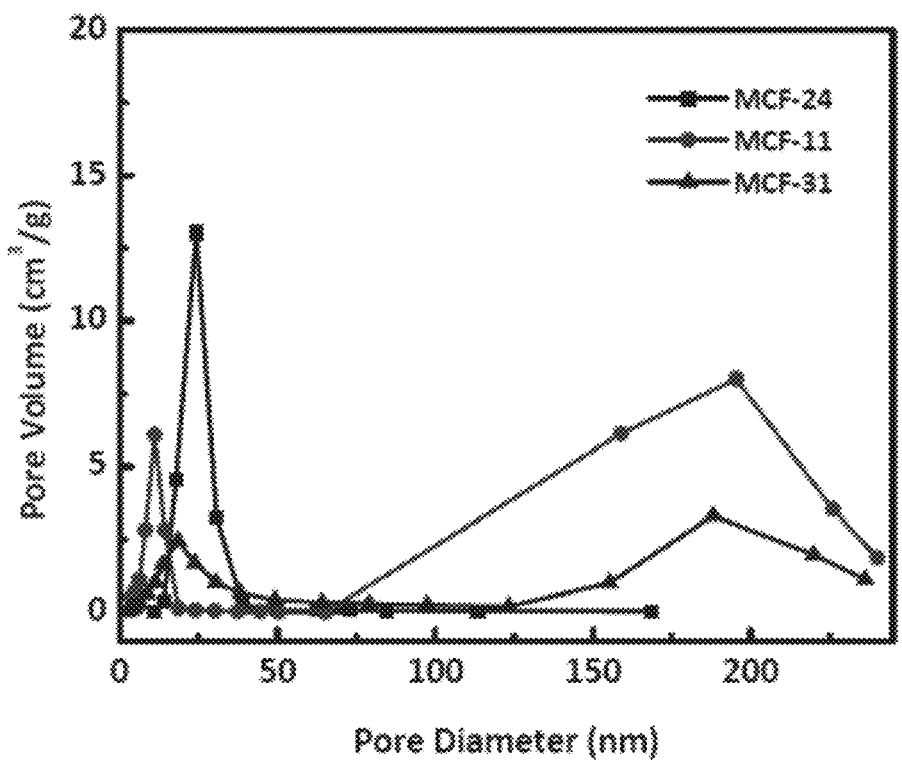
FIG. 38 shows a graph of pore size distribution of mesocellular foams calculated desorption branch by BJH method, according to embodiments of the present disclosure.
Figure 39:
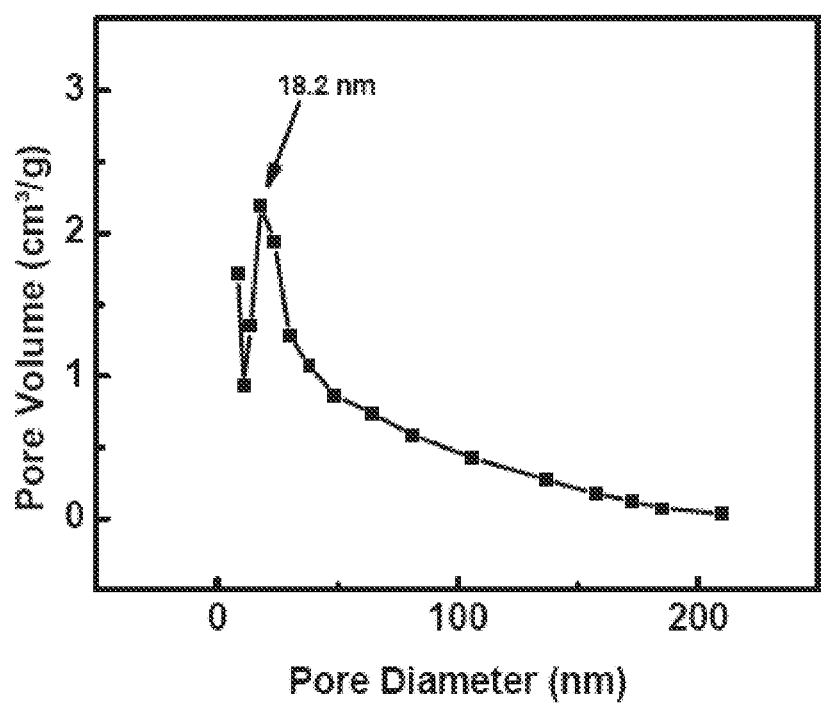
FIG. 39 shows a graph of pore size distribution of porous silica calculated desorption branch by BJH method, according to embodiments of the present disclosure.
Figure 40:
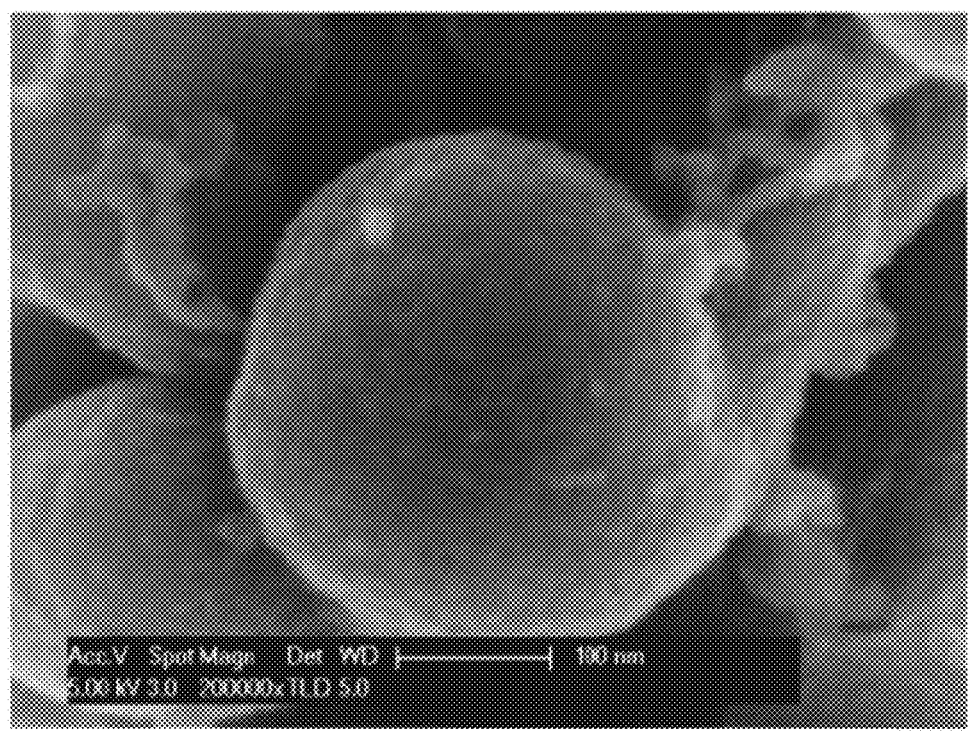
FIG. 40 shows SEM images of $TiO_2$ synthesized via the phosphoric acid pathway, according to embodiments of the present disclosure. The conjoined nature of the separate particles occurred due to sputtering for SEM imaging.
Figure 41:
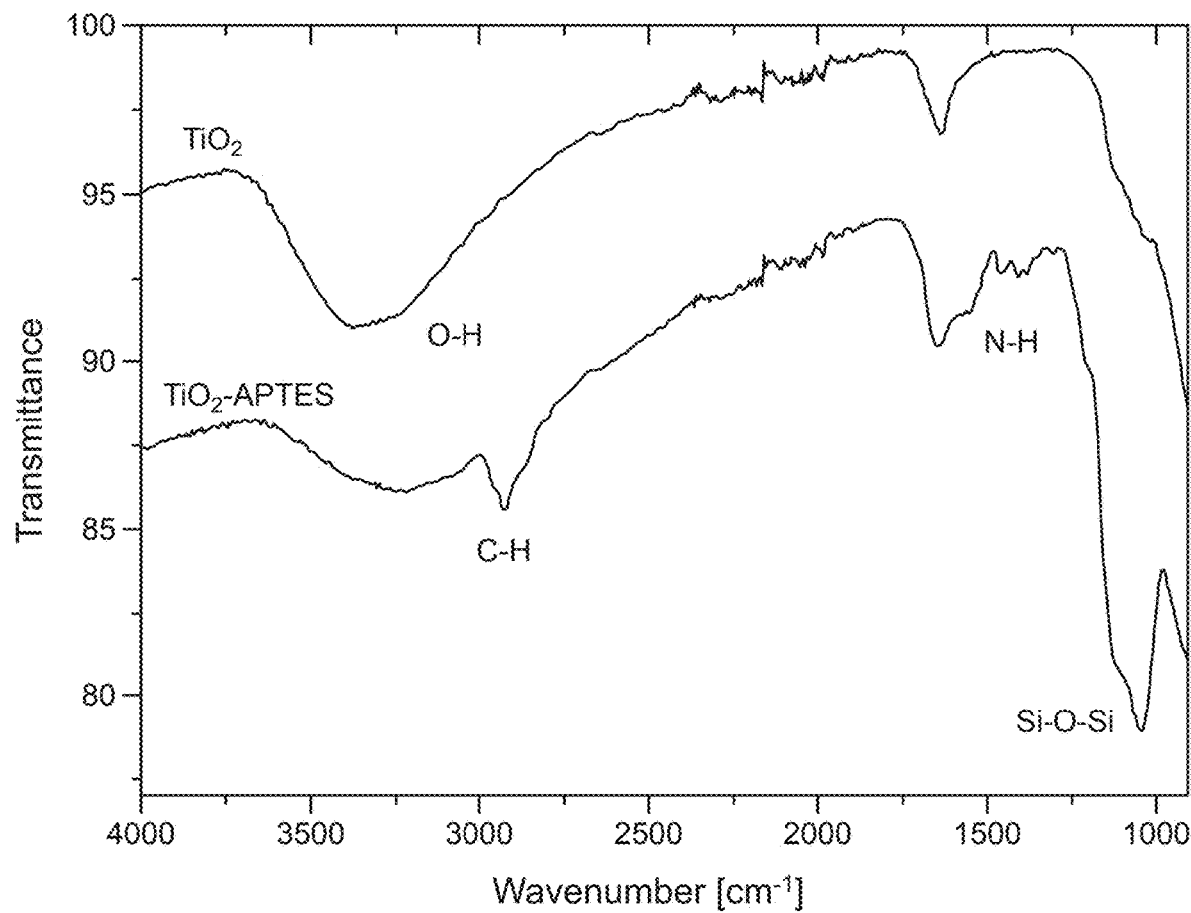
FIG. 41 shows a FT-IR spectrum of unmodified and APTES-modified titania nanoparticles, according to embodiments of the present disclosure. C—H, N—H, and Si—O—Si bands indicated successful attachment of APTES to $TiO_2$ molecules.
Figure 42:
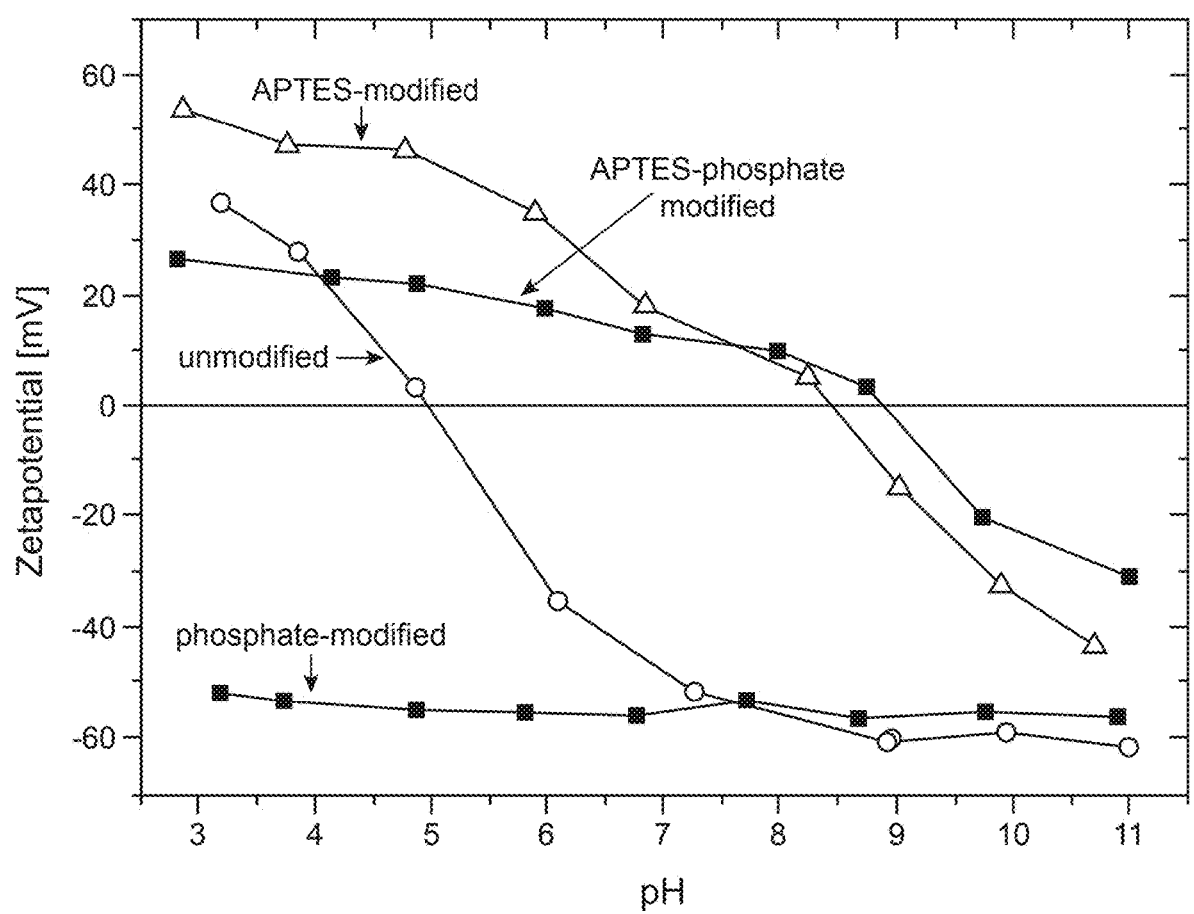
FIG. 42 shows a graph of zeta potential titration of unmodified and modified titania nanoparticles, according to embodiments of the present disclosure.
Figure 43:
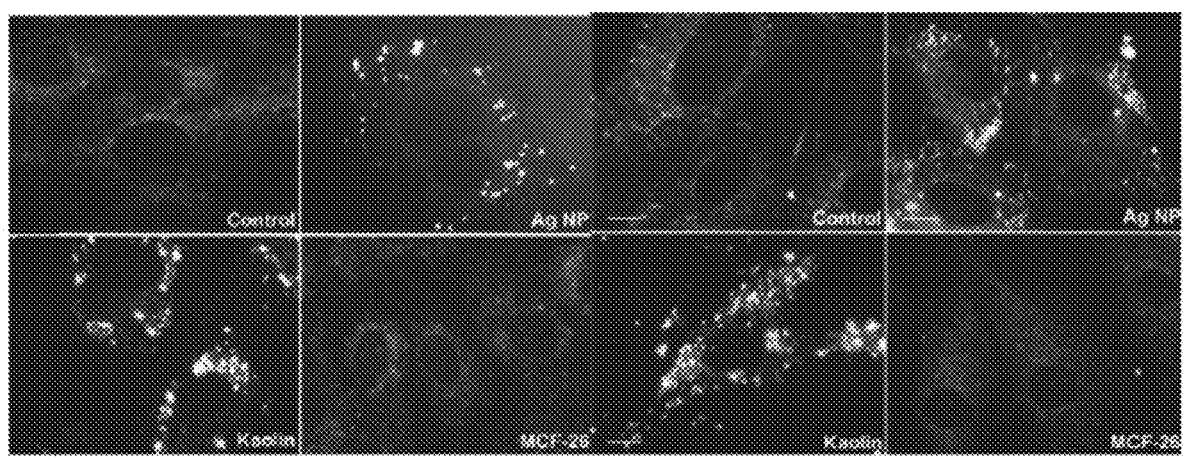
FIG. 43, left, shows images of the uptake of various samples by HUVEC (Human Umbilical Vein Endothelial Cells), with Ag NP concentration of 10 μg/ml; Kaolin concentration of 10 μg/ml; and MCF-26 concentration of 100 μg/ml.

Nitrogen adsorption/desorption isotherms and pore size distribution for all three mesocellular foams were analyzed. FIG. 36 shows the x-ray diffraction pattern and FIG. 37 shows the scanning electron microscopy images for MCF-24. FIG. 38 shows a graph of pore size distribution of mesocellular foams calculated desorption branch by BJH method. FIG. 39 shows a graph of pore size distribution of porous silica calculated desorption branch by BJH method. Finally, Table 1 lists the properties for all three mesocellular foams.

TABLE 1

Textual properties of synthesized mesocellular foams

| MCF Sample | BJH Window Size (nm) | BJH Cell Size (nm) | BET Surface Area (m$^2$/g) | Pore Volume (cm$^3$/g) |
|---|---|---|---|---|
| MCF-11 | 11.2 | 19.3 | 591.7 | 1.7 |
| MCF-24 | 24.3 | 39.3 | 321.0 | 2.4 |
| MCF-31 | 30.9 | 42.4 | 222.4 | 1.6 |

Titania Nanoparticle Synthesis

The use of solid silica and titania nanoparticles as carriers may also facilitate a restriction of coagulation activity to a localized threshold region. Solid silica nanoparticles with particle diameters between 5-100 nm may be synthesized. Capping procedures can be used to bind polyP and coagulation factor proteins to the nanoparticle surface. Solid silica nanoparticles with defined system residence times, polyP and thrombin loadings may facilitate a restriction of their activity to a local region of above-threshold coagulation activity.

Titania nanoparticles were synthesized via a phosphoric acid pathway and characterized using SEM and X-ray diffraction. The particle diameters averaged 225+/−50 nm. Along with the silica FMS, titania particles were used in functionalization studies.

FIG. 40 shows SEM images of $TiO_2$ synthesized via the phosphoric acid pathway. The conjoined nature of the separate particles occurred due to sputtering for SEM imaging.

PolyP Capping

Experiments were performed on two polyP capping pathways. The first pathway utilized the Lewis acid properties of both silica and titania. The process of Lorenz et al., *Anal. Biochem.*, 1994, 216:118-26, was adapted by replacing zirconia with either silica or titania. The negative shift in zeta potential illustrated in FIG. 36 indicated that polyP successfully bound to its target.

The second pathway used (3-aminopropyl)-triethoxysilane (APTES) to form a bridge between the nanoparticle and the procoagulant material. The primary amine terminus of APTES bound with proteins or EDAC-modified polyP. PolyP bound to amine surface strip wells using EDAC, polyP, APTES-modified silica, and 2-(N-morpholino)ethanesulfonic acid (MES). Zeta potential and Fourier transform infrared (FTIR) spectroscopy showed that the nanoparticles had been functionalized with APTES. Zeta potential measurements were used to determine that the polyP bound to the particles. FIG. 41 shows a FT-IR spectrum of unmodified and APTES-modified titania nanoparticles. C—H, N—H, and Si—O—Si bands indicated successful attachment of APTES to $TiO_2$ molecules. FIG. 42 shows a graph of zeta potential titration of unmodified and modified titania nanoparticles.

Protein Capping

Experiments were performed for capping solid nanoparticles with thrombin using the APTES mechanism described above. The mechanism involved binding a slowly deprotected thiol on the APTES-nanoparticle scaffold to the thiol-reactive group on the protein. This pathway may minimize aggregation of particles and proteins due to a fast reaction rate that would result in one particle binding to one protein.

Other active agents can be integrated with the nanoparticles to treat internal wounds. For example, a tissue factor (TF)-Nanodisc agent can be used to initiate coagulation. In addition, delivering additional fibrinogen to a wound site can replenish the fibrinogen concentration and may lead to a stronger clot.

Thromboelastography

Several silica samples—both naked and polyP capped—were tested for procoagulant activity using plasma in a thromboelastograph (TEG) instrument. The TEG measurement focused on four coagulant parameters: R, time until first clot; K, time from initial clot formation to 20 mm clot diameter; α, clot formation speed; MA, clot strength. As listed in Table 2, these data indicated that the polyP-capped silica decreased the time and speed of clot formation.

TABLE 2

TEG measurements for controlled pooled normal plasma, FMS-ns, and polyphosphate-modified FMS-ns.

| Run | R (min) | K (min) | Angle (deg) | MA (mm) |
|---|---|---|---|---|
| Control Average | 13.40 | 3.70 | 55.63 | 37.77 |
| Control St. Dev. | 1.28 | 0.36 | 7.75 | 8.35 |
| FMS-ns Average | 7.98 | 1.98 | 63.93 | 31.25 |
| FMS-ns St. Dev. | 0.67 | 0.95 | 12.19 | 6.43 |
| FMS-ns-PolyP Average | 7.03 | 1.30 | 77.63 | 28.43 |
| FMS-ns-PolyP St. Dev. | 0.50 | 0.46 | 3.52 | 2.32 |

Biocompatibility

Experiments were performed to examine the cytotoxicity of MCF-26 on human cells. Experiments were performed to test MCF-26 absorption by HUVEC (Human Umbilical Vein Endothelial Cells), HEK-a (Human Embryonic Kidney), HDF-a (Human Dermal Fibroblast), HPTC (Human Renal Proximal Tubule), HK-2 (Human Kidney 2), and NIH-3T3 fibroblast cells. The cytotoxicity studies showed that MCF-26 nanoparticles are not toxic, even at high concentrations. Typically, silica particles have IC50 values in the μg/ml concentration range. Even for the highly sensitive HUVEC cells, MCF-26 IC50 values ranged between 0.7-6.3 mg/ml. Cells did not readily absorb MCF-26 particles until the concentrations reached the mg/ml scale. FIG. 43, left, shows images of the uptake of various samples by HUVEC (Human Umbilical Vein Endothelial Cells), with Ag NP concentration of 10 μg/ml; Kaolin concentration of 10 μg/ml; and MCF-26 concentration of 100 μg/ml. FIG. 43, right, shows images of the uptake of various samples by HDFs, with Ag NP concentration of 20 μg/ml; Kaolin concentration of 20 μg/ml; and MCF-26 concentration of 100 μg/ml. Table 3 shows IC50 (mg/ml) and % viability values of neural red uptake assay of MCF-26.

TABLE 3

Neural red uptake assay values for MCF-26.

| Cell Type | IC50 (mg/ml) | % Viability at $C_{max}$ = 7 mg/ml |
|---|---|---|
| HUVEC 5117 | 6.3 ± 0.2 | 50% ± 3.4% |
| HUVEC 5025 | 2.1 ± 0.8 | 26.6% ± 6.7% |
| HUVEC 3516 | 0.7 ± 0.0 | 20.8% ± 2.0% |
| HDF-a (ScienCell) | 2.0 ± 0.2 | 13.4% ± 2.8% |
| HDF-a (PromoCell) | 5.6 ± 1.4 | 39.5% ± 8.0% |
| HDF-a (ATCC) | 5.0 ± 0.7 | 41.4% ± 3.1% |
| HEK-a 6940 | >7.0 | 91.9 ± 8.6% |
| HEK-a 6937 | >7.0 | 59.8% ± 4.4% |
| HEK-a 6539 | >7.0 | 77.5% ± 3.1% |

In summary, the above experiments demonstrated: clotting was stimulated up to 4-fold by activating pairs of clotting factors, with no further stimulation using three activating pairs of clotting factor; PAMAM dendrimer-based, polyP-containing procoagulant nanoparticles were synthesized and tested for stability and activity; polyP-containing polystyrene procoagulant nanoparticles were synthesized and tested for stability and activity; polyP-containing gold procoagulant nanoparticles were synthesized and tested for stability and activity; the synthesized nanoparticles had a 125+/−25 nm particle diameter and 18.2 nm pore size; porous silica was determined to be biocompatible with human cells; particle synthesis procedures for delivery of thrombin, which has a hydrodynamic radius of 8.4 nm, were developed; titania particles with 225+/−50 nm average diameter were synthesized; polyP chains were attached to silica and titania nanoparticles using Lewis acid-base chemistry and APTES-EDAC mechanism; and procoagulant activity of silica and polyP-bound silica were quantified.

Example 3

Experiments were performed on solid silica nanoparticles ranging from 10-150 nm in diameter. The silica acted as a scaffold upon which the procoagulant agents attached. Particles of this size can flow through small vessels in the blood stream.

Gold nanoparticles of 10 nm and 15 nm diameter were selected as base particles in addition to the 5 nm gold nanoparticles that were initially investigated. The maximum numbers of polyphosphate chains that can be added to each particle based on theoretical analysis are: 64 and 144 for the 10 nm and 15 nm gold particle, respectively. The different size particles contained distinct, known numbers of polyphosphate chains. In certain embodiments, nanoparticles bigger than a threshold size with conjugated polyphosphate more than the critical number triggered blood clotting.

Experiments were performed on solid silica nanoparticles under 200 nm as the delivery agent. Polyphosphate was attached to a silica scaffold using the Lewis acid-base properties of silica and polyphosphate. 70 mer length polyphosphate (P70) was used, as this length roughly correlates to the size of polyphosphate secreted by human platelets during clotting.

Figure 44:
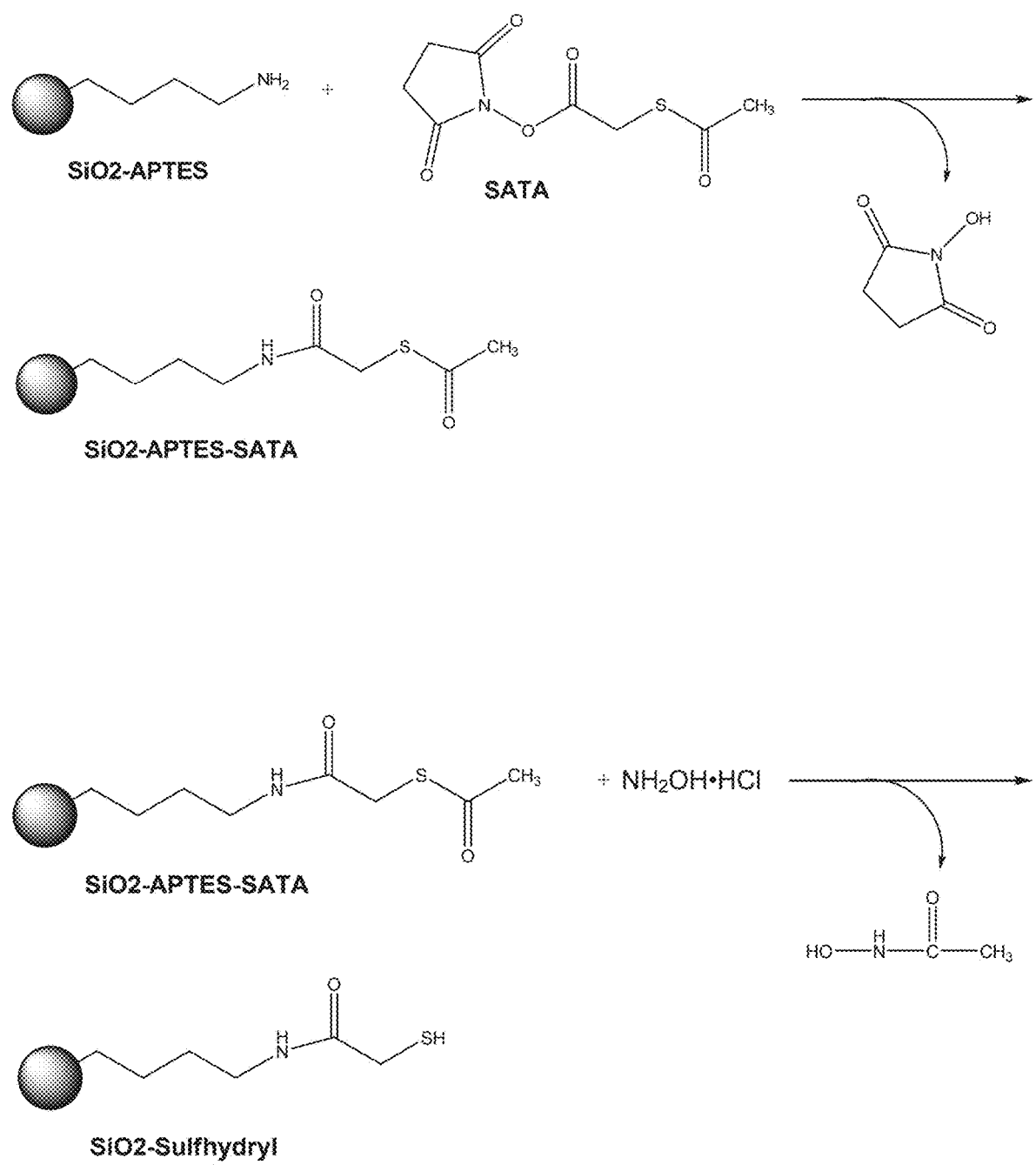
FIG. 44 shows a mechanism for attaching thrombin to solid silica using a protein cross-linker, according to embodiments of the present disclosure.

Additionally, thrombin was attached to solid silica using a protein cross-linker. The mechanism for attachment is shown in FIG. 44. By functionalizing silica with 3-Aminopropyltriethoxysilane (APTES), the silica acted as a protein for cross-linking purposes.

Figure 45:
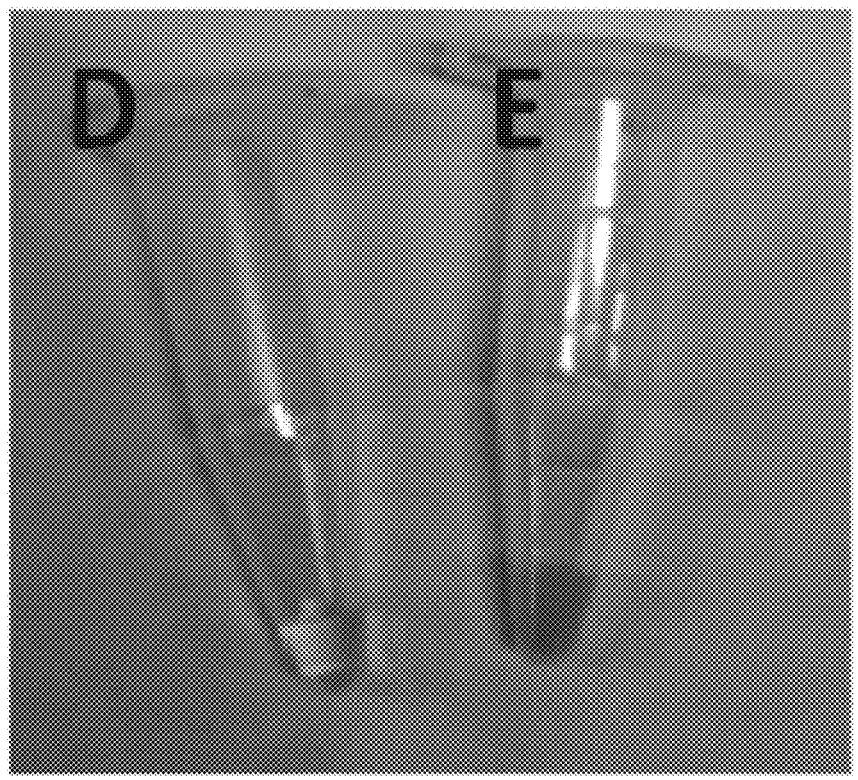
FIG. 45 shows a process work flow and image of a thiol sensing colorimetric assay to verify hydroxylamine deprotection of solid silica nanoparticles, according to embodiments of the present disclosure.

Experiments were performed to test solid silica nanoparticles with covalent linkages to the coating. The first system was polyphosphate attached datively to bare oxide or covalently to aminopropyl terminated silica nanoparticles. The second was a linker system for protein and/or peptide coupling. The coupling results used a protected thioacetyl coating on the particles and a thiol reactive ortho-pyridyl disulfide (OPSS) carried on lysines of the protein. Hydroxylamine deprotection of the particles was verified using the thiol sensing colorimetric assay (FIG. 45). OPSS-thrombin and dye-labeled albumin-OPSS serve as model proteins (FIG. 44). Silica-thioacetyl was prepared in two steps from silica. Thiol deprotection was verified by 5,5'-Dithiobis(2-nitrobenzoic acid) (DTNB). Sample D had reagents but no silica, and in sample E, silica-SATP generated intense color indicating successful deprotection.

Polyphosphate polymers of a wide variety of polymer lengths were prepared by large-scale preparative electrophoresis for size-fractionating polyphosphate. These materials were used as one of the procoagulant payloads for the nanoparticles. In some instances, the procoagulant activity may depend on the polyphosphate polymer lengths. Linking chemistries for covalently attaching polyphosphate to targeting molecules and nanoparticles included indirect coupling by first attaching polyamines to the terminal phosphates, and then using amine-reactive probes to link to the terminal amino groups.

The same reaction scheme was used to conjugate polyphosphate onto gold nanoparticles. Ratios of the reactants (thiol-polyphosphate to gold nanoparticles) and gradients of solution ionic strength were varied to produce maximum conjugation of polyP onto gold particles (5 nm, 10 nm, and 15 nm). Separation of the conjugates from free polyphosphate was performed by centrifugation. Centrifugation was tested at various polyP and gold nanoparticle concentrations to (1) remove free polyphosphate efficiently; (2) prevent particle aggregation; and (3) to minimize loss of gold nanoparticles. After the reaction between thio-bound polyphosphate and gold nanoparticles, as well as after centrifuging, TEM images were taken to determine whether smaller non-visible aggregates had formed. The images indicated that aggregation pre-centrifugation was minimal with a small percentage of 2 and 3 particle clusters.

Experiments showed that a roughly 250 nm solid silica nanoparticle bound to polyphosphate accelerated clotting compared to recalcified plasma using thromboelastography (TEG). Experiments were performed to further quantify the procoagulant activities of silica, polyphosphate, and polyphosphate bound to silica. Various sizes and concentrations of silica were tested. P70 was bound onto a smaller silica scaffold. Even at a mg lower concentration, the silica-P70 TSP showed a decrease in R time by about 0.5 min.

Experiments were performed to test the procoagulant activity of polyphosphate in solid and solution phases without a scaffold attachment. The tests showed increased clotting times and weakened clot strength when compared to recalcified plasma, which indicated that the polyphosphate of relatively short polymer sizes may be attached to a scaffold to function as a procoagulant. Attaching multiple copies of these shorter polymers to the same nanoparticle may allow a localized assembly of multiple clotting proteins similar to what would be observed with a single, long polyphosphate polymer.

Example 4

Experiments were performed on silica nanoparticles (SNPs). The silica acted as a scaffold upon which the procoagulant agents attached. Particles of the studied size can flow through the smallest vessels in the blood stream. Silica nanoparticles between 1-10 nm and 50-150 nm were tested.

The effect of the silica particles' size and concentration on coagulation was measured. Particles above 50 nm were synthesized in the laboratory following a modified Stöber method (Stober W., et al., *J. Colloid & Interface Sci.*, 26(1), 62-69) and recovered using centrifugation. The different nanoparticle sizes were obtained by varying the amounts of tetraethoxysilane (TEOS) and ammonia. Sigma Aldrich supplied Ludox silica nanoparticles below 10 nm. Silica nanoparticles below 50 nm were isolated by ultrafiltration and ultracentrifugation.

Figure 46:
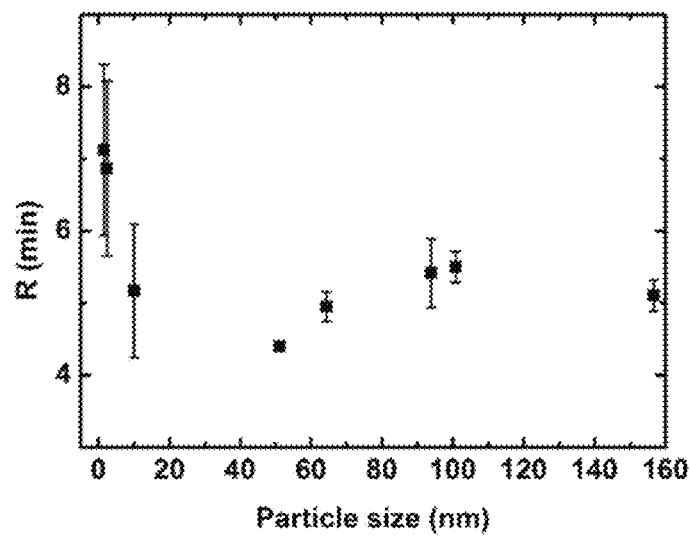
FIG. 46 shows a graph of clotting time (R, min) versus particle size (nm) of silica nanoparticles at a concentration of 0.68 mg/mL, according to embodiments of the present disclosure. Experimental conditions: 37° C., 22 mM $Ca^{2+}$.

Size-dependent clotting experiments were performed to compare the various silica particles at a fixed concentration of 0.68 mg/mL, which was defined in other experiments to be in the range of high activity (FIG. 46). A minimum R value, the time to initial clot formation, occurred at a particle size of 55 nm. The 55-nm particles showed an R value of 3 min (FIG. 47), which was suitable for testing surface-attached polyphosphate.

Concentration experiments focused on 55-nm silica particles, tested at concentrations of 0.14 mg/ml, 0.34 mg/ml, 0.68 mg/ml, 1.35 mg/ml, and 2.70 mg/ml. The resulting data (FIG. 47) identified ~0.6 mg/ml bare silica as the threshold for a minimization of R. At this concentration, the R value averaged 3 min. The R value remained near 3 min for double the silica (1.35 mg/ml) and then rose slightly to 3.5 min at 2.70 mg/ml. High concentration may result in aggregation or dilution of plasma factors over the surface area. The particles were stable over a wide concentration range (FIG. 48) and were testing in buffers and high-salt, serum conditions.

The R value was dependent on concentration until the threshold condition was met, over which R remains low and stable.

PolyP45-labeled gold nanoparticles (5 nm, 10 nm, 15 nm, and 50 nm) were separated from free polyP45 by centrifugation. More than 90% of the polyP-labeled gold nanoparticles were recovered and 99% of the polyP45 that was not covalently bound to the particles was removed.

Figure 47:
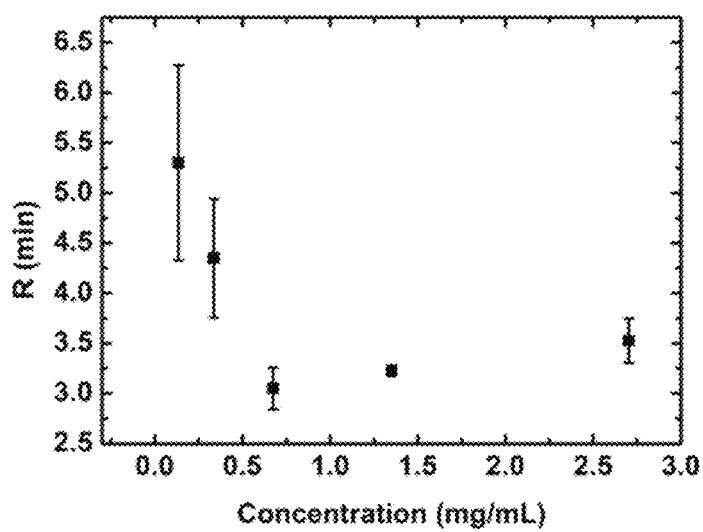
FIG. 47 shows a graph of clotting time (R, min) versus final concentration (mg/mL) of silica nanoparticles of 55 nm size in the TEG, according to embodiments of the present disclosure. 0.68 to 1.35 mg/mL was deemed optimal, with the threshold being ~0.5 mg/mL. Experimental conditions: 37° C., 11 mM $Ca^{2+}$.

As shown in FIG. 47, silica-based surfaces enhanced clotting above a threshold concentration. Different types of coatings were tested. APTES-functionalized silica was used to link with a variety of compounds. Amine functionalization of the surface was used and clotting effects were compared provide a pro-coagulant surface while introducing conjugate handles for attachment of polymers, peptides, or proteins.

Figure 49:
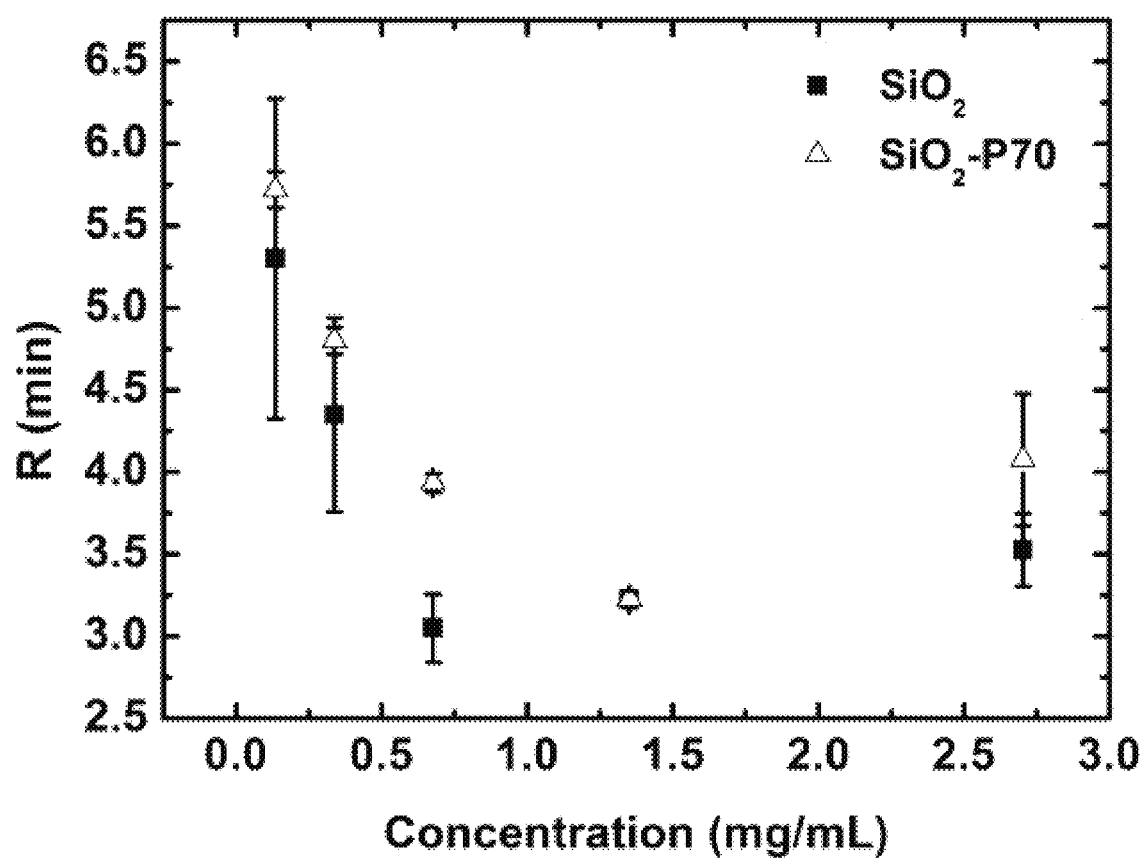
FIG. 49 shows a graph of clotting time (R, min) versus the concentration of silica nanoparticles with and without polyphosphate, according to embodiments of the present disclosure. Experimental conditions: 37° C., weight ratio $SiO_2$:P-70=1:1, 116 nm, 11 mM $Ca^{2+}$.
Figure 50:
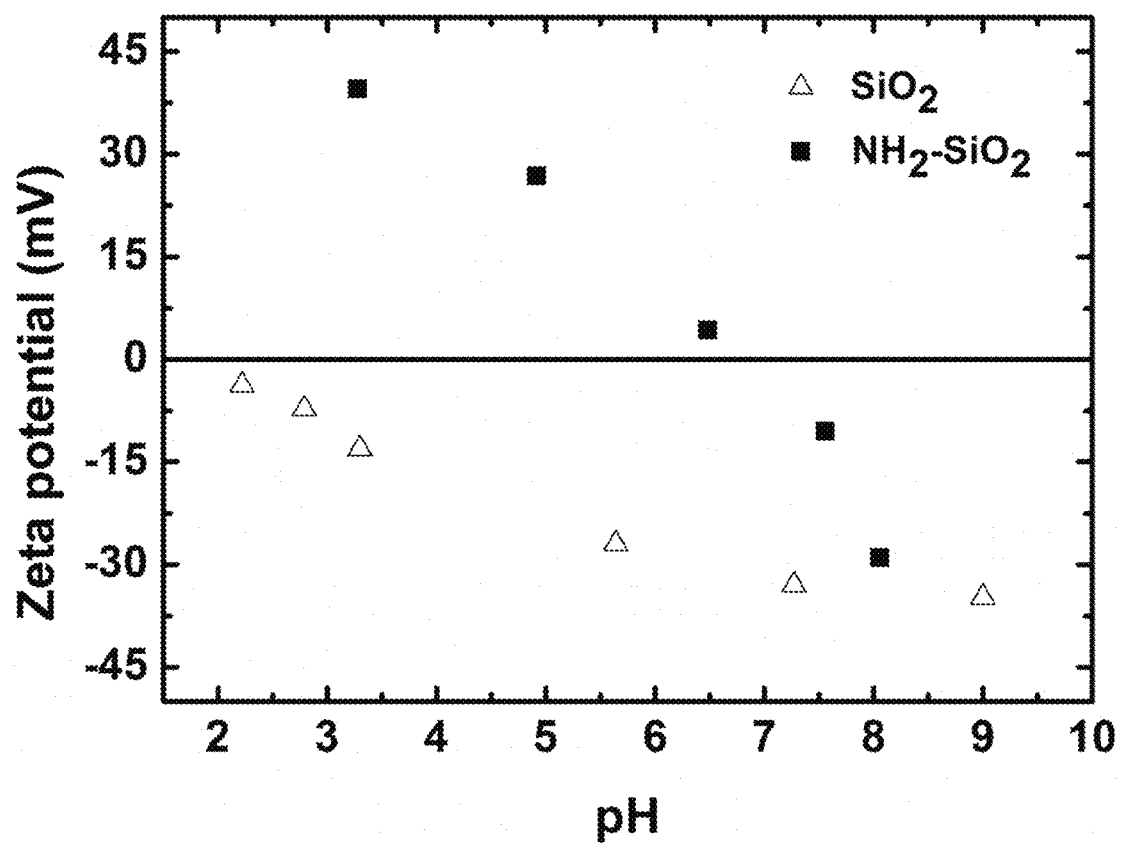
FIG. 50 shows a graph of the relationship between zeta potential and pH for silica particles ones coated with APTES, according to embodiments of the present disclosure. Experimental conditions: 20° C., 12.5 mg/mL, 112 nm diameter, batch was low-amine coated particles.
Figure 51:
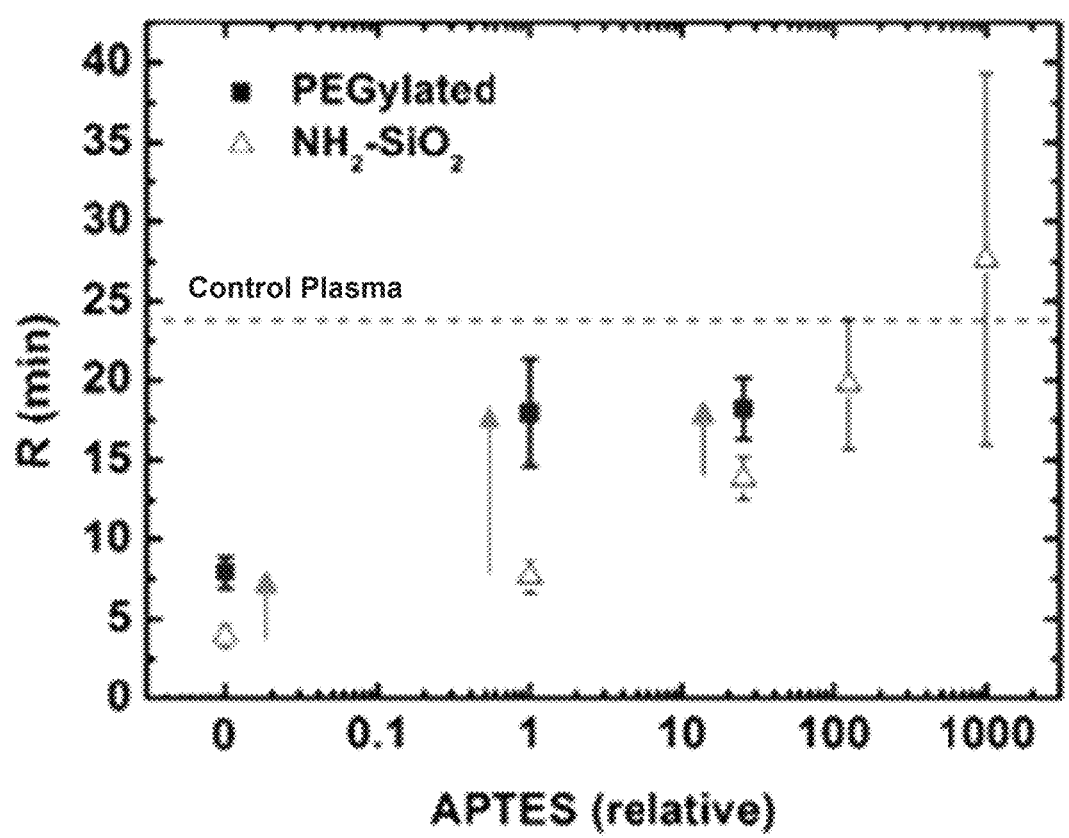
FIG. 51 shows a graph of clotting time (R, min) of the silica particles coated with APTES, with and without amine PEGylation, according to embodiments of the present disclosure. Delta R was optimal at the low amine density. Experimental conditions: 37° C., 1.35 mg/mL, 112 nm.

Silica Nanoparticles (SNP) (FIGS. 46-48)
1) -polyphosphate (FIG. 49)
2) -APTES; Low to high (FIGS. 50 and 51)
   a. -APTES-polyphosphate
   b. -APTES-PEG (FIG. 49)
   c. -APTES-PEG-Peptide
   d. -APTES-link-Peptide
   e. -APTES-link-Peptide-PEG The polyphosphate used in FIG. 49 was a ~70-mer length (P70) that was chosen for its similarity to the size of polyphosphate secreted by human platelets during clotting. P70 directly adsorbed to silica was found to slightly increase the particle size (by several nm). Polyphosphate may be attached to silica via an APTES bridge, based on the covalent derivatization technology for polyphosphate. Silica nanoparticles with APTES are shown in FIGS. 50 and 51. APTES-specific anchoring may yield higher surface density or an improved conformation, e.g., brush anchored by only terminal phosphates.

FIG. 50 shows the clotting factor R for a series of APTES-Silica (SNP—NH$_2$). The polyphosphate can be coupled using EDC, and pH-dependent zeta potential can be monitored relative to the SNP—NH$_2$ starting material as in FIG. 50. The same APTES strategy can be used as a point for attaching PEG, peptides for targeting or enzyme activation, and/or proteins. Reactive linkers can be employed, for example amine reactive NHS-linker-Maleimide or NHS-linker-OPSS for subsequent thiol attachment. Thiols can be carried on the dye-labeled peptides or introduced into proteins using 2-iminothiolane or N-Succinimidyl S-Acetylthiopropionate (SATP).

In certain embodiments, a protease-sensitive coating can be removed once above-threshold conditions are met, e.g., a prothrombinase-sensitive IEGR (SEQ ID NO: 1) peptide linker sequence. The coating may include large-molecular-weight PEGs attached through peptide linkers to a shared silica core nanoparticle, whose surface activity is reduced by the presence of the PEG. Fluorescein-labeled peptides can be used for quantification after coupling. PEG or other passivating polymers may be used to (i) increase the half-life of silica in the blood stream, (ii) reduce cellular uptake, and (iii) reduce protein adsorption to the active, yet hidden surface.

Experiments were performed to test SNPs with and without adsorbed polyp. The SNPs with attached polyP had increased procoagulant activity compared to SNPs without polyP.

Cystamine (a disulfide compound with two terminal primary amines) was conjugated with polyP45 at reaction efficiencies of 90% by buffering the reaction at pH 9 with MES and allowing the reaction to proceed at room temperature for 24 hours. The binding of polyphosphate to cystamine occured via phosphoramidate bond formation between the terminal phosphate and the primary amine. Next, dialysis (MWCO 2000) was used to remove the unreacted cystamine. The conjugate was then added to the gold nanoparticles to replace the citrate. By controlling the reaction time and ionic strength of the suspension, the number of polyP chains conjugated to one nanoparticle can be varied. The following polyP45-Au nanoparticles were synthesized and tested on a coagulometer to measure Factor X-mediated clotting activities, as outlined in Table 4, below:

TABLE 4 polyP45-Au nanoparticles

| Sample Name | NP Diameter (nm) | Contains PEG | MonoP (µM) | Au (nM) | Agg. # | Volume (uL) |
|---|---|---|---|---|---|---|
| 56_10 | 10 | No | 19.48 | 15.5 | 28 | 700 |
| 57_10 | 10 | No | 20.3 | 14.7 | 30.8 | 500 |
| 59_10 | 10 | No | 31.4 | 12.9 | 54.2 | 380 |
| M9_10 | 10 | No | 10.6 | 6.1 | 38.7 | 930 |
| M9_15 | 15 | No | 12.6 | 4.95 | 56.6 | 700 |
| 10_A1D | 10 | No | 10.9 | 11.3 | 21.6 | 210 |
| 10_A1D-2:1peg | 10 | Yes | 9.8 | 16.2 | 13.4 | 250 |
| 15_A1D | 15 | No | 4.96 | 2.61 | 42.2 | 600 |
| 50_A1D | 50 | No | 6.93 | 0.245 | 628 | 100 |
| 10_10 | 10 | No | 53.5 | 17.4 | 68 | 500 |
| 16_10 | 10 | No | 9.8 | 14.7 | 14 | 700 |
| 9_5 | 5 | No | 56 | 56 | 22 | 640 |
| 14_5 | 5 | No | 4.59 | 78 | 1 | 940 |

Figure 52:
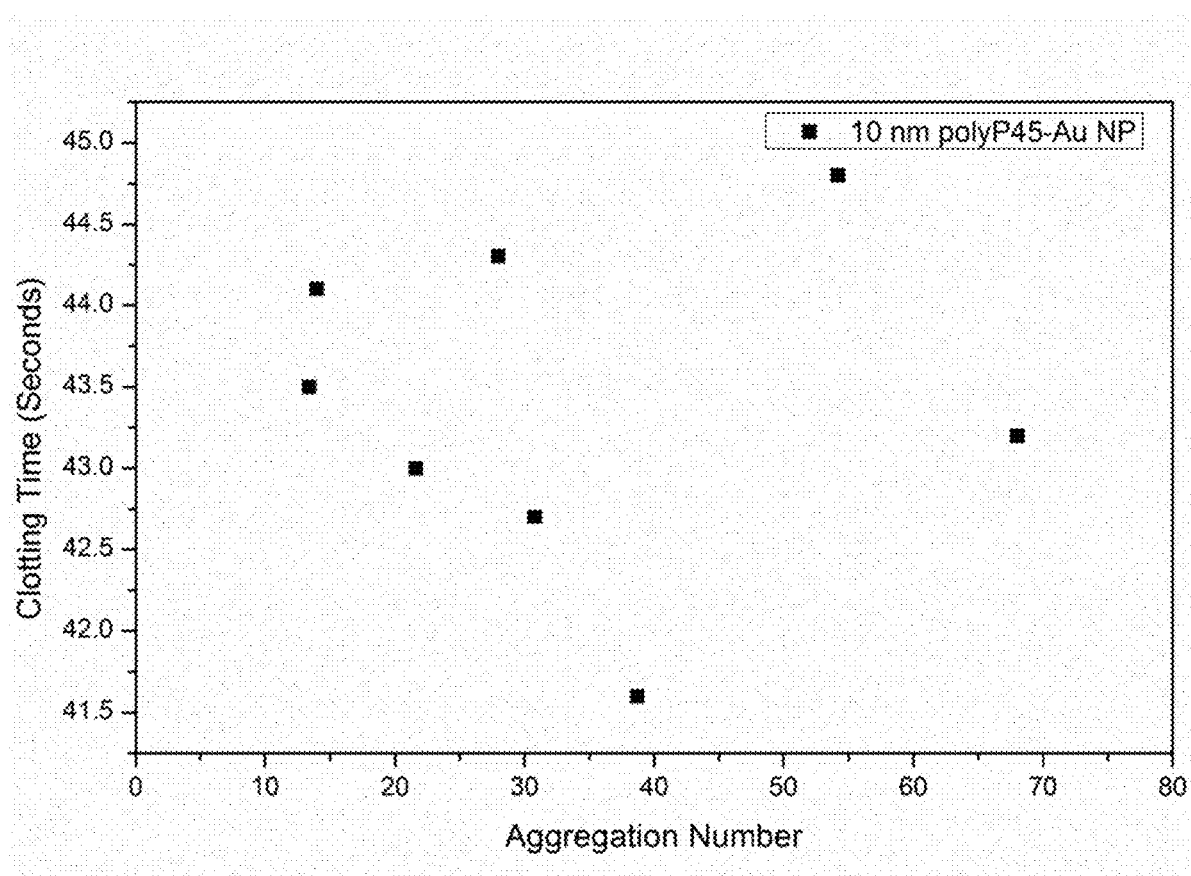
FIG. 52 shows a graph of the effects of polyP45-Au nanoparticles (10 nm) on Factor Xa-mediated clotting time, according to embodiments of the present disclosure. The phosphate concentration was kept at 9.8 μm.
Figure 53:
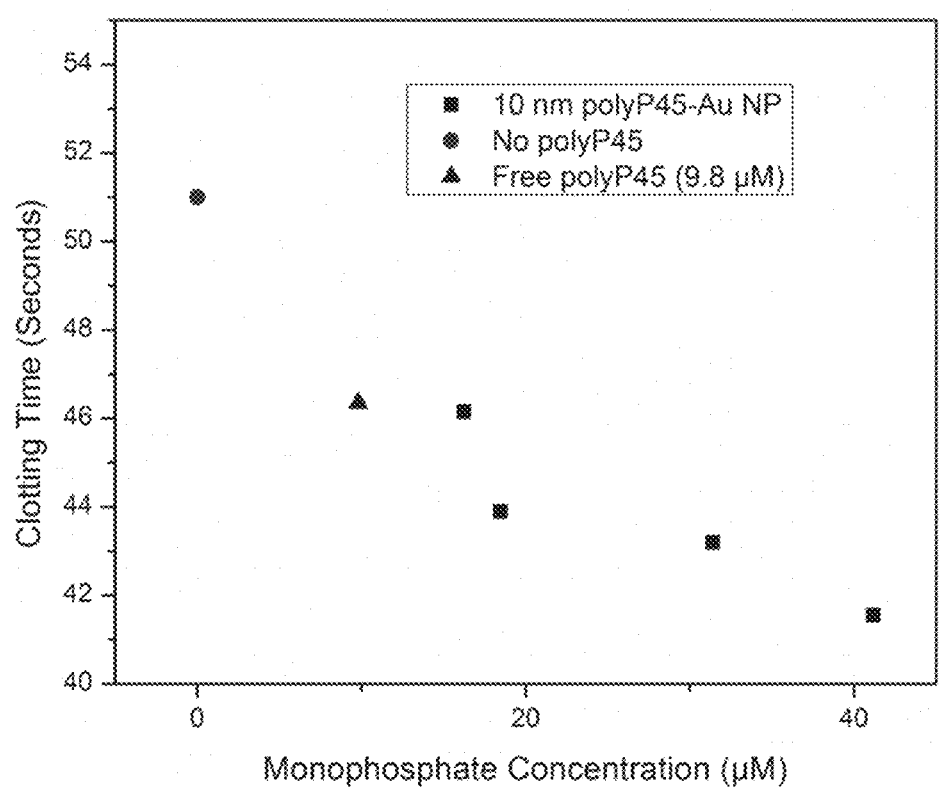
FIG. 53 shows a graph of clot time versus polyphosphate concentration, according to embodiments of the present disclosure. Nanoparticle concentration was 12.9 nM.

Based on the tests of the above samples: (1) there was no correlation between clotting time and aggregation number for 10 nm particles at constant phosphate concentration (9.8 µM) (FIG. 52); and (2) Clotting time depended on phosphate concentration (FIG. 53).

Experiments were performed on mechanisms for attaching polyphosphate (P70) to the surface of solid silica nanoparticles. APTES was used to attach the P70. Conjugation of PEG to the amines modulated the R value. In certain embodiments, proteolytic cleavage could unmask and expose the pro-coagulant surface. For example, enzyme-recognition peptides may be used to hold the PEG to a low-APTES silica. In a reverse orientation, where peptide is on the outer tip of the PEG, the damaged vascular surface, activated cell surfaces, or fibrin may be targeted. Proteins such as thrombin and tissue factor similarly masked by PEG may be carried in a protected form by nanoparticles to the site of interest.

Figure 48:
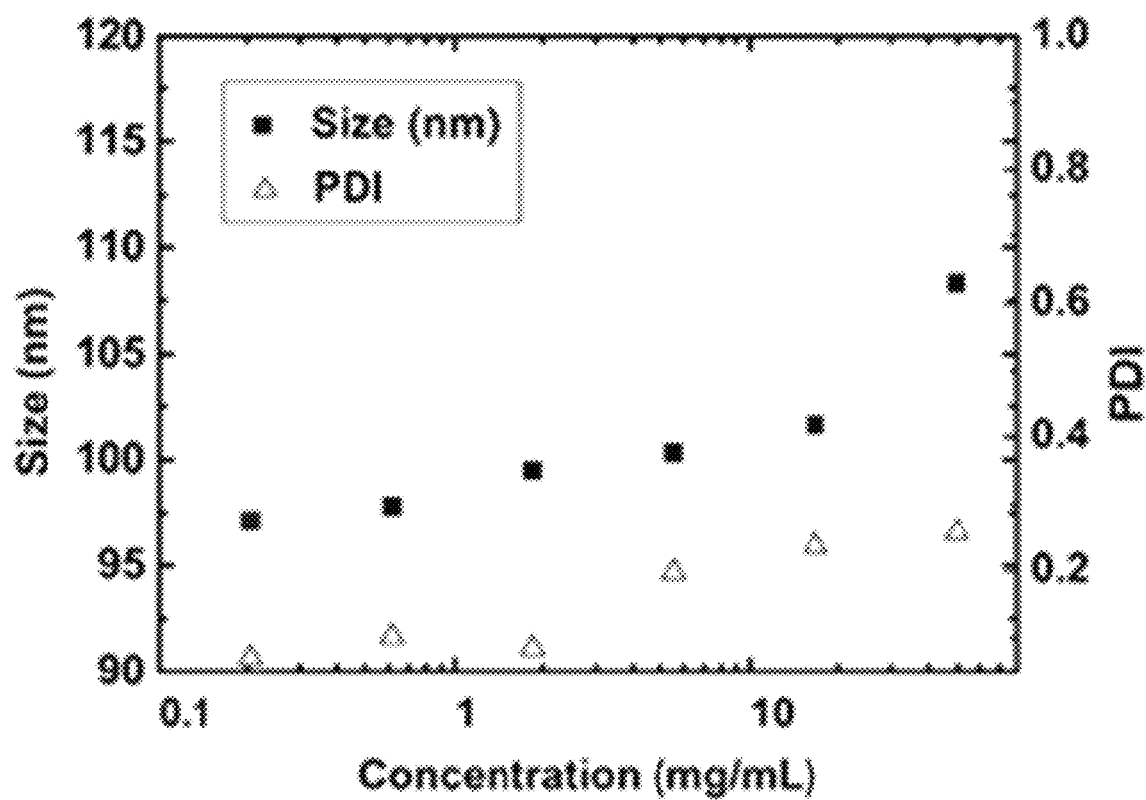
FIG. 48 shows a graph of particle size and polydispersity index (PDI) versus concentration of the silica nanoparticles, according to embodiments of the present disclosure. The particles were stable across the range of experimental concentrations. Experimental conditions: 20° C., pH 6.8.

Bare silica was tested to determine clotting values based on size and concentration (FIGS. 46-48). The same were used on P70-bound silica nanoparticles to identify thresholds that induced coagulation (FIG. 49). In certain embodiments, the short clotting times of P70-bound silica may facilitate treatments that target an internal wound. For example, particles whose concentrations are below the threshold level may be used to prevent undesired general clotting when in the general circulation. Materials may be spatially targeted to specific surfaces (e.g., wounded endothelial) to concentrate the material to above-threshold clotting behavior. Protecting the particles with PEG, which is cleaved off by factors present at the target site, may facilitate control over the location where coagulation is initiated.

Example 5

Experiments were performed on the conjugation reaction to attach polyphosphate on gold nanoparticles and the purification procedure. The purification process of gold nanoparticles involved the removal of excess, free floating polyphosphate left in the solution. A micro centrifuge (Labnet Spectrafuge 16M Microcentrifuge, Labnet International, NJ) was used to purify the samples. The centrifuging studies were done first to obtain the conditions for the removal of ~99% free floating polyP and recovering most of the gold particles (~90%) without causing aggregation. Depending on the size of the gold nanoparticles, the following conditions were used (Table 5):

TABLE 5

Size-dependent centrifugation conditions.

| Au NPs size | Rpm | G force | Time to pellet | Centrifuge |
|---|---|---|---|---|
| 10 nm | 8600 | 6000 | 100 min | 3× |
| 15 nm | 10000 | 8176 | 30 min | 2× |
| 50 nm | 8000 | 5223 | 10 min | 3× |

The pelleting time, t, was calculated using the flowing equation, (1)

$$t = \frac{k}{s} \quad (1)$$

where k is the pelleting efficiency of the rotor and S is the sedimentation coefficient. The pelleting efficiency (k) was calculated by using the equation 2 below, $$k = \frac{2.53 \times 10^{11} \left( \ln\left( \frac{r_{max}}{r_{min}} \right) \right)}{(RPM)^2} \quad (2)$$

where rmax and rmin are the maximum and minimum radii of the centrifuge respectively, and RPM is the speed in revolutions per minute. The $r_{max}$ and $r_{min}$ values were measured based on the type of the centrifuge used.

The sedimentation coefficient, S, can be calculated by using equation, $$S = \frac{2(\rho_s - \rho_l)}{9\eta} \left( \frac{d}{2} \right)^2 \quad (3)$$

where ρs and ρl are the densities of gold nanoparticles and water, respectively, η is the viscosity of water, and d is the diameter of gold nanoparticles.

After each centrifugation, the supernatant containing free-floating polyP was removed and the pellets were re-suspended with 2 mM MES at pH 9 to ensure the stability of the polyP-cystamine ligand. The pH of the samples affected the P—N bond hydrolysis. As such, the particles were resuspended with the buffer at the pH higher than 7. The resuspended samples were vortexed for 30 seconds and the centrifugation was repeated as specified in Table 6.

TABLE 6

Size-dependent centrifugation conditions.

| Au NPs size | Rpm | G force | Time to pellet | Centrifuge repeat |
|---|---|---|---|---|
| 10 nm | 8600 | 6000 | 100 min | 3× |
| 15 nm | 10000 | 8176 | 30 min | 2× |
| 50 nm | 8000 | 5223 | 10 min | 3× |

Figure 54:
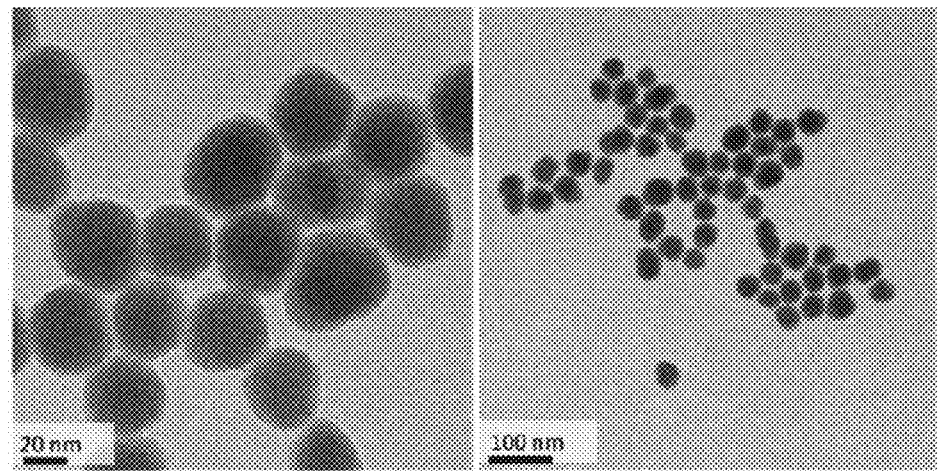
FIG. 54 shows TEM micrographs of SNP of ~55 nm size, according to embodiments of the present disclosure.

Experiments were performed on multifunctionalized silica nanoparticles (SNPs) as well as titania (TNP) and silica coated silver nanoparticles (Ag@SNP). The inorganic materials acted as the scaffold upon which the procoagulant agents attached. Nanometer-scale particles can flow through small vessels in the blood stream. Selective covalent PEGylation may be used to minimize adverse effects. FIG. 54 shows representative TEM images of the SNP synthesized with mean diameter dimensions in the range of sub-100 nm.

Figure 55:
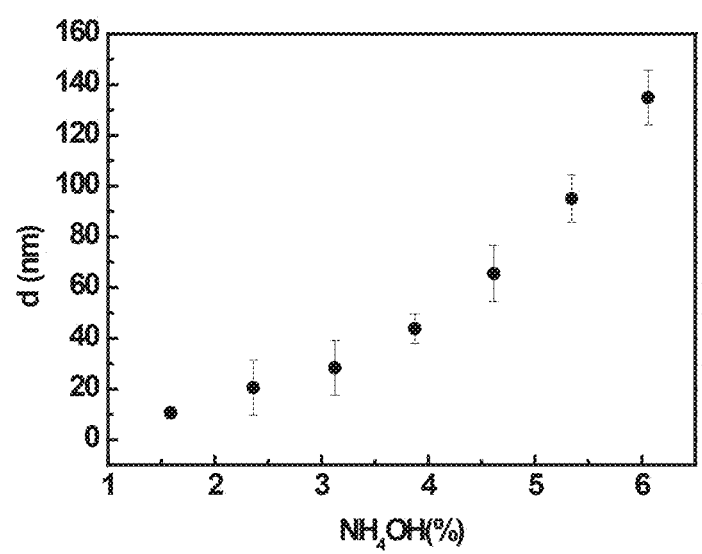
FIG. 55 shows a graph of particle size of SNP based on % $NH_4OH$ added, according to embodiments of the present disclosure.
Figure 56:
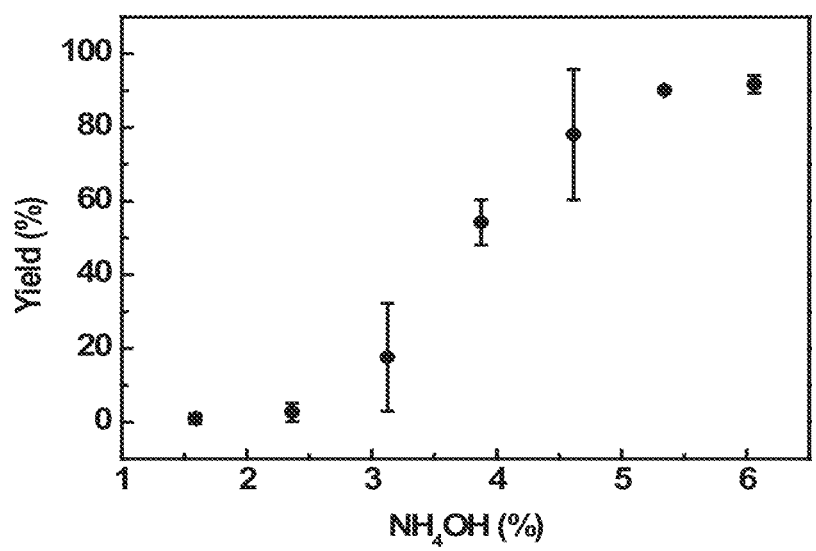
FIG. 56 shows a graph of silica yield based on % $NH_4OH$ added, according to embodiments of the present disclosure.

The effect of the silica particles' size and concentration on coagulation were measured. Particles above 10 nm in mean diameter were selective-size synthesized following a modified Stöber method and recovered using centrifugation. The different nanoparticle sizes were selectively obtained by varying the amounts of tetraethoxysilane (TEOS) and ammonia ($NH_4OH$). FIG. 55 shows the particle size as a function of the $NH_4OH$ percentage at fixed TEOS and ethanol concentrations. Ludox silica nanoparticles below 10 nm (Sigma-Aldrich) were also examined. Silica nanoparticles below 50 nm were isolated by ultrafiltration and ultracentrifugation. Yields were over 50% for syntheses using more than 4% NH4OH (FIG. 56). The smaller amount of ammonia used to make the smallest particles may inhibit catalysis of the TEOS in the hydrolysis reaction. Experiments synthesizing particles below 20 nm also exhibited a bimodal size distribution when measured using DLS. The bimodal sizes distribution may be due to the low concentration of ammonia.

Figure 57:
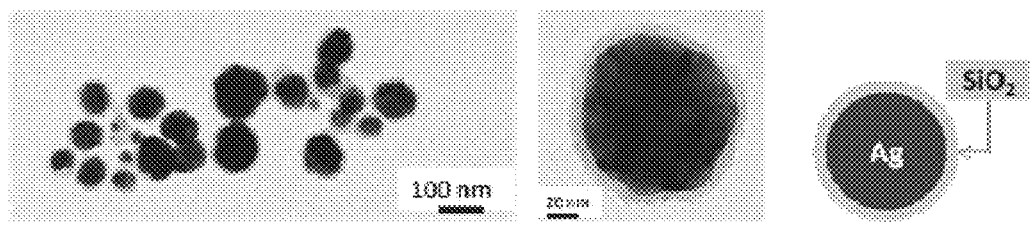
FIG. 57 shows TEM micrographs of Ag@SNP and a schematic of the particle: silver (Ag) core and silica ($SiO_2$) shell, according to embodiments of the present disclosure.

Tracking the delivery of nanoparticles to the wound using imaging may be facilitated by using silver nanoparticles coated with silica of about 10 nm thickness (Ag@SNP, FIG. 57). Initial experiments using Ag@SNP showed a delayed average R value of 13.8±1.3 min. In some instances, a thicker silica shell may be used to increase the concentration in the clotting essays. In addition to silver, magnetic nanoparticles may also be used for imaging as well as cluster control.

In addition to solid non-porous nanoparticles, high surface area (500-1000 $m^2/g$), large-pore mesoporous nanospheres (MSN) may be used to deliver procoagulant proteins such as thrombin or tissue factor, or prothrombin to wounds.

Anatase titania particles were synthesized by the sol-gel method and by varying the amount of acid catalyst added to each synthesis. The resulting titania nanoparticles were tested using X-ray diffraction and DLS to determine the form (amorphous, anatase or rutile) and size of the titania.

PolyP45-labeled gold nanoparticles (5 nm, 10 nm, 15 nm, and 50 nm) were separated from free polyP45 by centrifugation. More than 90% of the polyP-labeled gold nanoparticles were recovered and 99% of the polyP45 that was not covalently bound to the particles were removed.

High MW polyphosphate (also known as "insoluble phosphate glass") was used as the starting material for preparing polyphosphate fractions of the desired polymer lengths. The high MW polyphosphate was largely insoluble in water, as it consisted mostly of polymers that were thousands of phosphate units long. Suspending the material in an unbuffered LiCl solution and heating to 100° C. for several hours with constant stirring resulted in the majority of the polyphosphate going into solution. A time-dependent shortening of the average polymer length of the polyphosphates during heating was observed. The slightly acidic pH of the polyphosphate solutions resulted in a mild acid hydrolysis of the polymers. The speed of hydrolysis appeared to increase with time, which was the result of the gradual acidification of the solution as the polyphosphate polymers were being hydrolyzed. The gradual acidification of the polyphosphate solution therefore gradually accelerated the rate of polyphosphate hydrolysis.

Hydrolysis of the phosphoanhydride bonds in polyphosphate can also be hydrolyzed by base, and as such the gradual acidification of the solution may gradually slow the rate of hydrolysis, in contrast to acid hydrolysis whose rate increased with time. Experiments were performed by adding varying amounts of LiOH to the LiCl solutions in which polyphosphate was stirred at 100° C. A gradual, time-dependent shortening of polyphosphate chains as a function of the starting LiOH concentration was observed. As such, MW polyphosphate was suspended, with stirring, in a combination of LiCl and LiOH at 100° C. until the desired mean polymer lengths were obtained. This method was robust and reproducible, and was scalable to gram quantities of polyphosphate and higher.

The conditions for solubilizing and partially hydrolyzing polyphosphate with LiOH/LiCl were adjusted to yield the desired mean polymer lengths. In some instances, the method resulted in polyphosphate preparations with heterogeneous sizes. Differential precipitation of the polyphosphates using varying combinations of acetone and salt (e.g., NaCl, KCl and LiCl) concentrations may be used. In addition, combinations of varying concentrations of isopropanol and NaCl produced relatively narrow size fractions of polyphosphate, starting with high MW polyphosphate that had previously been solubilized and partially hydrolyzed using the LiOH/LiCl procedure outlined above. Using these conditions polyphosphate, from ~40 to ~1500 phosphate units long, in gram quantities and above was obtained.

Functionalizing the silica and anatase titania nanoparticles with polyphosphate or thrombin may enhance the procoagulant nature of the particles. Polyphosphate readily attached to the surface of inorganic nanoparticles to create a more potent agent. In addition to polyphosphate, thrombin may be attached to silica nanoparticles through the use of 3-aminopropyl triethoxysilane (APTES) and protein crosslinkers. Types of coatings that may be used include:
   SNP (FIGS. 54-56 and 58)
      3)-polyphosphate; different size (FIGS. 59-61)
      4)-APTES; low to high (FIG. 62)
         a. -APTES-polyphosphate
         b. -APTES-link-PEG (FIG. 62)
         c. -APTES-PEG-Peptide
         d. -APTES-link-Peptide
         e. -APTES-link-Peptide-PEG (FIGS. 63-64)
   TNP (FIG. 65)
      1)-polyphosphate; different size (FIG. 66)
      2)-APTES; low to high (same a to e) (FIG. 67)
   Ag@SNP (FIG. 57)
   MSN In comparison to external hemorrhage, internal hemorrhages are not directly accessible and should be accurately targeted. The particles are designed to be injected into the bloodstream and to only target and deliver at the bleeding sites. A second functionalization may be used to protect the nanoparticles from initiating clotting in healthy vessels. Nanoparticles designed for drug delivery may be coated with polyethylene glycol (PEG) to prevent unwanted activation. PEGylated nanoparticles increased the half-life of silica in the blood stream, limited cellular uptake, and limited protein adsorption to the active, yet hidden surface. At the wound, the particle may release the PEG and initiate clotting. A peptide with an IEGR (SEQ ID NO: 1) sequence that connects the particle to the PEG (FIG. 63) may be used. Activated Factor X (FXa) cleaves the peptide at the IEGR sequence, removing the PEG and leaving the activated TSP. As FXa only exists above threshold at bleeding sites, the targeting mechanism ensures that the TSP activates only where necessary.

A reverse orientation where the peptide is on the outer tip of the PEG may be used to target a damaged vascular surface, activated cell surfaces, or fibrin, for example. Thrombin and tissue factor similarly masked by PEG may be used if they can be carried in a protected form by nanoparticles to the site of interest.

Polyphosphate was attached to its nanoparticle scaffold via an APTES bridge, based on the covalent derivatization technology for polyphosphate. APTES-specific anchoring of polyphosphate may yield a higher surface density and an improved conformation. The polyphosphate coating may increase biocompatibility and specificity, conjugation versatility, and overall targetability relative to bare silica.

Experiments were performed on nanoparticles where a polyphosphate with a ~70-mer length (P70) was bound to silica in order to identify thresholds to induce coagulation. Short clotting times of P70-bound silica may facilitate targeting an internal wound. Particles whose concentrations are below the threshold level may be used in order to prevent undesired general clotting when in the general circulation. Spatially targeting the materials to the specific surfaces (e.g., wounded endothelial) may be used to concentrate the material to above-threshold clotting behavior. Protecting the particles with PEG, which is cleaved off by factors present at the target site, would add an additional level of control.

Experiments were performed to test procoagulant nanoparticles with and without adsorbed polyP, and to quantify the procoagulant activity of the nanoparticles with regard to their ability to trigger the contact pathway of blood clotting (clot initiation) as well as their activity toward accelerating the ability of FXa to clot plasma (clot propagation).

Figure 68:
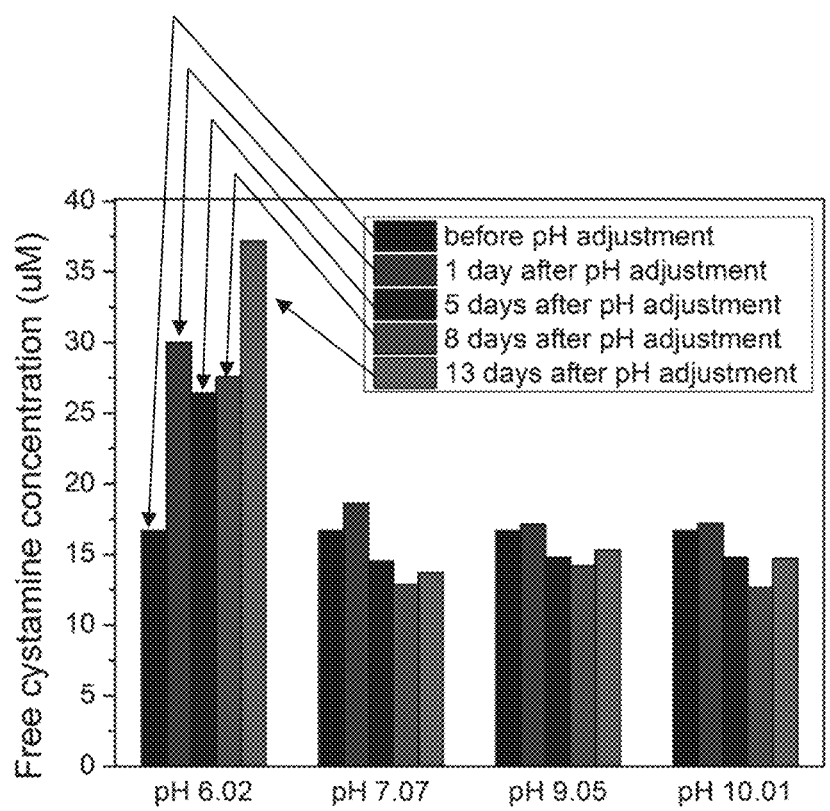
FIG. 68 shows a graph of the pH dependent hydrolysis of P—N bond of polyP-cystamine conjugate, according to embodiments of the present disclosure.

PolyP70 was used to synthesize a polyP-disulfide conjugate to covalently attach to gold nanoparticles. The binding of polyphosphate to cystamine occurred via phosphoramidite (P—N) bond formation between the terminal phosphate and the primary amine. The hydrolysis study of the P—N bond was performed to test for the stability of the polyP-cystamine ligand. The pH of the reaction was adjusted to look at the pH effect on the hydrolysis. The stability was quantified by the fluorescamine assay which detected the amount of unreacted cystamine. The increase in the amount of unreacted cystamine indicated that hydrolysis had occurred, indicating that the polyphosphate moiety was cleaved from cystamine. Based on the results as shown in FIG. 68, the P—N bond hydrolyzed in acidic conditions at pH 6.02. It was stable above pH 7.

This hydrolysis study of the polyP-cystamine ligand was used to optimize the conditions for the gold-polyP reactions. The pH of these reactions was adjusted to be higher than 7 by adjusting them with 500 mM MES buffer at pH 9. In addition, the purification process was also optimized. The nanoparticles were resuspended with 2 mM MES buffer at pH 9 to ensure that the polyP was still attached to gold nanoparticles via the cystamine linker. The above conditions were used to synthesize both polyP45- and polyP70-gold nanoparticles with various aggregation numbers. The volumes of the gold-polyP reactions were also increased to obtain higher monophosphate concentration in order to increase the sensitivity of the blood clotting measurements.

The following polyP45-Au (10 nm, 15 nm, 50 nm) nanoparticles were synthesized and tested on a coagulometer to measure clotting time using human plasma.

TABLE 7

The sample conditions for polyP45 conjugated to gold nanoparticles (10 nm, 15 nm, and 50 nm).

| Sample | PolyP Type | MonP conc. (uM) | Au particle conc. (nM) | Aggregation # | UV-vis Peak for bulk Au | UV-vis Peak after centrifuging | Volume (uL) |
| --- | --- | --- | --- | --- | --- | --- | --- |
| 10_1 | 45 | 80.00 | 104.7 | 16.98 | 519 | 523 | 240 |
| 10_2 | 45 | 80.00 | 90.34 | 19.68 | 519 | 524 | 320 |
| 15_1 | 45 | 80.00 | 29.29 | 60.70 | 521 | 523 | 290 |
| 15_2 | 45 | 80.00 | 37.33 | 47.62 | 521 | 523 | 340 |
| 50_1 | 45 | 80.00 | 3.74 | 475.34 | 533 | 533 | 390 |
| 50_2 | 45 | 80.00 | 2.03 | 875.75 | 533 | 533 | 390 |

The following polyP70-Au nanoparticles were synthesized (FIG. 102) and were tested for procoagulant activities.

Figure 69:
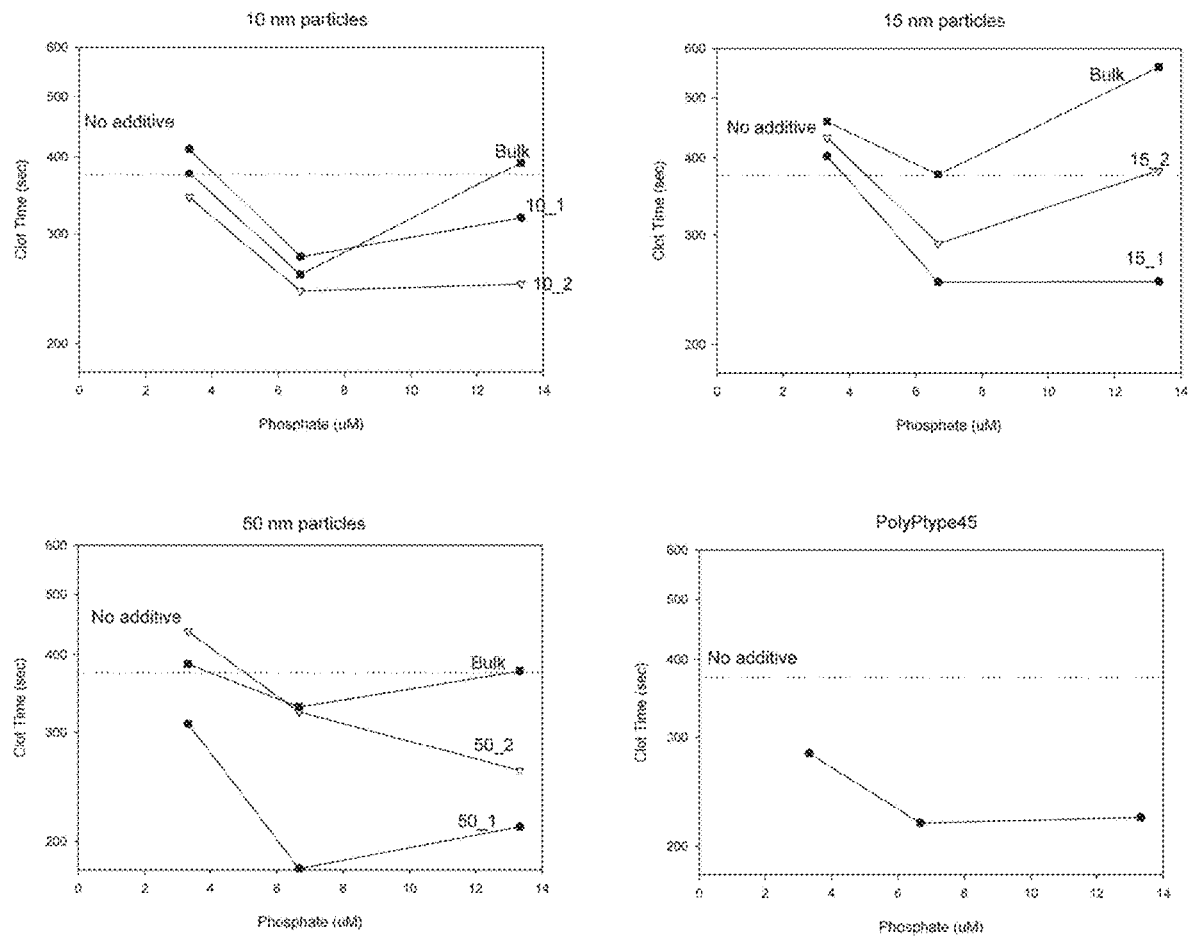
FIG. 69 shows graphs of the clotting data for the gold particles presented in FIG. 102 when assayed for the ability to activate the contact pathway, according to embodiments of the present disclosure.

Results (FIG. 69) using the particles in FIG. 102 showed that 50 nm gold particles with the highest aggregation number had the highest procoagulant activities (i.e., shortest clot times when tested at ~6.5 uM phosphate). These results demonstrated that the procoagulant activity of the gold particles was modulated by the number of polyphosphate molecules/particle.

Attaching polyphosphate P70 to the surface of solid silica nanoparticles through APTES may facilitate specific functionalization of threshold-switchable particles, TSP, which induce clotting solely at the desired wound site.

In addition to P70, linger chain polyphosphates (~700-mer, P700) may be used. Polyphosphate with a size range above 500-mers initiated the contact or intrinsic pathway of blood clotting. The P700 can be attached to the scaffolds using the same methods described above.

Clotting experiments described above compared the silica particles at either a fixed concentration of 0.68 mg/mL (25 mg/mL stock solution) or at a fixed size of 55 nm to determine high activity range boundaries. Each particle formed an initial clot (R) between 3 and 5 min. The threshold for minimum R value occurred at a particle size of ~30 nm.

Figure 58:
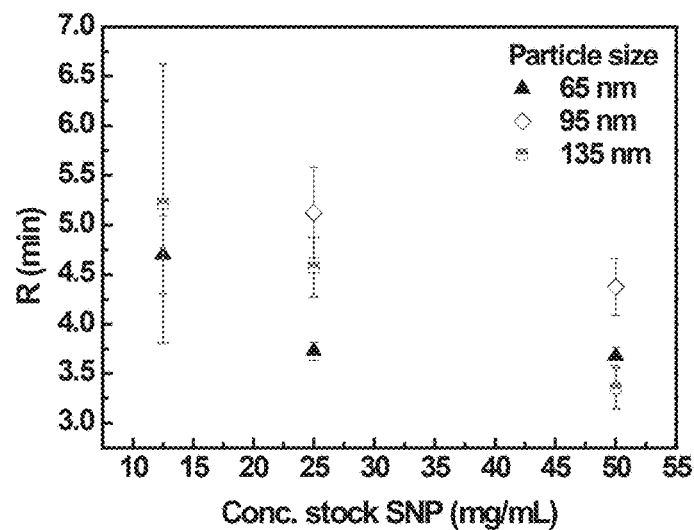
FIG. 58 shows a graph of clotting time (R, min) versus stock concentration (mg/mL) of the silica nanoparticles of different sizes, according to embodiments of the present disclosure. 50 mg/mL corresponds to 1.35 mg/mL in TEG cup. Experimental conditions: 37° C., 11 mM $Ca^{2+}$.

Using 55-nm silica particles, ~0.6 mg/ml (30 mg/mL stock) bare silica was identified as the threshold required to minimize R. At this concentration, the R value averaged 3 min (compared to 12-16 minutes without silica). The R value remained near 3 min for double the silica (1.35 mg/ml) and then rose slightly to 3.5 min at 2.70 mg/ml. The increase in R at high concentrations may have occurred as a result of particle aggregation or dilution of plasma factors over the particle's surface area. Regardless of concentration, DLS tests confirmed that the particles maintain stability and size. At low particle concentrations, the R value was high. As the particle concentration increased, R decreased until the threshold condition was met. At this point, R remained low and stable until the particle concentration became high enough to inhibit clotting. FIG. 58 shows a narrow range of concentrations near the optimum value for different particle size SNP. In addition to the clotting time (R) other parameters were also evaluated, such as rate of clot formation, and clot size, since the agents attached on the particle might not affect the initial clot formation time, but could accelerate the clotting when initiated or could result in the formation of a bigger clot.

Figure 59A:
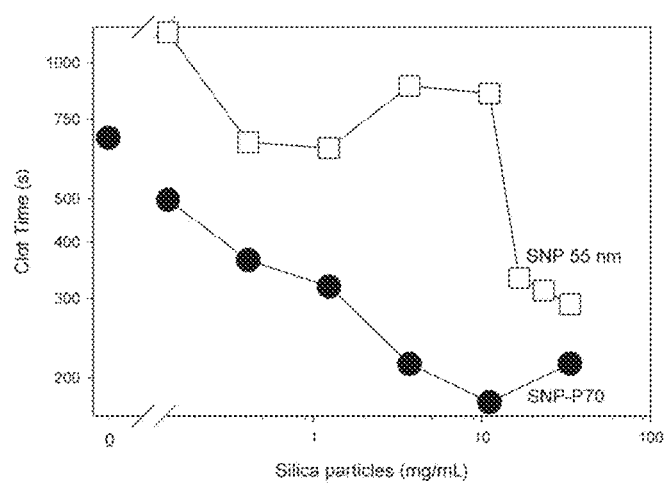
FIG. 59A shows a graph of clotting time of SNP with and without polyphosphate (P70) as a function of concentration.
Figure 59B:
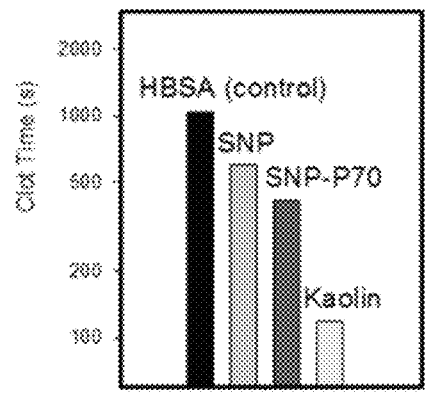
FIG. 59B shows a graph of clotting time of different samples, including SNP, SNP—P70 and Kaolin, according to embodiments of the present disclosure.
Figure 60:
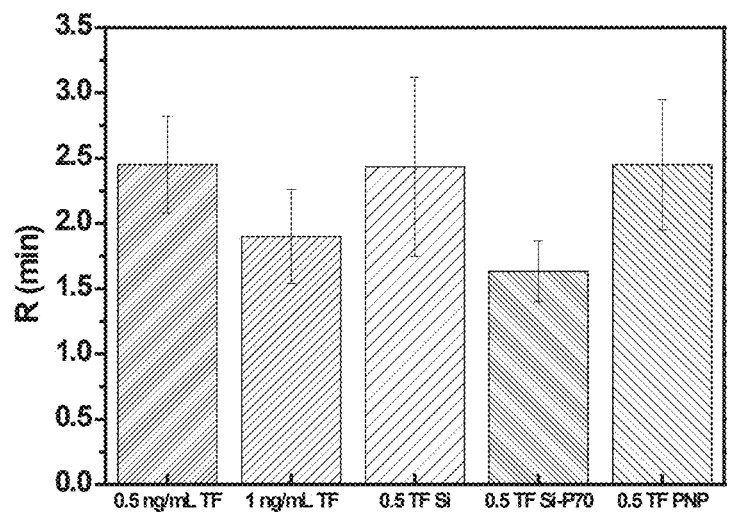
FIG. 60 shows a graph of clotting time (R) for various conditions using FXII deficient plasma, according to embodiments of the present disclosure. SiO$_2$—P70 had the smallest and most consistent R value. Last bar was a control using pooled normal plasma.

The polyphosphate used in the assays was a ~70-mer length (P70) chosen for its similarity to the size of polyphosphate secreted by human platelets during clotting, and which activate FV. P70 directly adsorbed to silica was found to slightly increase the particle size (by several nm). Samples of bare and P70-bound 55-nm silica nanoparticles were tested for polyphosphate quantification and coagulation. The results are shown in FIGS. 59A and 59B, which show that P70-bound SNPs significantly decreased clotting time when compared to bare SNP.

Figure 65:
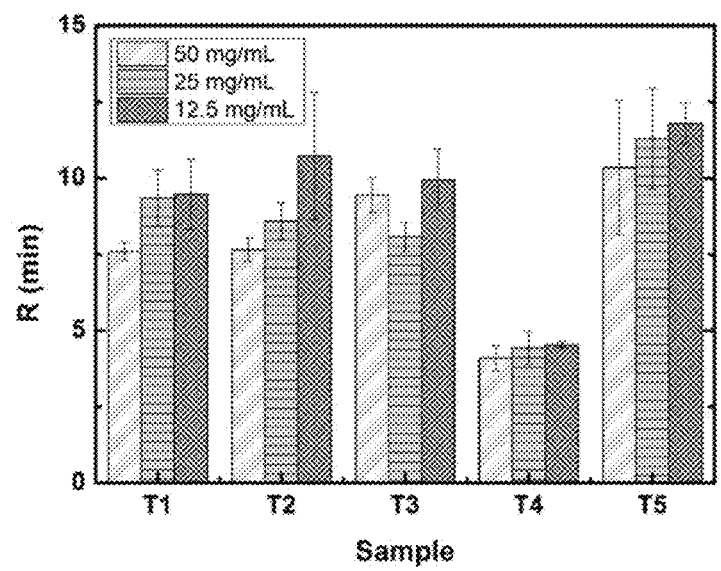
FIG. 65 shows a graph of clotting time (R) of various anatase titania synthesis at different stock concentrations, according to embodiments of the present disclosure. Experimental conditions: 37° C., 11 mM Ca$^{2+}$.
Figure 66:
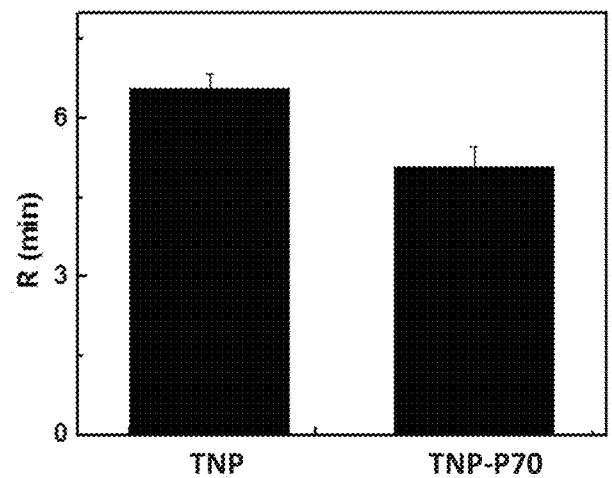
FIG. 66 shows a graph of clotting times of TNP with and without polyphosphate (P70) at a concentration of 100 mg/mL (stock), according to embodiments of the present disclosure.

The clotting properties of the anatase titania were also tested. The clotting times of the four acid-catalyzed syntheses shared similar clotting times. The titania formed at neutral pH exhibited a lower clotting time (T4 in FIG. 65). Concentration-dependent experiments also confirmed that when diluted, the clotting activity diminished. When functionalized with P70, the T4 samples further reduced clotting time (FIG. 66).

Figure 61:
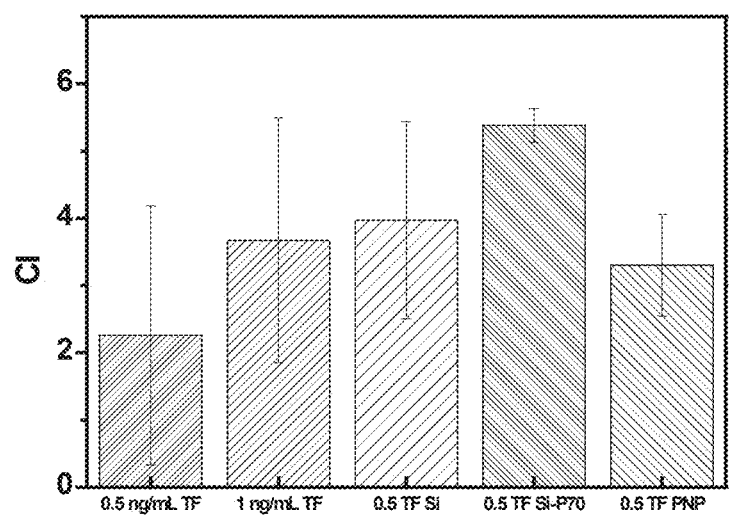
FIG. 61 shows a graph of coagulation Index (CI) for various conditions using FXII deficient plasma, according to embodiments of the present disclosure. SiO$_2$—P70 had the highest and most consistent CI value. Last bar was a control using pooled normal plasma.

Clotting tests were performed using FXII deficient plasma (FIG. 60) to study the mechanism by which P70-bound nanoparticles induce clotting. As they activate clotting through FXII activation and the intrinsic pathway, the bare nanoparticles do not induce clotting in the FXII deficient plasma. With the intrinsic pathway blocked, coagulation only occurred through the addition of tissue factor (TF) and the extrinsic pathway. Since P70 accelerated coagulation through FVa, a combination of TF and P70-bound silica improved clotting via the ability of polyphosphate to accelerate the propagation phase of blood clotting. Various mixtures of TF and nanoparticles were compared. The two lowest clotting times occurred as a result of either 1 ng/mL TF or 0.5 ng/mL TF mixed with 0.676 mg/mL P70-bound silica. Though the two conditions shared a similar clotting time, the P70-bound silica rapidly accelerated clot growth as illustrated by the larger coagulation index score (FIG. 61). The P70-bound silica also gave reproducible conditions, which may facilitate a reduction in adverse side-effects. The tissue factor formed a small clot rapidly upon addition to plasma, but the clot grew at a slow pace. These tests showed that even under adverse conditions the P70 bound particles quickly increased clotting through mediating FXa and thrombin. As such, polyphosphate can accelerate thrombin production at an in progress bleed and thus limit blood loss.

Figure 62:
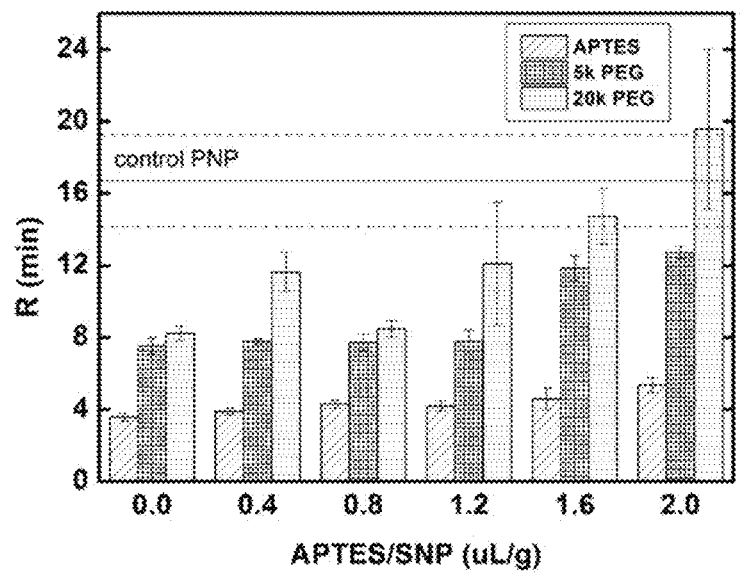
FIG. 62 shows a graph of clotting time (R) vs. APTES/SNP (μL/g) for APTES, 5k PEG and 20k PEG SNPs, according to embodiments of the present disclosure.
Figure 63:
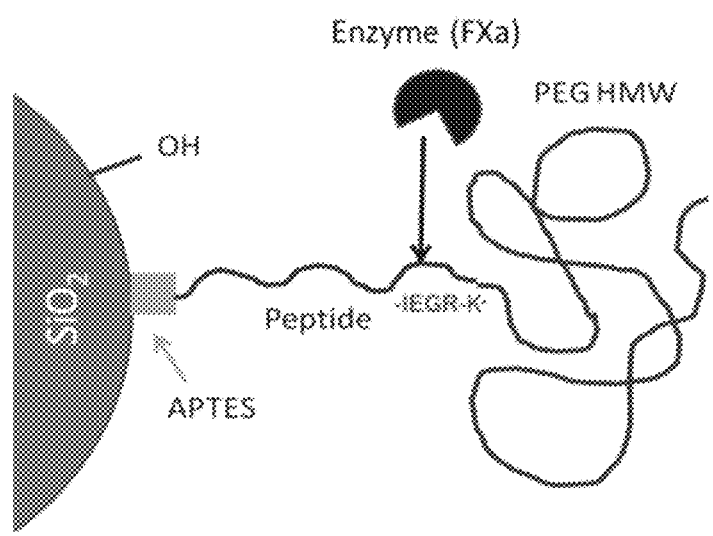
FIG. 63 shows a schematic of FXa (found in the wound site) that recognizes peptide sequence (IEGR) (SEQ ID NO: 1) and cleaves PEG off the TSP to selectively activate coagulation, according to embodiments of the present disclosure.
Figure 64:
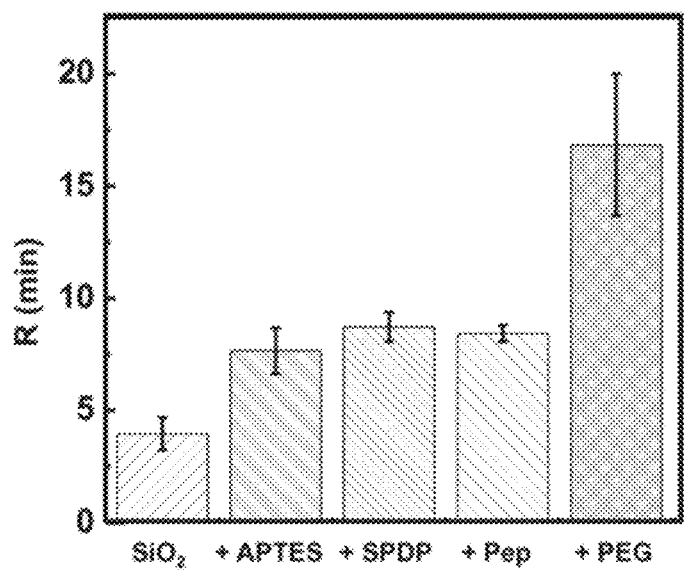
FIG. 64 shows a graph of clotting times of functionalized silica particles, according to embodiments of the present disclosure. (Pep: peptide, PEG used is 2k).
Figure 67:
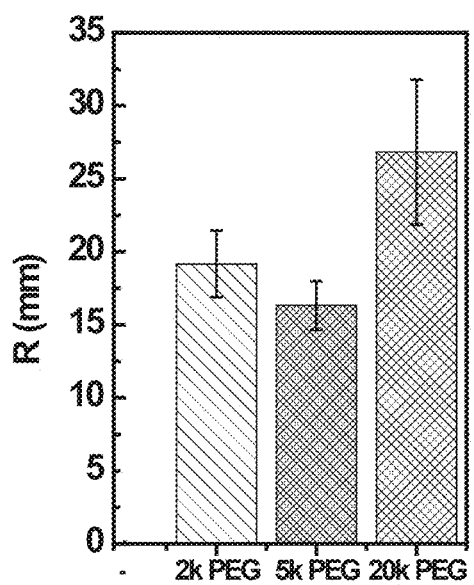
FIG. 67 shows a graph of clotting times for PEGylated TNP, according to embodiments of the present disclosure.

When bound to the nanoparticle surface, APTES and other cross-linkers reduced the active surface for coagulation (FIGS. 62 and 64). Experiments were performed to vary the ratio of APTES to silica in order to optimize a TSP that would retain a dual nature—inert in healthy blood vessels and procoagulant when activated. When functionalized solely with APTES, the TSP retained its procoagulant nature. When PEG attached to the TSP via the APTES bridge, the TSP was protected. Using 5k or 20k sized PEG decreased clotting times so that they were comparable to that obtained using recalcified plasma. Replacing silica with titania as the scaffold resulted in similar clotting times (FIG. 67).

A TSP was prepared that remained unactivated in healthy blood vessels, while being activated at a wound site in order to obtain an effective internal bleeding therapeutic agent that is only active at the bleeding site while remaining unactivated in healthy blood vessels. FIG. 64 shows that, apart from the APTES, the nanoparticles remained active even when the SPDP (SEQ ID NO: 10) linker and the peptide were attached, since the clotting time remained low. When the PEG was attached the clotting time was comparable to that of recalcified plasma without the particles, thus establishing that the PEGylated nanoparticles with PEG molecular weight greater than 5k were non-coagulant. Enzymes may be used to cleave the peptide and release the PEG. For example, an IEGR sequence in the peptide and FXa as the enzyme may be used. The proteolytic activity of the enzyme can be quantified by fluorescence and its reaction rate (enzyme kinetics) compared with TCEP, a potent versatile reducing agent.

Figure 70:
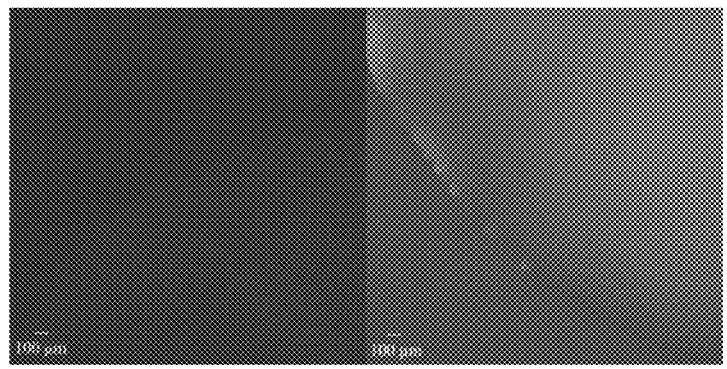
FIG. 70 shows images of: (Left) Blue coumarin dye experiment at time 0 min; and (Right) Blue coumarin experiment at time 20 min, according to embodiments of the present disclosure.

In addition to TEG, the coagulation threshold response was tested using a thrombin-specific blue coumarin dye. A small concentration of dye was added to the recalcified plasma. As clotting progressed and thrombin activated, the thrombin cleaved the coumarin dye causing the solution to fluoresce. For instance, the thrombin burst signified by the fluorescence may indicate clot formation. A fluorescence microscope captured the qualitative change as shown in FIG. 70. A microscope and/or a plate reader was used to monitor clotting through the dye's fluorescence. The plate reader can measure up to 96 samples at the same time. This allowed the study of several TSPs along with a standard thrombin concentration concurrently to determine the most active TSP. Particles clustered together as well as those that are finely dispersed in plasma can be studied.

Example 6

Threshold-Switchable Particles (TSP)

Experiments were performed to develop targeted delivery of nanoparticles functionalized with controlled amounts of polyP. These tunable particles are able to selectively target sites of injury in response to appropriate stimuli such as a drop in temperature without the induction of clotting at other locations in the body.

Figure 71:
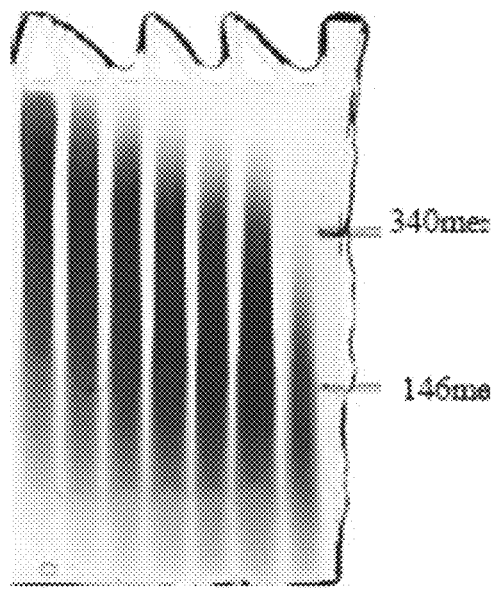
FIG. 71 shows an image of polyacrylamide gel electrophoresis (PAGE) of material acquired during time course of hydrolysis with unbuffered LiCl, according to embodiments of the present disclosure.

High MW polyP preparation (also known as "insoluble sodium phosphate glass") was used as the starting material for preparing polyP fractions of the desired polymer lengths. High MW polyP was largely insoluble in water, as it consisted mostly of polymers that were thousands of phosphate units long. High MW polyP was suspended in non-buffered 100° C. 0.25 M LiCl solution with constant stirring, and resulted in the majority of the polyP solubilizing and going into solution. A time-dependent shortening of the average polymer length of the polyPs during heating was observed (FIG. 71). The slightly acidic pH of the polyP solutions resulted in a mild acid hydrolysis of the polymers. The speed of hydrolysis appeared to increase with time, which was the result of the gradual acidification of the solution as the polyP polymers were being hydrolyzed. The gradual acidification of the polyP solution gradually accelerated the rate of polyP hydrolysis.

Figure 72:
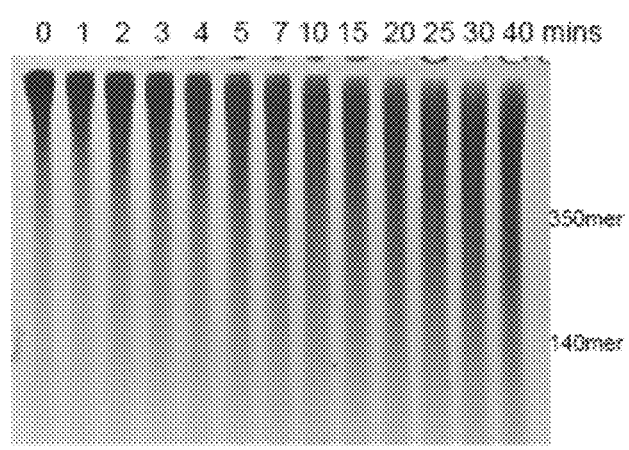
FIG. 72 shows an image of PAGE material acquired during time course of hydrolysis with alkaline LiCl, according to embodiments of the present disclosure.

Hydrolysis of the phosphoanhydride bonds in polyP was also catalyzed under basic conditions, and the gradual acidification of the solution during polyP hydrolysis gradually slowed the rate of hydrolysis, in contrast to acid hydrolysis whose rate increased with time. Varying amounts of LiOH were added to the LiCl solutions in which polyP was stirred at 100° C. A gradual, time-dependent shortening of polyP chains as a function of the starting LiOH concentration was observed, which was accompanied by the "insoluble" polyP polymers becoming water-soluble (FIG. 72). High MW polyP was suspended, with stirring, in a combination of LiCl and LiOH at 100° C. until the desired mean polymer lengths were obtained and essentially 100% of the material was solubilized. This method was robust and reproducible, and scalable to gram quantities of polyP and higher.

Figure 73:
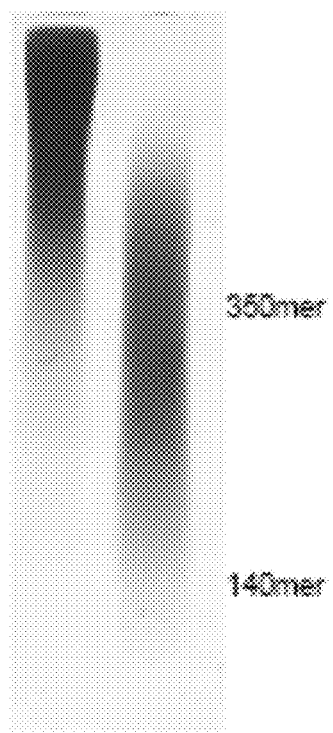
FIG. 73 shows an image of PAGE of size fractionated high yield polyP, according to embodiments of the present disclosure.

The conditions for solubilizing and partially hydrolyzing polyP with LiOH/LiCl were adjusted to yield the desired mean polymer lengths. In some instances, the method resulted in polyP preparations of heterogeneous sizes. Experiments were performed to further size-fractionate polyP after base hydrolysis. Differential precipitation of polyP using varying combinations of acetone and salt concentrations (e.g., NaCl, KCl and LiCl) were tested. In addition, varying concentrations of isopropanol and NaCl allowed the production of relatively narrow size fractions of polyP, starting with high MW polyP that had previously been solubilized and partially hydrolyzed using the LiOH/LiCl procedure outlined above (see FIG. 73 for an example). The above conditions were used to obtain size ranges of polyP from ~40 to ~1500 phosphate units long, in gram quantities and above.

Citrate Gold Nanoparticle Synthesis

Figure 74A:
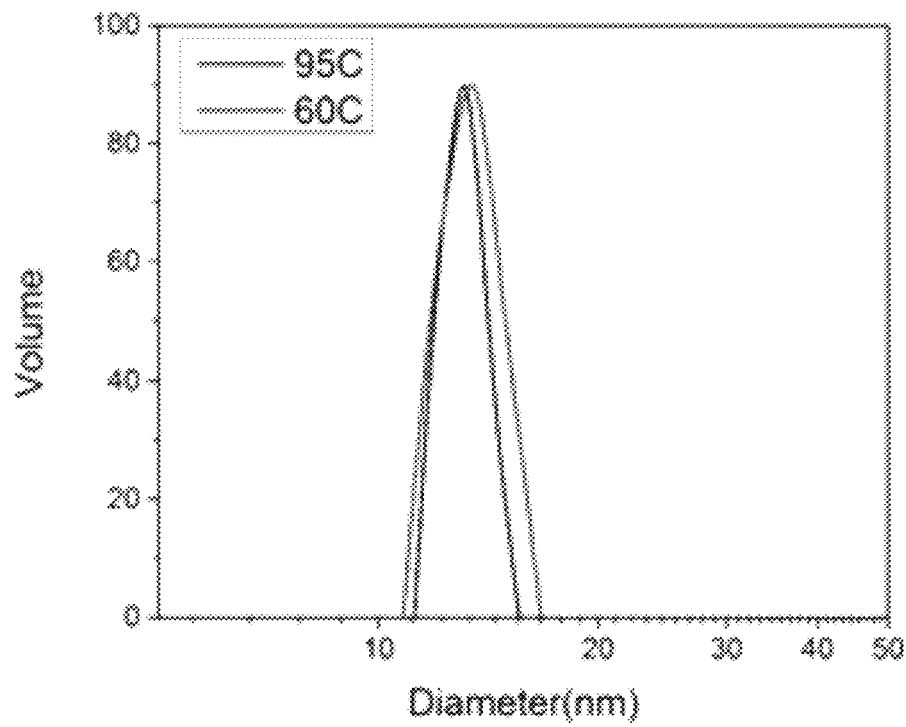
FIGS. 74A-74C show graphs of size distribution of gold nanoparticles measured by DLS, according to embodiments of the present disclosure. Molar ratio of citrate to gold was (FIG. 74A) 4:1, (FIG. 74B) 3:1 and (FIG. 74C) 1:1.
Figure 74B:
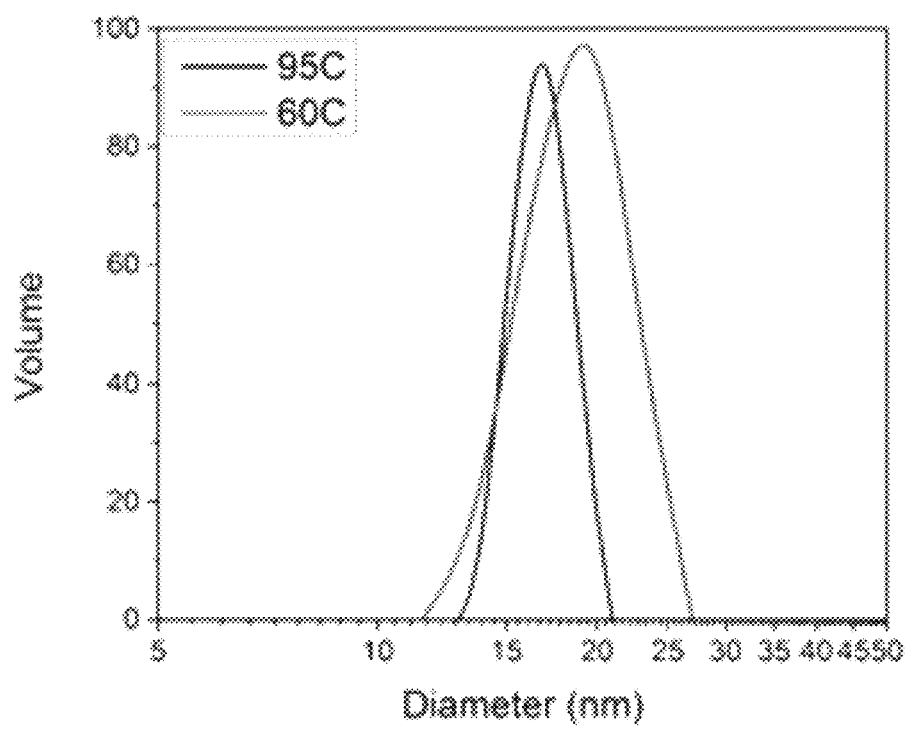
Figure 74C:
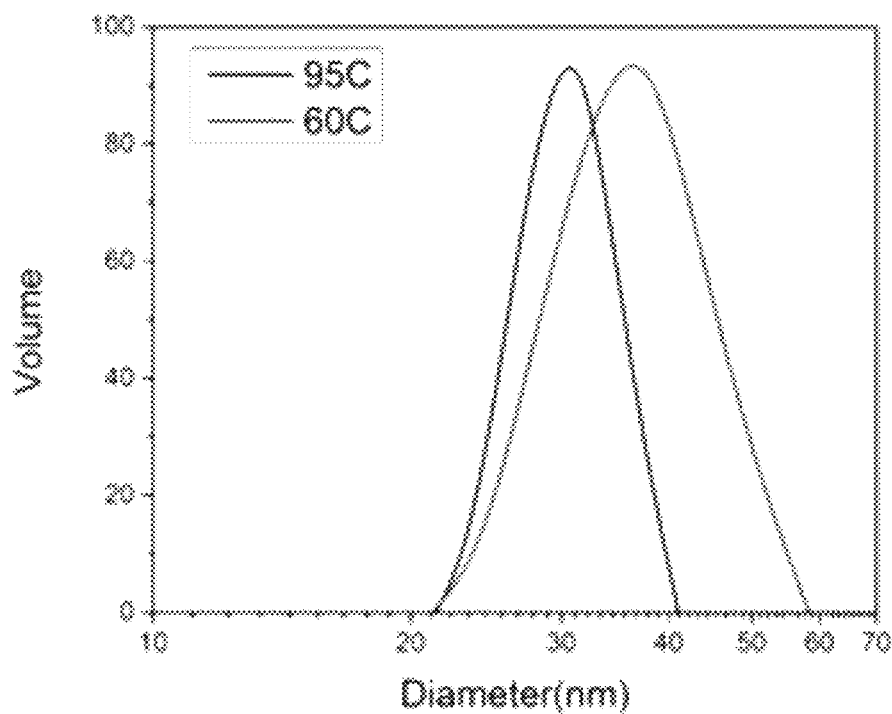

Gold nanoparticles with an average diameter of 10 nm, 15 nm, and 50 nm were synthesized by using the Turkevich Method. The average size and size distribution of the gold nanoparticles were confirmed by dynamic light scattering (DLS) and UV-vis absorbance (Table 9 and FIGS. 74A-C).

TABLE 9

Comparison of 10 nm, 15 nm, 50 nm gold nanoparticles and commercial samples with their UV-vis peak, DLS-measured particles size and polydispersity

|  | Mole ratio (Cg:Cc) | Gold Concentration | Reaction Temperature | UV Peak | Size | Polydispersity |
|---|---|---|---|---|---|---|
| Reaction A | 1:4 | 0.4 mM | 95° C. | 520 nm | 13.6 nm | 0.175 |
|  |  |  | 60° C. | 522 nm | 14.7 nm | 0.25 |
| Reaction B | 1:3 | 0.4 mM | 95° C. | 522 nm | 17.2 nm | 0.178 |
|  |  |  | 60° C. | 522 nm | 18.3 nm | 0.227 |
| Reaction C | 1:1 | 0.4 mM | 95° C. | 533 nm | 35.7 nm | 0.196 |
|  |  |  | 60° C. | 534 nm | 37.9 nm | 0.256 |

TABLE 9-continued

Comparison of 10 nm, 15 nm, 50 nm gold nanoparticles and commercial samples with their UV-vis peak, DLS-measured particles size and polydispersity

|  | Mole ratio (Cg:Cc) | Gold Concentration | Reaction Temperature | UV Peak | Size | Polydispersity |
|---|---|---|---|---|---|---|
| Commercial_10 |  | 0.29 mM |  | 519 nm | 11.3 nm | 0.24 |
| Commercial_15 |  | 0.24 mM |  | 521 nm | 15.6 nm | 0.19 |
| Commercial_50 |  | 2.89 mM |  | 532 nm | 42.1 nm | 0.11 |

PolyP-Gold Nanoparticle Conjugates

Figure 75:
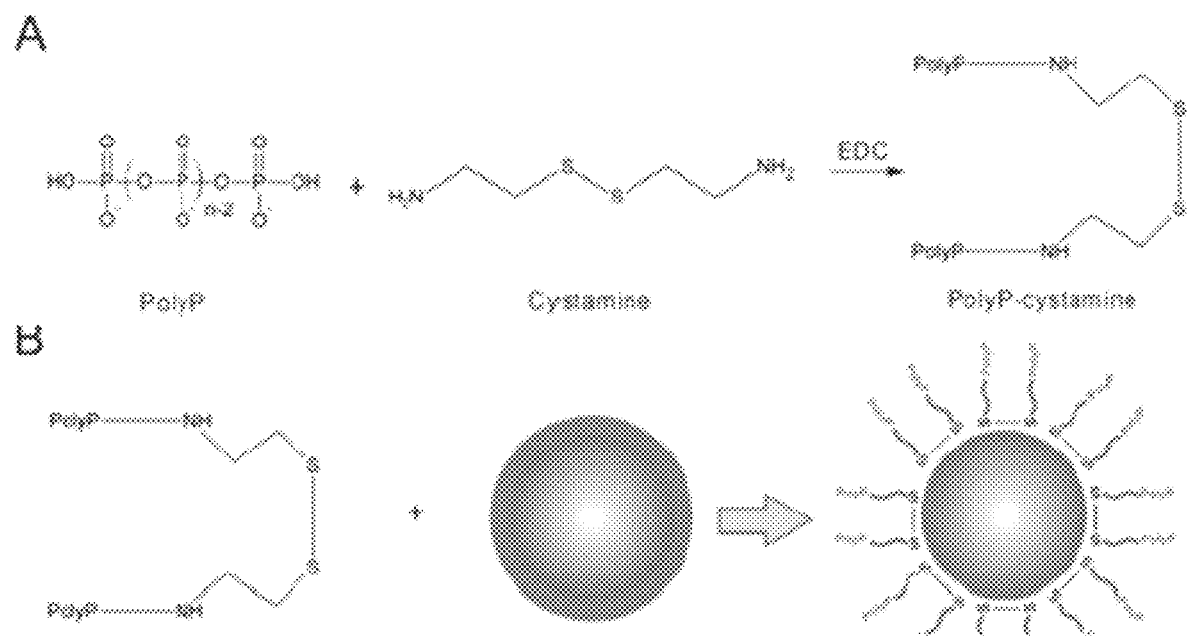
FIG. 75, panel A, and FIG. 75, panel B, show schematics of the process of synthesizing gold nanoparticles conjugated with polyP, according to embodiments of the present disclosure.

Attachment of polyP to gold nanoparticles was achieved by two-stage reactions. (1) PolyP was allowed to react with cystamine; (2) PolyP-cystamine conjugates were then reacted with gold particles via displacement of the citrate groups (FIGS. 75, panel A, and FIG. 75, panel B). The primary amine-containing compounds like polyethylenimine, amine-PEG$_2$-biotyn, and spermidine were used to covalently attach primary amine groups with the terminal phosphates of polyP via EDAC-meditated reaction. This method was used for the coupling of polyP with cystamine—a disulfide molecule containing two primary amine groups. The disulfide moiety in cystamine then allowed for the attachment to gold. Various conditions (including temperature, reaction time, pH, and buffer solutions) were tested in order to optimize the reaction efficiency and yield.

The effects of polyP-gold nanoparticles (with different sizes and polyP aggregation numbers) on blood clotting kinetics were tested. The following control groups were selected to compare with polyP-gold nanoparticle conjugates: (1) free polyP with the same molecular weight at the same concentrations; (2) citrate gold nanoparticles without polyP; and (3) PEGylated gold nanoparticles. Various aggregation numbers of polyP on gold nanoparticles were achieved by adding PEG thiol to compete with polyP-cystamine for ligand replacement.

PolyP-Cystamine Conjugation Reaction

Various conditions (including temperature, reaction time, pH, and buffer solutions) were tested for the coupling reaction of polyP with cystamine. Polyp was allowed to react with cystamine at room temperature for 48 to 72 hrs. The pH for the reaction was about 8. A fluorescamine assay was used to test the amount of the unreacted primary amines on cystamine, which indicated the conjugation efficiency. The yield of the reaction was approximately 90% as seen in (Table 10).

TABLE 10

Conjugation efficiency of polyP and cystamine at various pH conditions.

| Buffer | pH of reaction | Efficiency (24 h) | Efficiency (48 h) | Efficiency (72 h) |
|---|---|---|---|---|
| MOPS (100 nM) | 7.1 | 61.5% | 65.0% | 71.1% |
| MOPS (100 mM) | 7.6 | 72.7% | 74.3% | 78.7% |
| MOPS (100 mM) | 8.1 | 79.6% | 87.3% | 88.1% |
| MOPS (100 mM) | 8.5 | 83.5% | 87.3% | 88.6% |
| MES (100 mM) | 7.8 | 81.4% | 89.5% | — |

The hydrolysis study of the P—N bond was carried out to test the stability of the polyPcystamine ligand. After 72 hours of reaction, the fluorescamine assay was performed to detect the concentration of the unreacted cystamine. An increase of free cystamine concentration after the pH adjustment of reactions indicated the hydrolysis of the P—N bond. The samples were tested for two weeks and quantified by the fluorescamine assay. The P—N bond hydrolyzed in acidic conditions at pH 6.02. It was stable above pH 7 as seen in Table 11 below.

TABLE 11

Free cystamine concentration (μM) before and after pH adjustment

| | Primary amine concentration (μM) | | | | |
|---|---|---|---|---|---|
| pH | Before pH adjustment | After 1 day | After 5 days | After 8 days | After 13 days |
| 6.02 | 16.4 | 30.0 | 26.4 | 27.6 | 37.18 |
| 7.07 | 16.4 | 18.6 | 14.5 | 12.9 | 13.72 |
| 9.05 | 16.4 | 17.1 | 14.8 | 14.2 | 15.31 |
| 10.01 | 16.4 | 17.2 | 14.8 | 12.7 | 14.73 |

Reaction of polyP-Cystamine with Gold Nanoparticles

The polyP-cystamine conjugate was allowed to react with gold nanoparticles of various sizes (10 nm, 15 nm, 50 nm) by displacing the citrate group. After 24 hrs of reaction the salt addition was initiated to increase the coverage of the surface of the gold nanoparticle with polyP. The slow increase in the salt concentration in the reaction over a period of four days (0.1M NaCl final concentration) allowed for the already attached polyP to extend, creating more space for the unreacted ligands to access the gold surface and thus resulting in an increase in the aggregation number.

The purification process of gold nanoparticles involved the removal of excess, free floating polyP left in the solution. Centrifugation was used to remove ~99% free floating polyP and recover most of the gold particles (~90%) without causing aggregation. Depending on the size of the gold nanoparticles, the following conditions were found (Table 12).

TABLE 12

Size-dependent centrifugation conditions

| Au NPs size | RPM | G force | Time to pellet | Centrifuge repeat |
|---|---|---|---|---|
| 10 nm | 10000 | 8176 | 60 min | 3× |
| 15 nm | 10000 | 8176 | 30 min | 2× |
| 50 nm | 8000 | 5223 | 10 min | 3× |

The pelleting time, t, was calculated using the flowing Equation 1:

$$t = \frac{k}{s} \tag{1}$$

where k is the pelleting efficiency of the rotor and S is the sedimentation coefficient. The pelleting efficiency (k) was calculated by using Equation 2 below:

$$k = \frac{2.53 \times 10^{11} \left( \ln\left(\frac{r_{max}}{r_{min}}\right) \right)}{(RPM)^2} \quad (2)$$

Figure 76:
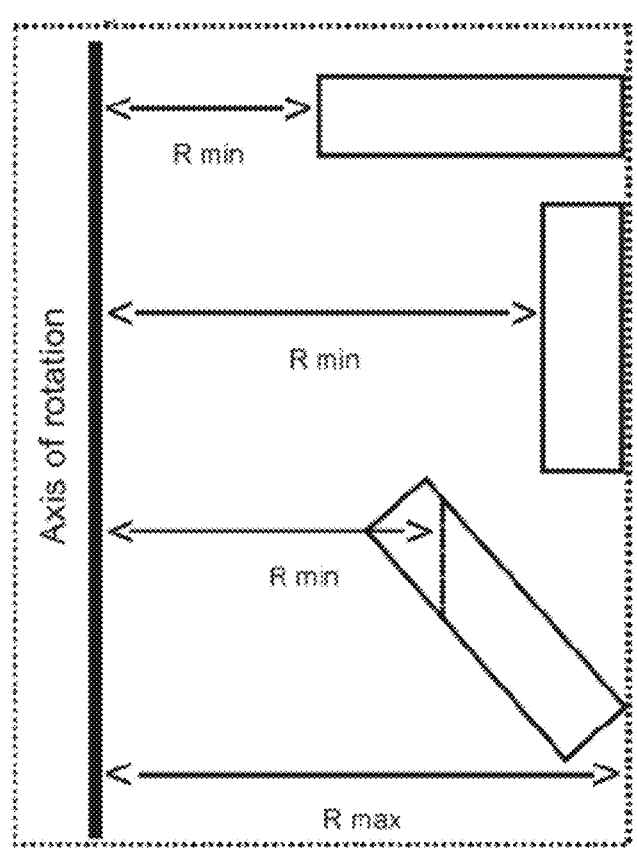
FIG. 76 shows a schematic of the determination of the minimum and maximum radius based on the geometry of a centrifuge, according to embodiments of the present disclosure.

$r_{max}$ and $r_{min}$ are the maximum and minimum radii of the centrifuge respectively, and RPM is the speed in revolutions per minute. The $r_{max}$ and $r_{min}$ values can be measured as shown in FIG. 76 based on the type of centrifuge used.

The sedimentation coefficient, S, can be calculated by using Equation 3:

$$S = \frac{2(\rho_s - \rho_l)}{9\eta}\left(\frac{d}{2}\right)^2 \quad (3)$$

where $\rho_s$ and $\rho_l$ are the densities of gold nanoparticles and water, respectively, $\eta$ is the viscosity of water, and d is the diameter of gold nanoparticles.

After each centrifugation, the supernatant was removed and the pellets were re-suspended in a buffer of pH 7.4 to ensure the stability of the polyP-cystamine ligand. As the hydrolysis study showed, the pH of the samples affected P—N bond hydrolysis. Therefore, the particles were resuspended with a buffer at a pH higher than 7.

Dynamic light scattering (DLS) and UV-vis spectroscopy were used to characterize the size and size distribution of the particles. After purification/separation using centrifugation, concentrations of polyP were measured using malachite green assay and concentrations of gold nanoparticles were obtained by UV-vis. Then aggregation numbers of polyP on the surface of gold nanoparticles were calculated based on the above measurements. The following polyP-gold nanoparticles (Tables 13-15) were synthesized and characterized.

TABLE 13

Synthesized polyP45-gold nanoparticles

| Sample | PolyP size (# of repeating units) | MonoP Conc. (μM) | Gold Particle Conc. (nM) | Aggregation # | UV-vis peak for bulk gold | Peak after centrifuging |
|---|---|---|---|---|---|---|
| P45_10 nm_1 | 45 | 80.00 | 104.7 | 16.98 | 519 | 523 |
| P45_10 nm_2 | 45 | 80.00 | 90.34 | 19.68 | 519 | 524 |
| P45_15 nm_1 | 45 | 80.00 | 29.29 | 60.70 | 521 | 523 |
| P45_15 nm_2 | 45 | 80.00 | 37.33 | 47.62 | 521 | 523 |
| P45_50 nm_1 | 45 | 80.00 | 3.74 | 475.34 | 533 | 533 |
| P45_50 nm_2 | 45 | 80.00 | 2.03 | 875.75 | 533 | 533 |

TABLE 14

Synthesized polyP70-gold nanoparticles

| Sample | PolyP size | MonoP Conc. (μM) | Gold Particle Conc. (nM) | Aggregation # | UV-vis peak for bulk gold | Peak after centrifuging |
|---|---|---|---|---|---|---|
| P70_10 nm_1 | 70 | 75.00 | 31.98 | 33.50 | 519 | 524 |
| P70_10 nm_2 | 70 | 75.00 | 153.50 | 6.98 | 519 | 528 |
| P70_15 nm_1 | 70 | 75.00 | 16.14 | 66.38 | 521 | 522 |
| P70_15 nm_2 | 70 | 75.00 | 32.05 | 33.43 | 521 | 522 |
| P70_50 nm_1 | 70 | 75.00 | 2.068 | 518.09 | 532 | 533 |
| P70_50 nm_2 | 70 | 75.00 | 2.010 | 533.05 | 532 | 533 |

TABLE 15

Synthesized polyP-PEG (3:1)-gold nanoparticles

| Sample | PolyP | MonoP Conc. (μM) | Gold Particle Conc. (nM) | Aggregation # | UV-vis peak for bulk gold | Peak after centrifuging |
|---|---|---|---|---|---|---|
| P70_Peg_10 nm_1 | 70 | 75.00 | 76.00 | 14.1 | 519 | 525 |
| P70_Peg_15 nm_1 | 70 | 75.00 | 34.69 | 30.88 | 521 | 521 |
| P70_Peg_50 nm_1 | 70 | 75.00 | 3.83 | 279.7 | 532 | 533 |
| P45_Peg_10 nm_2 | 45 | 75.00 | 73.14 | 22.79 | 519 | 523 |
| P45_Peg_15 nm_2 | 45 | 75.0 | 35.50 | 46.95 | 521 | 526 |

Effects of polyP-Gold Nanoparticle on Blood Coagulation Kinetics—Measured by Coagulometry.

Figure 77:
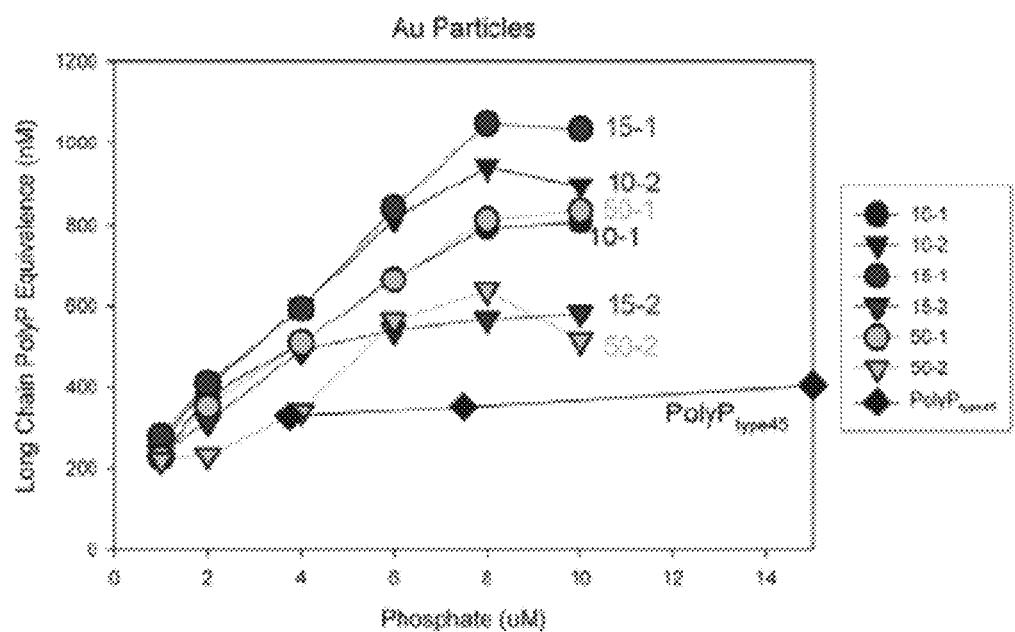
FIG. 77 shows a graph of cumulative clotting activity for 10 nm, 15 nm, and 50 nm polyP45-gold nanoparticles (refer to Table 13 for sample information), according to embodiments of the present disclosure.
Figure 78:
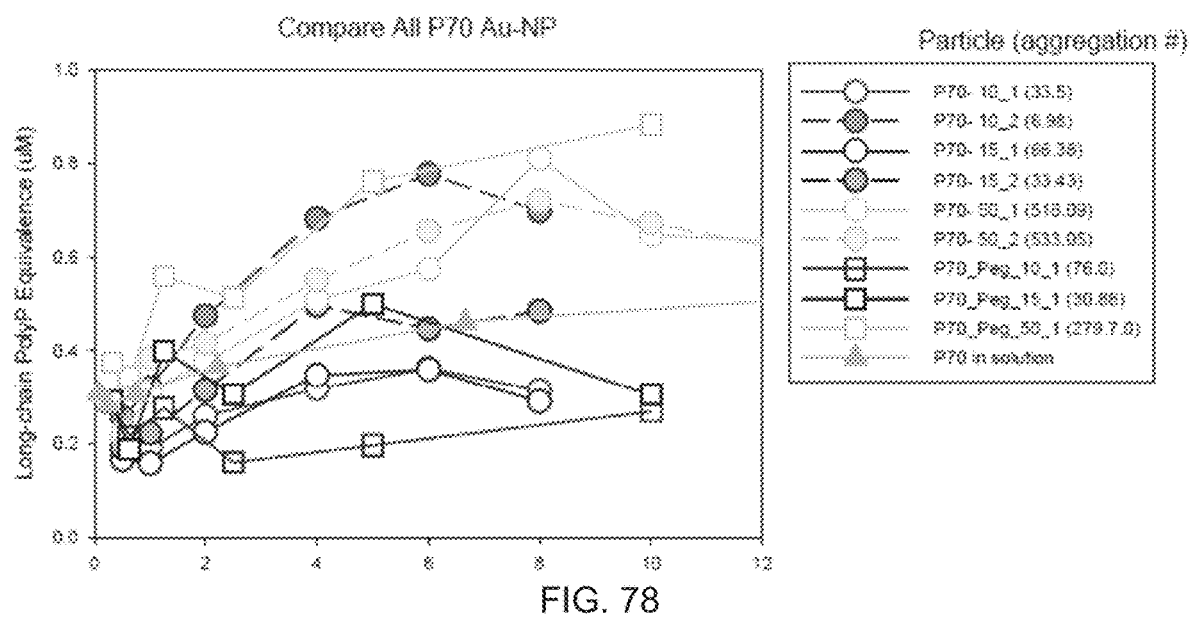
FIG. 78 shows a graph of cumulative clotting activity for 10 nm, 15 nm, and 50 nm polyP70-gold nanoparticles (refer to Tables 14 and 15 for sample information), according to embodiments of the present disclosure.

The samples presented in the section above were tested for clotting using coagulometry. The experiments performed focused on contact pathway activation. The activation of the contact pathway by polyP-gold nanoparticles was expressed in terms of equivalent long-chain polyP concentrations (FIGS. 77 and 78). Long-chain polyP, which was a heterogeneous mixture of polymers greater than 500 repeating units, induced the intrinsic contact pathway of blood coagulation. The results indicated that the polyP45-gold nanoparticle samples had increased procoagulant activity compared to free-floating polyP45 of the same concentration in solution (FIG. 77). For each particle diameter of the polyP45-gold nanoparticle samples that were synthesized, there was a direct correlation between aggregation number and increased procoagulant activity. An increased activity of some 10 nm and 15 nm samples when compared to 50 nm may be due to agglomeration of smaller size gold nanoparticles as indicated by the UV-vis peak shift after purification. In some instances, coagulation may depend on the surface density of the procoagulant ligand polyP and the total surface area of the gold. The citrate gold nanoparticles also acted as contact pathway initiators due to their negative surface charges, but to a lesser extent than the polyP-gold nanoparticle conjugates.

Figure 79:
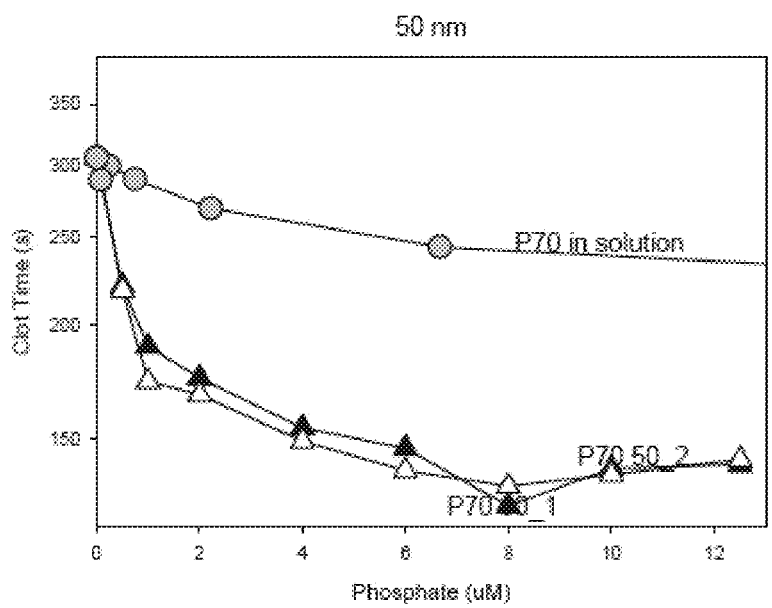
FIG. 79 shows a graph of contact pathway activation of polyP70-50 nm gold nanoparticles (refer to Table 14 for sample information) at a constant gold particle concentration, according to embodiments of the present disclosure.
Figure 80:
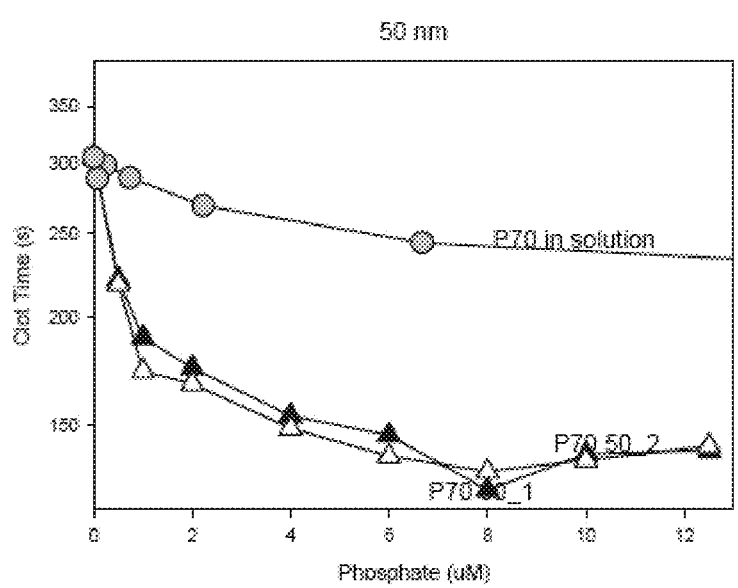
FIG. 80 shows contact pathway activation data for polyP70-50 nm gold nanoparticles (refer to Table 14 for sample information) at constant phosphate concentration, according to embodiments of the present disclosure.
Figure 81:
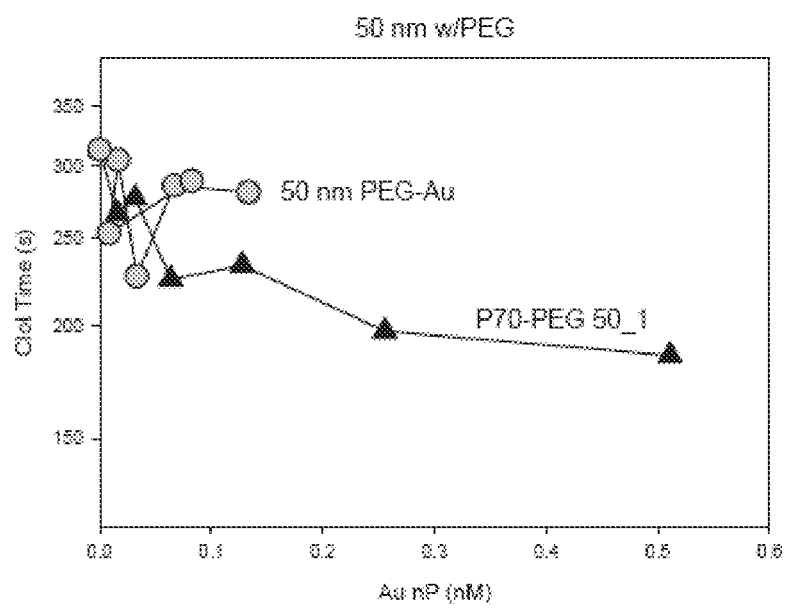
FIG. 81 shows contact pathway activation data for polyP70-Peg (3:1)-50 nm gold nanoparticles (refer to Table 15 for sample information) at constant gold nanoparticle concentration, according to embodiments of the present disclosure.

The initial contact pathway activation coagulometry experiments for polyP70-gold nanoparticles showed an increased activity of 50 nm polyP70-gold samples when compared to free floating polyP70 in solution. There was no significant difference between the 10 nm and 15 nm polyP70-gold nanoparticles and corresponding aqueous polyP70 (FIG. 78). The increased activity of the 50 nm polyP70-gold nanoparticle is shown in FIGS. 79-81. The fully PEGylated 50 nm gold nanoparticle as a negative control did not show procoagulant activity (FIG. 81). The partially PEGylated 50 nm polyP70-gold nanoparticle (with less polyP conjugated to gold nanoparticles) showed reduced procoagulant activity as expected, which was still more active than free-floating polyP70 at the same concentration.

The results indicate that the polyP-functionalized gold particles are more procoagulant than aqueous polyP of the same polymer length. 50 nm particles induced blood coagulation.

Blood Coagulation Kinetics—Measured by Microplate-Based Florescent Assays

Figure 82:
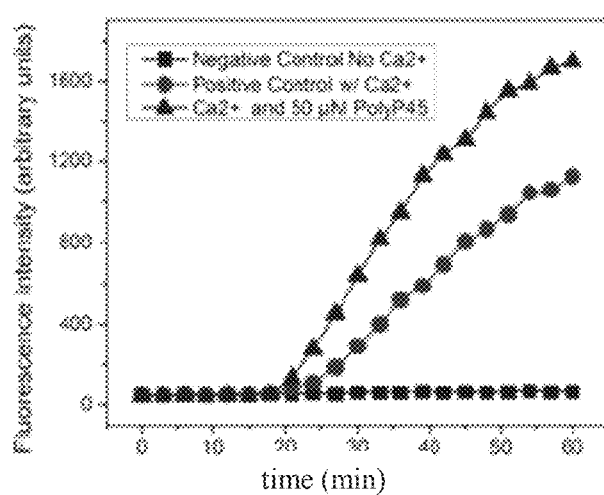
FIG. 82 shows a graph of fluorescent measurements for induction of the contact pathway with aqueous polyP45 using a fluorogenic thrombin substrate, according to embodiments of the present disclosure.

Activation of the intrinsic pathway of blood coagulation was assessed by using a fluorogenic thrombin substrate. A negative control containing no $Ca^{2+}$, and a positive control containing no polyP were also run to validate the experiment. To find the clotting time, the data were fitted to a sigmoidal function. The rate of thrombin substrate cleavage was found by taking the time derivative of the fluorescence intensity of the fitted curve, and the clotting time was defined in the relevant samples to be one-half the maximum rate of substrate cleavage. Clotting kinetics was first measured using free polyP45. Clotting induction occurred only in the presence of calcium cations (FIG. 82).

Controlled Particle Aggregation by Using Thermosensitive Polymers

Figure 83:
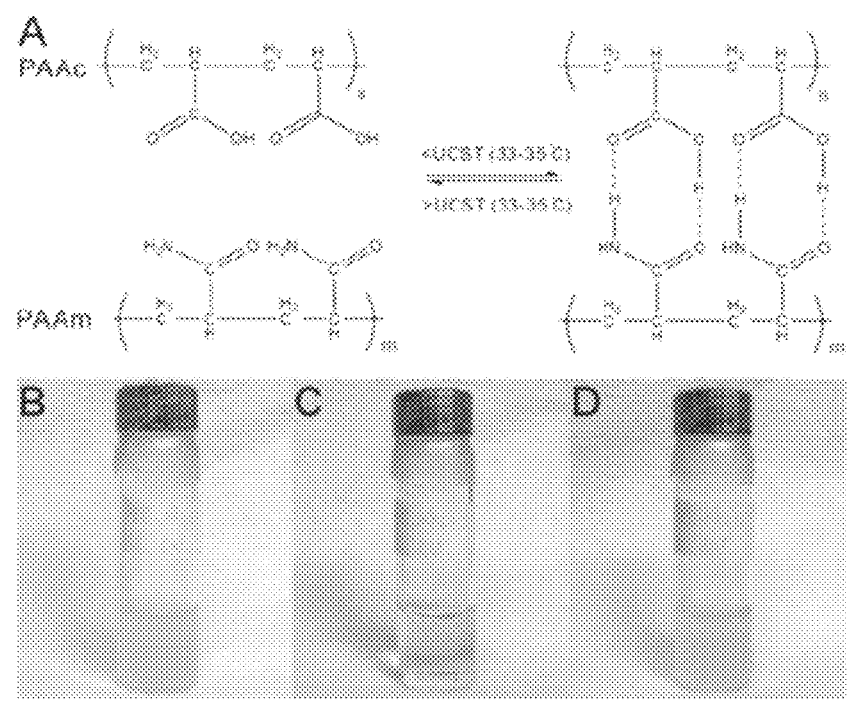
FIG. 83, panel A, to FIG. 83, panel D, show the assembly and disassembly of inter-molecular hydrogen bonding between PAAc and PAAm, according to embodiments of the present disclosure.

Controlled aggregation of smaller nanoparticles (~15 nm) into bigger ones (>50 nm) may trigger blood coagulation rapidly via contact pathway initiation as well as FV at the site of vessel or organ damage, while not significantly activating coagulation at other locations. Body temperature drop at the local trauma site due to the lack of blood and oxygen may be used to initiate controlled coagulation at the local trauma site. Poly(acrylic acid) (PAAc) and polyacrylamide (PAAm) were conjugated to gold nanoparticles through disulfide bonds. PAAc and PAAm are thermosensitive polymers with an upper critical solution temperature (UCST) around 33-35° C. When the temperature was below the UCST, PAAc and PAAm formed inter-molecular hydrogen bonding, which increased the hydrophobicity of the polymers and resulted in aggregation of the particles and phase separation (FIG. 83, panel A). The process was reversible. When the temperature was above the UCST, the hydrogen bonding disassembled and the phase separation disappeared.

Reversible Hydrogen Bonding

The assembly and disassembly of inter-molecular hydrogen bonding between PAAc and PAAm were observed (FIG. 83, panel B, to FIG. 83, panel D). A mixture of 10 wt % PAAc and 10 wt % PAAm was prepared at room temperature (~20° C.), which was below the UCST. Hydrogen bonding formed immediately and resulted in turbidity of the solution, which indicated phase separation between the polymers and water (FIG. 83, panel B). The sample was then heated up to 40° C. in a water bath. The solution turned clear, which indicated the disassembly of hydrogen bonding (FIG. 83, panel C). The sample became turbid again when it was cooled back to room temperature, which indicated the reformation of hydrogen bonding and the reversibility of the process (FIG. 83, panel D).

Conjugation Reaction and Particle Characterization

Figure 84:
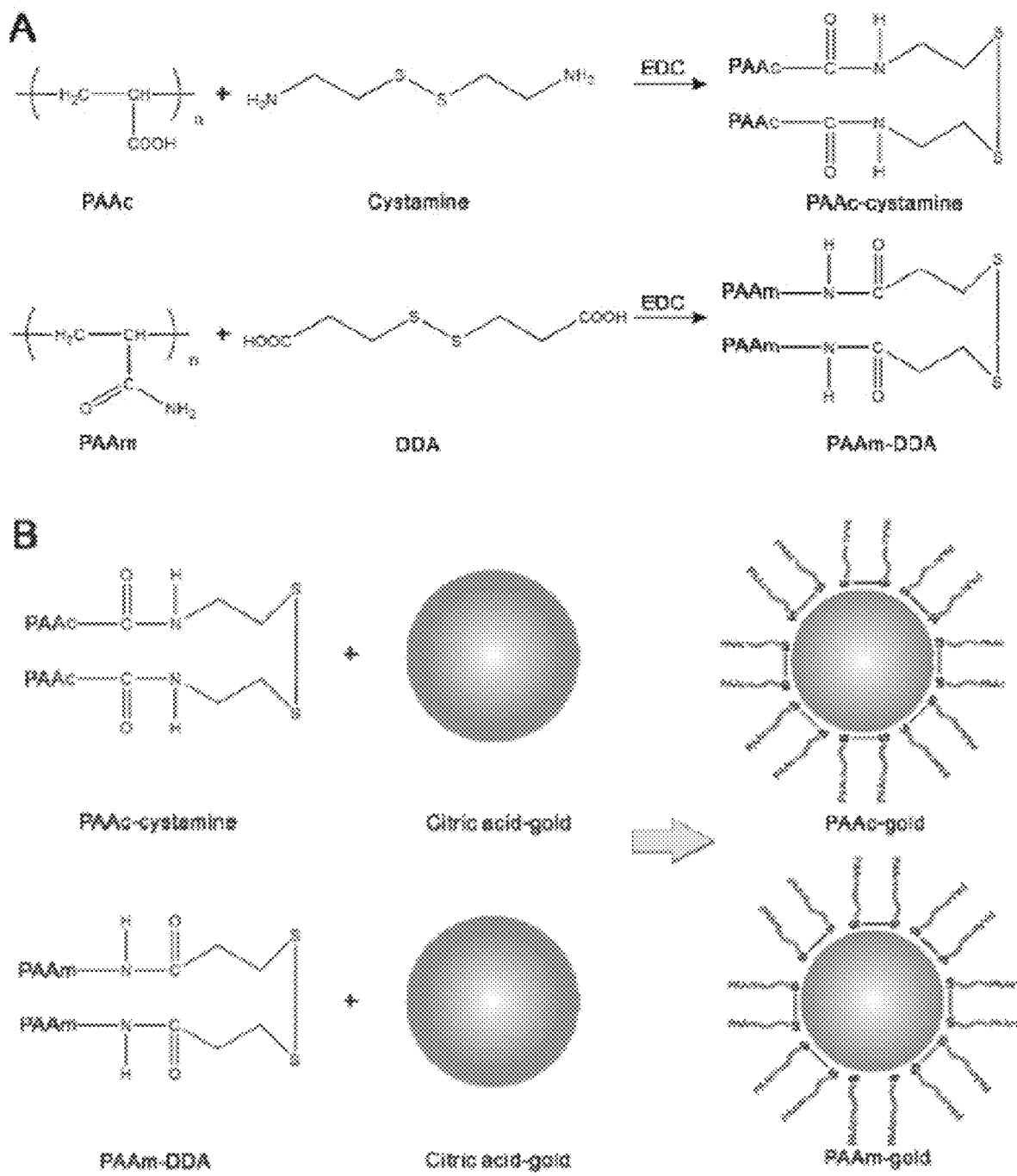
FIG. 84, panel A, and FIG. 84, panel B, show schematics of the process of synthesizing gold nanoparticles conjugated with the thermosensitive polymers, according to embodiments of the present disclosure.

Three steps were involved in synthesizing and characterizing the nanoparticles conjugated with the thermosensitive polymers, as shown in FIG. 84. (1) PAAc and PAAm were conjugated to cystamine and 3,3'-dithiodipropionic acid (DDA) respectively which contain disulfide bonds. (2) PAAc-cystamine or PAAm-DDA was attached to the surface of gold particles through the disulfide bond. (3) The particles were separated from the unreacted molecules by using centrifugation and characterized by using dynamic light scattering (DLS) and UV-vis spectroscopy.

PAAc was conjugated to cystamine using the zero-length cross-linking reagent, EDAC (1-ethyl-3-[3-(dimethylamino)propyl]carbodiimide). Different pH conditions were used to test the conjugation efficiency between PAAc and cystamine. An excess amount of PAAc was used to ensure the complete reaction of cystamine. The fluorescamine assay was utilized to test the amount of the unreacted primary amines on cystamine, which indicated the conjugation efficiency. The results are shown in Table 16. The reactions were efficient at neutral and slightly basic conditions. Conjugation efficiencies above 95% were consistently achieved for all the samples. Similar reaction conditions were used for the reaction of PAAm with DDA.

TABLE 16

Conjugation efficiency of PAAc-cystamine at various pH conditions

|  | pH | Efficiency (24 h) | Efficiency (48 h) |
| --- | --- | --- | --- |
| MES_pH4 | 7.2 | 96.1% | 96.6% |
| MES_pH6 | 8.0 | 97.7% | 95.5% |
| MES_pH8 | 9.1 | 96.5% | 97.8% |

PAAc-Gold and PAAm-Gold Conjugation

Disulfide bonds on PAAc-cystamine and PAAm-DDA were used to replace the citrate on the surface of the gold nanoparticles through ligand exchange. PAAc-cystamine or PAAm-DDA was mixed with citrate gold nanoparticles in DI water for 24 hours. Next, 10 µL of 5M NaCl was added for four consecutive days to increase the ionic strength of the solution so that more ligands could access the gold surface. Centrifugation was used to remove unreacted polymers and reagents in the suspensions. UV-visible spectroscopy and DLS were used to confirm the sizes of PAAc-gold and PAAm-gold conjugations. The shift of the absorbance peak indicated the aggregation of the gold nanoparticles.

Various conditions were tested to generate stable PAAc-gold conjugation, as shown in Table 17. C—N linkage showed good stability in a broad pH range from pH 4 to pH 9. The initial ligand replacement was tested with and without buffers.

TABLE 17

Stability of gold nanoparticles conjugated with PAAc

| Sample ID | Gold particle size (nm) | PAAc-cystamine (0.1 mM) | polyP-cystamine (0.1 mM) | Buffer | UV (AS) | UV (AP) | Stability |
|---|---|---|---|---|---|---|---|
| PAAc_10 nm_polyP(13) | 10 | 7.5 µL | 22.5 µL | MES (0.5M) 120 µL | 519.5 | 522 | yes |
| PAAc_10 nm_polyP(11) | 10 | 15 µL | 15 µL | MES (0.5M) 120 µL | 520 | 522 | yes |
| PAAc_10 nm_30_MES | 10 | 30 µL | — | MES (0.5M) 120 µL | 527 | — | no |
| PAAc_10 nm_30_BA | 10 | 30 µL | — | BA (0.25M) 30 µL | 608 | — | no |
| PAAc_10 nm_20_BA | 10 | 20 µL | — | BA (0.25M) 30 µL | 617.5 | — | no |
| PAAc_10 nm_30 | 10 | 30 µL | — | — | 535.5 | — | no |
| PAAc_10 nm_20 | 10 | 20 µL | — | — | 533 | — | no |
| PAAc_10 nm_15 | 10 | 15 µL | — | — | 534.5 | — | no |
| PAAc_15 nm_15 | 15 | 15 µL | — | — | 522 | 523 | yes |

Abbreviations used in the table: AS—after salt addition, and AP—after purification Conjugation of PAAm-DDA with gold nanoparticles to form PAAm-gold was characterized and summarized in Table 18.

Reversible Particle Aggregation Upon temperature Change

PAAc_10 nm_polyP(13) and PAAm_10 nm_polyP(13) were mixed at a 1:1 volume ratio. DLS and UV-visible absorbance were used to test the size of gold nanoparticles at different temperatures. The absorbance peaks of PAAc_10 nm_polyP(13) and PAAm_10 nm_polyP(13) were 523.5 and 522, respectively. After mixing PAAc_10 nm_polyP(13) and PAAm_10 nm_polyP(13) at a 1:1 ratio at 20° C., the absorbance peak was 524 nm, which showed no significant increase. The aggregation of PAAc_10 nm_polyP(13) and PAAm_10 nm_polyP(13), if any, was caused by the formation of intermolecular hydrogen bonding between PAAc and

TABLE 18

Stability of gold nanoparticles conjugated with PAAm

| Sample ID | Gold particle size (nm) | PAAm-DDA (0.1 mM) | polyP-cystamine (0.1 mM) | Buffer | UV (AS) | UV (AP) | Stability |
|---|---|---|---|---|---|---|---|
| PAAm_10 nm_polyP(13) | 10 | 7.5 µL | 22.5 µL | MES (0.5M) 120 µL | 520.5 | 521 | yes |
| PAAm_10 nm_polyP(11) | 10 | 15 µL | 15 µL | MES (0.5M) 120 µL | 518.5 | 521.5 | yes |
| PAAm_10 nm_30_MES | 10 | 30 µL | — | MES (0.5M) 120 µL | 527 | 526.5 | no |
| PAAm_10 nm_30_BA | 10 | 30 µL | — | BA (0.25M) 3 µL | 521 | 524 | yes |
| PAAm_10 nm_20_BA | 10 | 20 µL | — | BA (0.25M) 30 µL | 519.5 | 521 | yes |
| PAAm_15 nm_15 | 15 | 15 µL | — | — | 530 | — | no |
| PAAm_15 nm_15_BA | 15 | 15 µL | — | BA (0.25M) 30 µL | 533 | — | no |
| PAAc_15 nm_7.5_BA | 15 | 7.5 µL | — | BA (0.25M) 30 µL | 525.5 | 525.5 | yes |

Abbreviations used in the table: AS—after salt addition, and AP—after purification PAAm, which may not induce any significant peak shift since the hard core of the particles may be still sufficiently separated.

DLS was also used to test the size distribution of gold nanoparticles at different temperatures. The size of PAAc_10 nm_polyP(13) and PAAm_10 nm_polyP(13) peaked at 9 nm consistently at 25° C. and 37° C.

Figure 85:
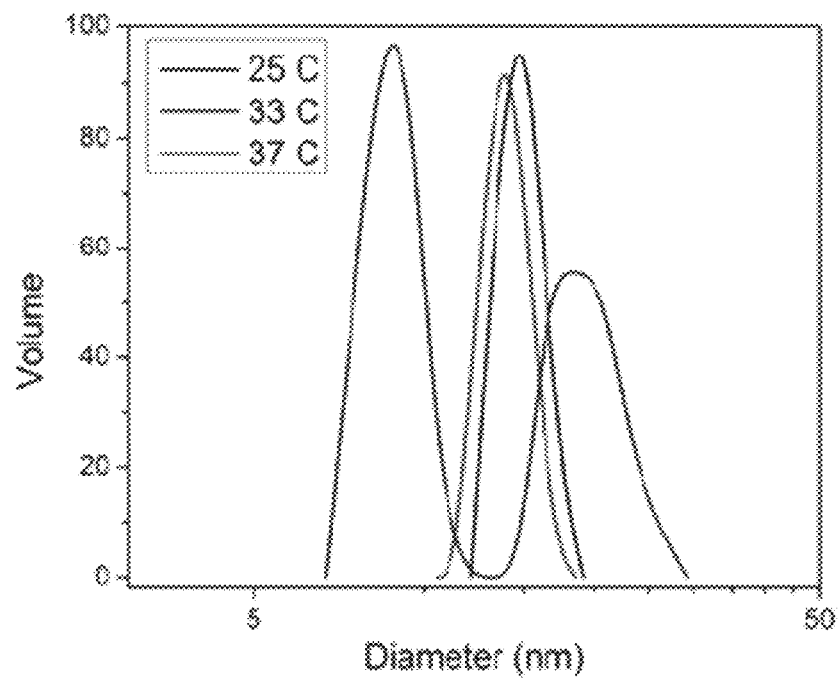
FIG. 85 shows a graph of the size distribution of the nanoparticles after mixing PAAc_10 nm_polyP(13) with PAAm_10 nm_polyP(13) at a 1:1 ratio at 25° C., 33° C. and 37° C., according to embodiments of the present disclosure.

The size and size distribution of the mixture of PAAc_10 nm_polyP(13) and PAAm_10 nm_polyP(13) at 25° C., 33° C. and 37° C. are shown in FIG. 85. Aggregation was observed at 25° C. and 33° C. The size of PAAcm_10 nm_polyP(13) at 25° C. and 33° C. was 15.2 nm and 14 nm respectively, while the original size of the gold nanoparticles by DLS was about 9 nm. When the temperature was increased to 37° C., which was above the UCST of PAAc and PAAm, the hydrogen bonding disassembled and the size of the gold nanoparticles reduced back to about 9 nm.

Figure 86:
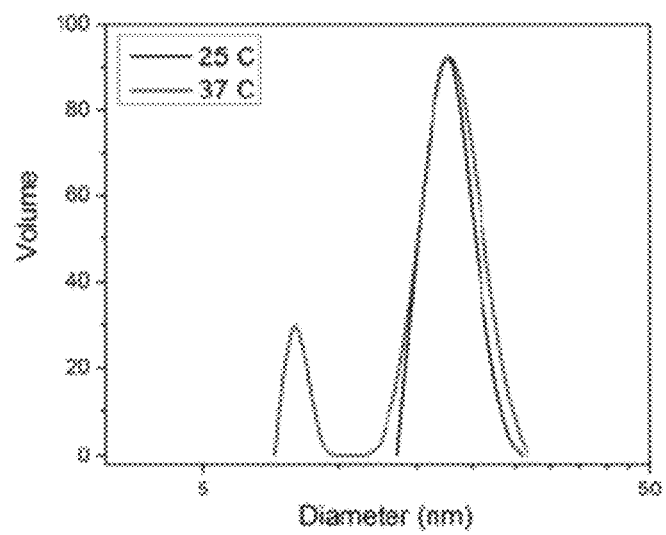
FIG. 86 shows a graph of the size distribution of the nanoparticles after mixing PAAc_10 nm_polyP(11) with PAAm_10 nm_polyP(11) at a 1:1 ratio at 25° C. and 37° C., according to embodiments of the present disclosure.

A mixture of PAAc_10 nm_polyP(11) and PAAm_10 nm_polyP(11) at a 1:1 ratio also showed similar results of particle aggregation (FIG. 86). At 25° C., average size measured by DLS was 17.5 nm. When the temperature was increased to 37° C., a small peak at 8 nm appeared which indicated the disassembly of the inter-molecular hydrogen bonding between PAAc and PAAm.

PAAc_10 nm_polyP(11) or PAAm_10 nm_polyP(11) had more PAAc or PAAm and less polyP on the surface of the gold nanoparticles as compared to PAAc_10 nm_polyP(13) or PAAm_10 nm_polyP(13). Thus, it was relatively more difficult to disassemble all the hydrogen bonding and resuspend the nanoparticles back to their original size.

In order to generate bigger aggregation, PAAc or PAAm was conjugated to the surface of gold nanoparticles alone without polyP. However, when mixing PAAc_15 nm_15 and PAAm_10 nm_20_BA at a 1:1 ratio, aggregation was not found.

Silica Nanoparticle (SNP) Synthesis

Figure 87:
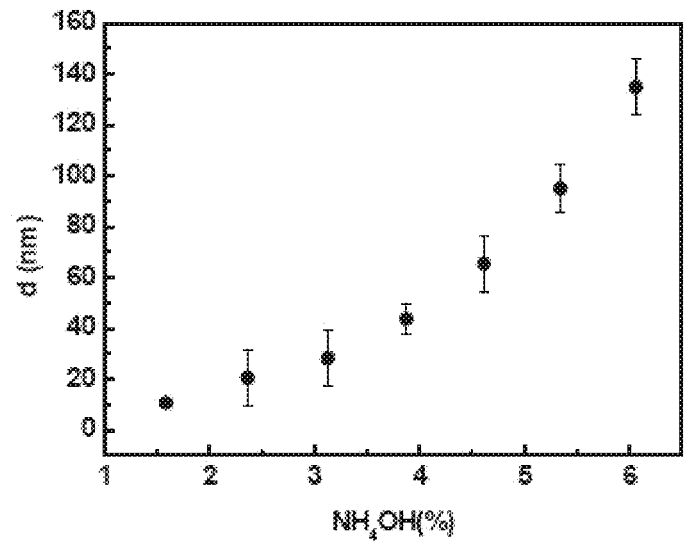
FIG. 87 shows a graph of particle size of SNP based on % NH4OH added, according to embodiments of the present disclosure.
Figure 88:
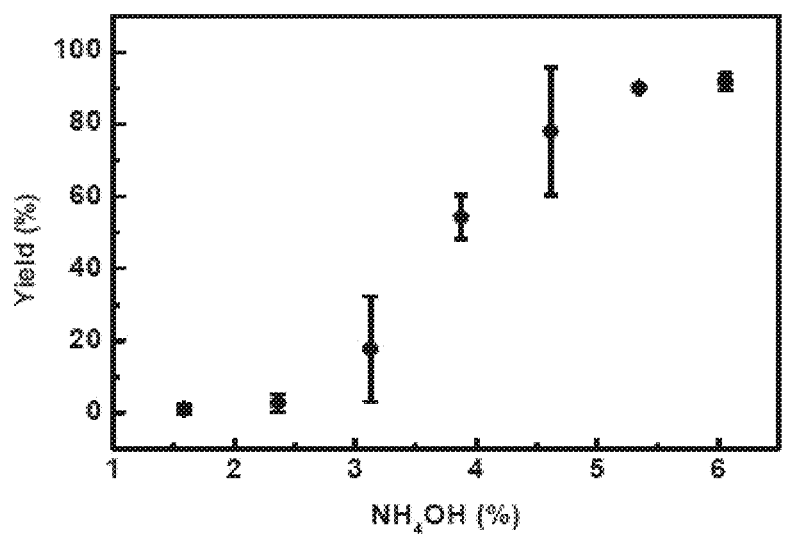
FIG. 88 shows a graph of silica yield based on % NH4OH added, according to embodiments of the present disclosure.

Experiments were performed with silica nanoparticles (SNPs) and polyP-functionalized silica nanoparticles (SNP—P70) to measure the effect of the silica particles' size and concentration on coagulation. Particles above 10 nm were synthesized following a modified Stöber method and recovered using centrifugation. The different nanoparticle sizes were obtained by varying the amounts of tetraethoxysilane (TEOS) and ammonia ($NH_4OH$) (FIG. 87). Ludox silica nanoparticles below 10 nm (Sigma Aldrich) were also tested. Silica nanoparticles below 50 nm were isolated by ultrafiltration and ultracentrifugation for coagulation and functionalization experiments. Yield of greater than 40% was achieved using greater than 4% $NH_4OH$. Syntheses below 4% $NH_4OH$ produced a yield below 40% (FIG. 88). The lack of ammonia may have reduced catalysis of the TEOS hydrolysis reaction. Zeta potential tests showed that SNPs had a negative charge in simulated body fluid, which facilitated activation of the intrinsic pathway by activating FXII. Zeta potential did not show a significant systematic change in coagulation with respect to size or pH.

Clotting experiments described above compared the silica particles at either a fixed concentration of 0.68 mg/mL (25 mg/mL stock solution) or at a fixed size of 55 nm to determine high activity range boundaries. Each particle formed an initial clot (R) between 3 and 5 min. The threshold for minimum R value occurred at a particle size of ~30 nm. Experiments in which particles below 20 nm were synthesized exhibited a bimodal size distribution when measured using DLS. The bimodal size distribution may be a result of a lack of ammonia.

Figure 89:
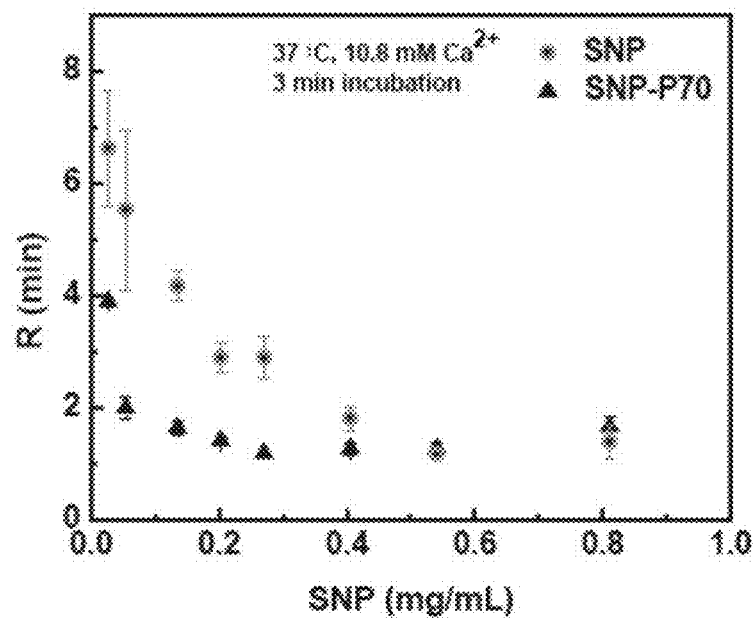
FIG. 89 shows a graph of clotting time for SNP—P70, which had a shorter clotting time (R, min) at half the concentration than bare silica, according to embodiments of the present disclosure. Experimental conditions: 37° C., 11 mM Ca$^{2+}$.

Utilizing phospholipids which increase coagulation through FXa, R was minimized to less than two minutes. In FIG. 89, the concentration dependence of R for two SNP and SNP—P70 was examined. P70 was a polyP chain that was approximately 70mer in length, which was roughly the same size as polyP produced by activated platelets as part of the coagulation cascade. At low particle concentrations, the R value was high (clotting time was long). As the particle concentration increased, R decreased until the threshold condition was met. For bare silica, the threshold concentration occurred at 0.54 mg/ml. SNP—P70 reached a threshold at a concentration of 0.27 mg/ml, half that of bare SNP. Above the threshold concentration the R value remained low, until at much higher concentration the particles may inhibit clotting due to particle aggregation or dilution of plasma factors over the particle's surface area.

Other parameters may also be evaluated, such as rate of clot formation, and clot size, since the agents attached to the particle may affect the initial clot formation time, but could accelerate the clotting when initiated or result in the formation of a bigger clot. Tests confirmed that the particles maintained stability and size, at all concentrations, indicating particle sizes varied due to synthesis conditions.

In addition to solid non-porous nanoparticles, large-pore mesoporous nanospheres (MSN) may be used to deliver procoagulant proteins such as thrombin, prothombin or tissue factor to wounds. The large pore size and increased accessible surface may increase coagulation by allowing proteins to adsorb to the surface and activate. For example, ordered mesoporous nanoparticles in the 50-200 nm range size with a pore size between 10-30 nm may be used.

Functionalizing the nanoparticles with polyP or prothrombin may enhance the procoagulant nature of the particles. The polyP used was a ~70-mer length (P70) that was similar in size to polyP secreted by human platelets during clotting. P70 directly adsorbed to silica was found to increase the particle size by several nm. SNPs were tested with and without adsorbed polyP and found that P70-bound SNPs significantly decreased clotting time when compared to bare SNP (FIG. 89). SNP—P70 also improved clotting time when compared to P70 added directly to plasma. The SNP scaffold thus served as a mechanism to deliver the P70 triggering agent to the wound to initiate clotting.

Figure 90:
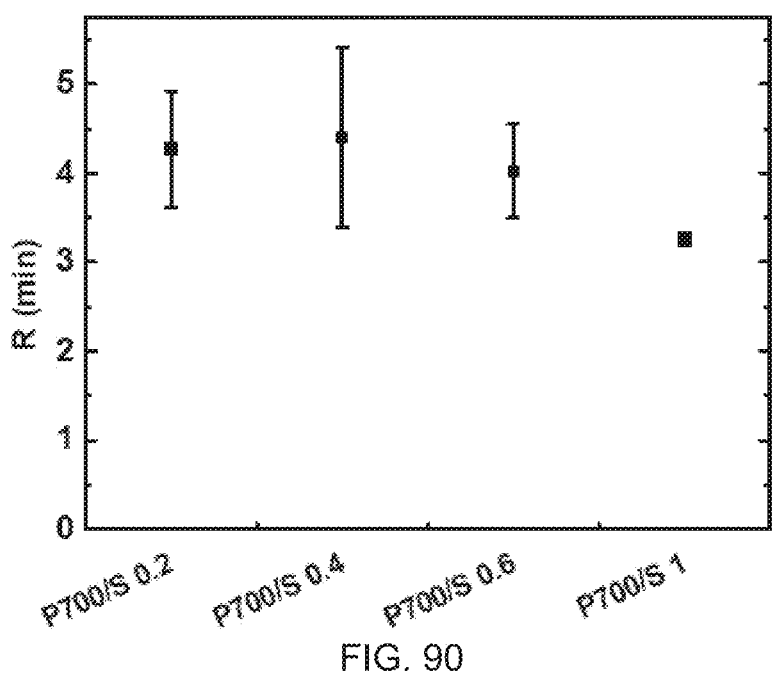
FIG. 90 shows a graph of clot time for various ratios of P700:SNP (0.2, 0.4, 0.6, and 1), according to embodiments of the present disclosure.

Experiments were performed using longer polyPs chains, such as ~700-mer polyP (P700). PolyP with a size range above 500mers was shown to accelerate the contact or intrinsic pathway by activating FXII. The P700 was attached to the scaffolds using the same methods described above. Four different ratios of P700:SNP were tested –0.2, 0.4, 0.6, and 1. Similar to P70, clotting assays suggested that clot time decreased with a ratio of P700:SNP above 0.5. A 1:1 ratio minimized clot time (FIG. 90).

Samples of SNP, SNP—P70, and SNP—P700 nanoparticles were used for polyP quantification and further coagulation tests. These tests revealed that SNP—P70 particles with a concentration of roughly 25 nmol $PO_4$/mg SNP (quantified by hydrolysis) exhibited higher procoagulant activity than SNP—P70 particles with a higher nmol $PO_4$/mg SNP concentration.

In addition to TEG, the coagulation threshold response was also tested using a thrombinspecific blue coumarin dye. A small concentration of dye was added to the recalcified plasma. As clotting progressed and thrombin was produced, the thrombin cleaved the coumarin dye causing the solution to fluoresce. Rapid fluorescence signified the thrombin burst, which led to clot formation. A fluorescence microscope captured the qualitative change as shown in FIG. 70.

Thrombin generation was also monitored using a plate reader. By reading fluorescence every 10 seconds, the thrombin burst was identified. As clotting occurred near the rapid rise section of the thrombin burst, the clot time was determined from the fluorescence data plot.

After determining the procoagulant activity of SNP—P70 under normal conditions as discussed above, the SNP—P70 TSPs were applied under traumatic conditions. A traumatic injury can quickly develop into coagulopathy, the fundamental breakdown of the human coagulation cascade. Though coagulopathy can exist either as a hypercoagulant or hypocoagulant form, as used herein coagulopathy is the fundamental breakdown of the coagulation cascade that impairs clot formation. In the presence of trauma, the coagulopathic body becomes weakened such that anticoagulant pathways take over and a clot cannot form.

Coagulopathy exists in three states known as the "lethal triad"—dilution, hypothermia, and acidosis. Each damages the cascade in a specific way. In a coagulopathic state, all three states combine to inhibit clot formation. In these experiments, dilution was mimicked using a phosphate buffered solution (PBS). Incubating plasma below the usual 37° C. was used to create hypothermic conditions. A dilute phosphoric acid solution was used to acidify the plasma below a pH of 7.1 to create an acidosis condition. The experiments utilized a set concentration of lipidated tissue factor (LTF)—0.5 ng/ml for TEG tests, 0.185 ng/ml for fluorescence dye tests—to produce timely initiation of the coagulation cascade through the extrinsic pathway and the body's main response to vessel injury. The SNP—P70 TSP was tested at 0.25 mg/ml without LTF to compare its ability to form clots.

Figure 91:
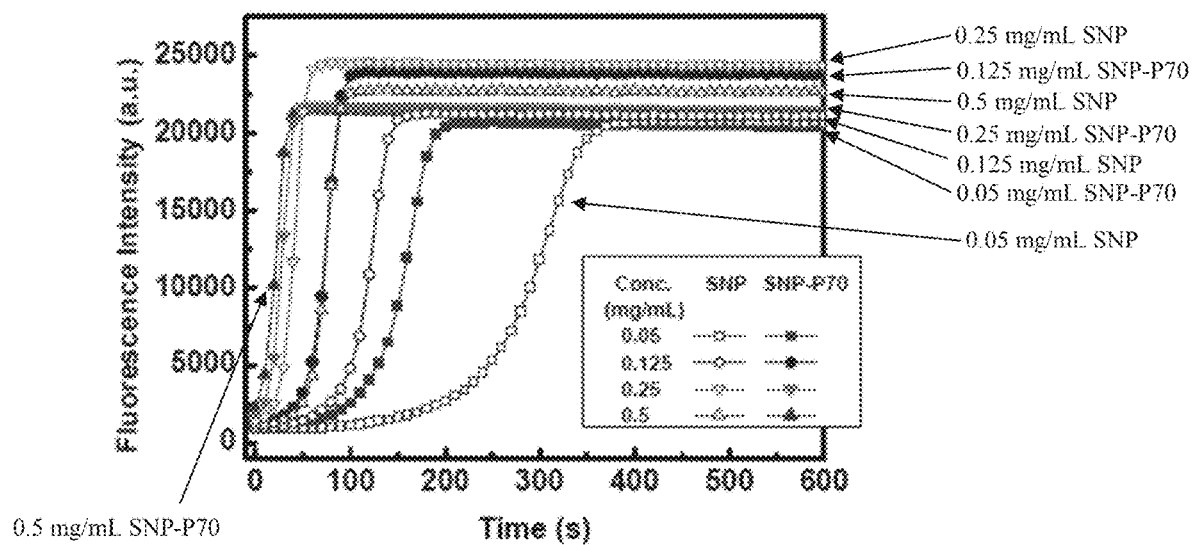
FIG. 91 shows a graph of fluorescence intensity over time, which shows that SNP—P70 generated thrombin quicker than SNP, according to embodiments of the present disclosure.
Figure 92:
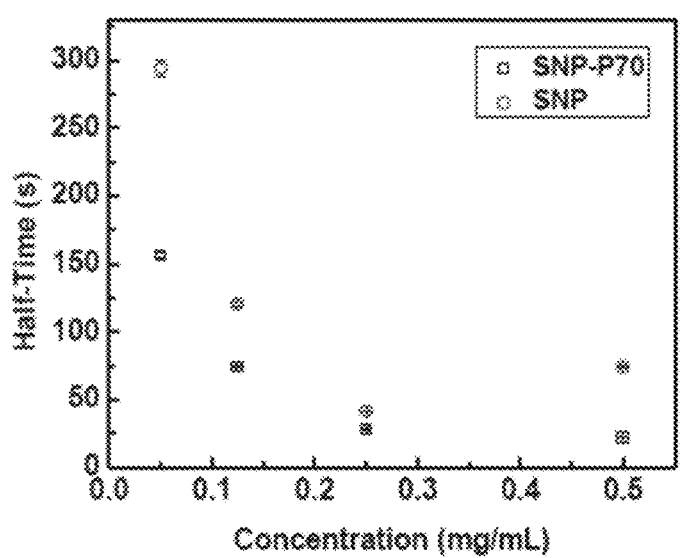
FIG. 92 shows a graph of the same fluorescence data as in FIG. 91, presented in terms of clot time.
Figure 93:
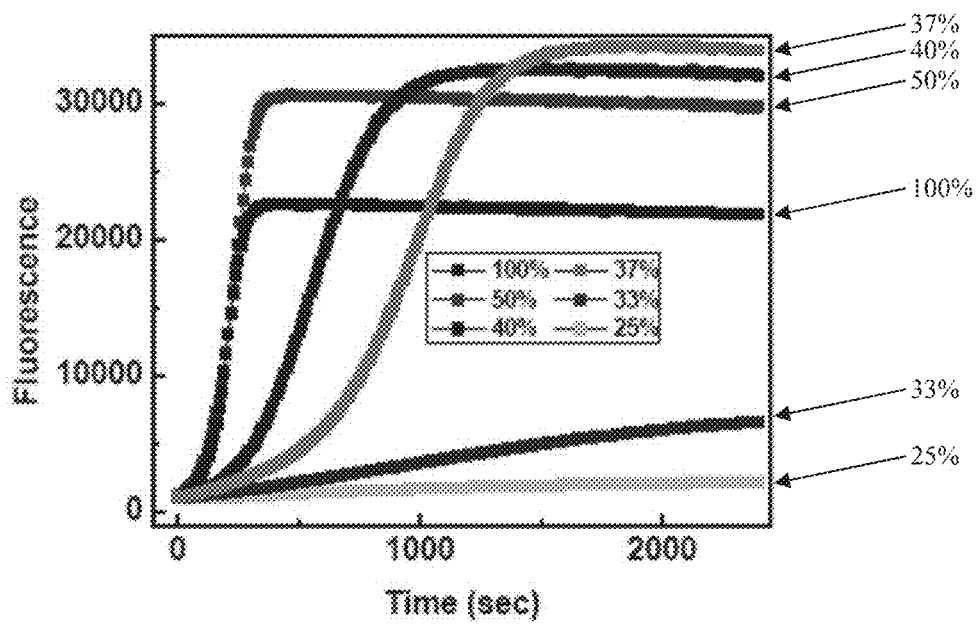
FIG. 93 shows a graph of thrombin generation times from 100% plasma to 25% plasma; i.e.: 100% is 100% plasma and 0% dilutant, according to embodiments of the present disclosure.
Figure 94:
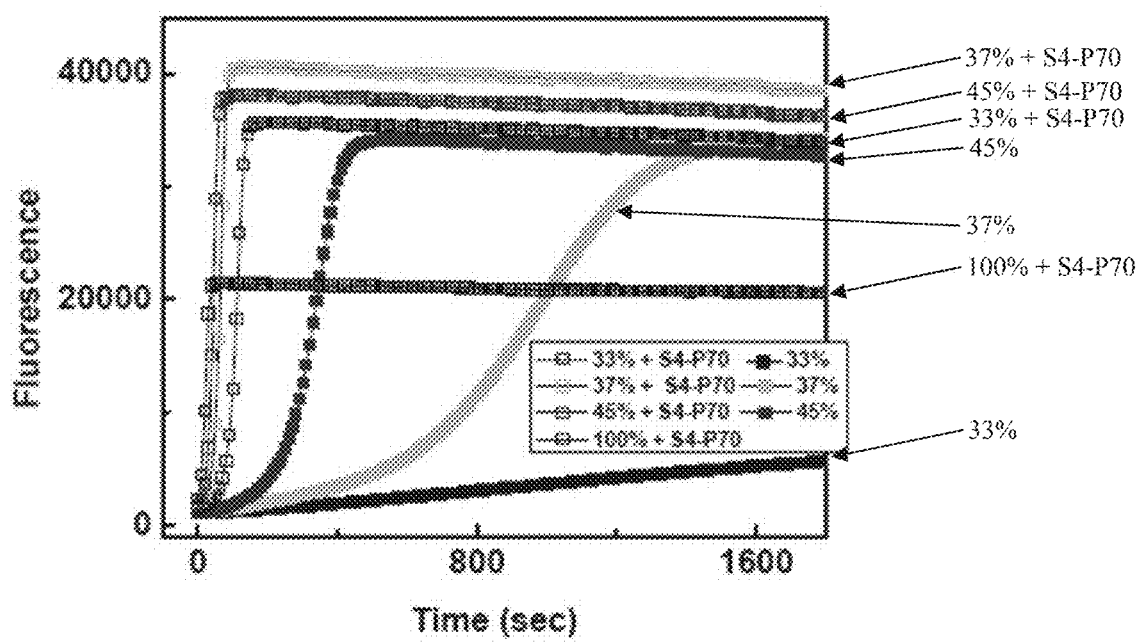
FIG. 94 shows a graph of fluorescence over time, which indicated that adding SNP—P70 generated thrombin quickly even under severe plasma dilution, according to embodiments of the present disclosure.

Due to the loss of both procoagulant and anticoagulant factors from blood loss, dilution begins to significantly inhibit clotting at the ~50% level. Using TEG and dye fluorescence, a dilution baseline was established. SNP—P70 (at the threshold concentration of ~0.25 mg/ml identified in our TEG experiments) was used to reverse the coagulopathic conditions. SNP—P70 successfully hastened thrombin burst and clot formation. (FIGS. 91 and 92). FIG. 93 shows a graph of thrombin generation times from 100% plasma to 25% plasma; i.e.: 100% is 100% plasma and 0% dilutant. FIG. 94 shows a graph of fluorescence over time, which indicated that adding SNP—P70 generated thrombin quickly even under severe plasma dilution.

Figure 95:
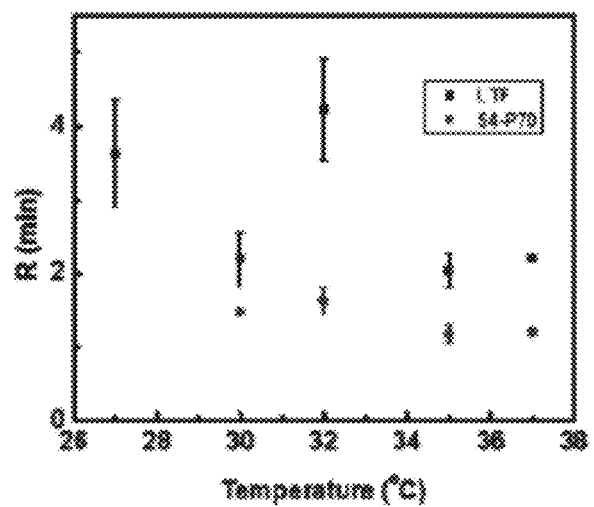
FIG. 95 shows a graph of clot time vs. temperature, which indicated that SNP—P70 TSPs initiated clots quicker under hypothermia, according to embodiments of the present disclosure.
Figure 96:
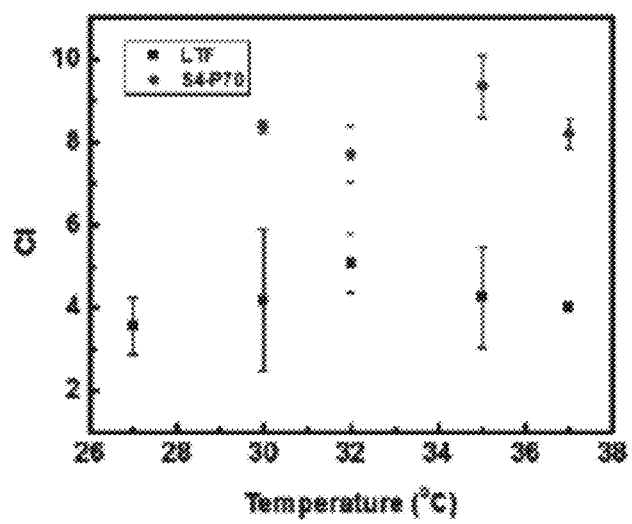
FIG. 96 shows a graph of Coagulation index (CI) vs. temperature, which indicated that SNP—P70 improved clot formation compared to lipidated tissue factor (LTF), according to embodiments of the present disclosure.

Hypothermia, the second member of the lethal triad, occurs when the body temperature drops below 37-C. The drop in temperature leads to a decreased rate in the kinetics of many of the coagulation factors, especially formation of the tissue factor-FVIIa (TF-FVIIa) complex during the initiation phase of coagulation. Unlike dilution where fibrinogen deficit triggers the drop in clotting, hypothermia slows coagulation but does not prevent it. The addition of SNP—P70 to hypothermic plasma resulted in improved coagulation across all TEG parameters. A coagulation index formula was used to show the procoagulant nature of the SNP—P70 TSP at sub-normal body temperature. Coagulation index (CI) combines all four TEG facets—R, K, alpha, and MA—into a single value; the more positive the CI, the stronger the procoagulant. FIG. 95 shows a graph of clot time vs. temperature, which indicated that SNP—P70 TSPs initiated clots quicker under hypothermia. FIG. 96 shows a graph of Coagulation index (CI) vs. temperature, which indicated that SNP—P70 improved clot formation compared to lipidated tissue factor (LTF).

The above experiments showed that SNP—P70 lowered clot times while forming strong clots as compared to bare SNP and LTF. Studies on FXII deficient plasma showed that SNP—P70 initiated clotting through FXa coagulation pathway. Finally, SNP—P70 was shown to decrease clot time and quicken thrombin generation under coagulopathic conditions often found in patients who have suffered a traumatic wound (e.g., dilution and hypothermia).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

```
Sequence total quantity: 10
SEQ ID NO: 1            moltype = AA  length = 4
FEATURE                 Location/Qualifiers
source                  1..4
                        mol_type = protein
                        organism = synthetic construct
SEQUENCE: 1
IEGR                                                                     4

SEQ ID NO: 2            moltype = AA  length = 5
FEATURE                 Location/Qualifiers
source                  1..5
                        mol_type = protein
                        organism = synthetic construct
SEQUENCE: 2
CREKA                                                                    5

SEQ ID NO: 3            moltype = AA  length = 7
FEATURE                 Location/Qualifiers
source                  1..7
                        mol_type = protein
                        organism = synthetic construct
SEQUENCE: 3
KLWVLPK                                                                  7
```

```
SEQ ID NO: 4            moltype = AA  length = 4
FEATURE                 Location/Qualifiers
source                  1..4
                        mol_type = protein
                        organism = synthetic construct
SEQUENCE: 4
TAFI                                                                     4

SEQ ID NO: 5            moltype = AA  length = 12
FEATURE                 Location/Qualifiers
source                  1..12
                        mol_type = protein
                        organism = synthetic construct
SEQUENCE: 5
NQEQVSPLTG LK                                                           12

SEQ ID NO: 6            moltype = AA  length = 14
FEATURE                 Location/Qualifiers
source                  1..14
                        mol_type = protein
                        organism = synthetic construct
SEQUENCE: 6
CGGIEGRGGS GGKG                                                         14

SEQ ID NO: 7            moltype = AA  length = 16
FEATURE                 Location/Qualifiers
source                  1..16
                        mol_type = protein
                        organism = synthetic construct
SEQUENCE: 7
CGGIEGRGGK FAMGGK                                                       16

SEQ ID NO: 8            moltype = AA  length = 14
FEATURE                 Location/Qualifiers
source                  1..14
                        mol_type = protein
                        organism = synthetic construct
SEQUENCE: 8
CGGIEGRGGS GGKG                                                         14

SEQ ID NO: 9            moltype = AA  length = 14
FEATURE                 Location/Qualifiers
source                  1..14
                        mol_type = protein
                        organism = synthetic construct
SEQUENCE: 9
CGGERGIGGS GGKG                                                         14

SEQ ID NO: 10           moltype = AA  length = 4
FEATURE                 Location/Qualifiers
source                  1..4
                        mol_type = protein
                        organism = synthetic construct
SEQUENCE: 10
SPDP                                                                     4
```

What is claimed is:

1. A method of treating a subject for a wound, the method comprising:
   administering a hemostatic agent to the subject, wherein the hemostatic agent comprises:
   a magnetic nanoparticle; and
   a polyphosphate polymer attached to the magnetic nanoparticle; and
   magnetically tracking the movement of the magnetic nanoparticle of the hemostatic agent to the wound.

2. The method of claim 1, wherein the tracking comprises imaging the hemostatic composition.

3. The method of claim 2, wherein the imaging comprises imaging the magnetic nanoparticle.

4. The method of claim 2 or 3, wherein the hemostatic agent further comprises a dye precursor that is convertable to a fluorescent dye by a coagulation factor, wherein the tracking comprises measuring fluorescence by the fluorescent dye at the wound.

5. The method of claim 4, wherein the coagulation factor is thrombin.

6. The method of claim 1, wherein the magnetic nanoparticle comprises a silver core.

7. The method of claim 1, wherein the magnetic nanoparticle comprises a silica shell.

8. The method of claim 1, wherein the magnetic nanoparticle comprises a material selected from the group consisting of iron oxide, diatomaceous earth, an aluminosilicate, an oxide of a transition metal, and titanium dioxide.

9. The method of claim 1, wherein the hemostatic agent further comprises a protecting agent attached to the magnetic nanoparticle.

10. The method of claim 9, wherein the protecting agent comprises polyethylene glycol (PEG), polyvinylpyrrolidone (PVP), poly(lactic-co-glycolic acid) (PLGA), polypropylene glycol, or a combination thereof.

* * * * *